(12) United States Patent
Herron et al.

(10) Patent No.: US 11,491,324 B2
(45) Date of Patent: Nov. 8, 2022

(54) ADJUSTABLE DEVICES FOR TREATING SLEEP APNEA, AND ASSOCIATED SYSTEMS AND METHODS

(71) Applicant: Invicta Medical, Inc., Santa Clara, CA (US)

(72) Inventors: David Herron, San Jose, CA (US); Ling-Kang Tong, Fremont, CA (US); Hoa D. Nguyen, San Jose, CA (US); Chang Yeul Lee, San Jose, CA (US)

(73) Assignee: Invicta Medical, Inc., Santa Clara, CA (US)

( * ) Notice: Subject to any disclaimer, the term of this patent is extended or adjusted under 35 U.S.C. 154(b) by 0 days.

(21) Appl. No.: 17/070,823

(22) Filed: Oct. 14, 2020

(65) Prior Publication Data

US 2021/0113832 A1    Apr. 22, 2021

Related U.S. Application Data

(60) Provisional application No. 62/916,169, filed on Oct. 16, 2019.

(51) Int. Cl.
*A61N 1/05* (2006.01)
*A61B 5/08* (2006.01)
(Continued)

(52) U.S. Cl.
CPC .............. *A61N 1/0548* (2013.01); *A61B 5/08* (2013.01); *A61B 5/395* (2021.01); *A61B 5/11* (2013.01)

(58) Field of Classification Search
CPC ........ A61N 1/0548; A61B 5/395; A61B 5/08; A61B 5/11
See application file for complete search history.

(56) References Cited

U.S. PATENT DOCUMENTS 4,558,704 A    12/1985    Petrofsky
4,830,008 A    5/1989    Meer
(Continued)

FOREIGN PATENT DOCUMENTS

CA    2477540    5/2005
CN    201361029    12/2009
(Continued)

OTHER PUBLICATIONS

International Search Report and Written Opinion for International Patent Application No. PCT/US20/55627, Applicant: Invicta Medical, Inc., dated Feb. 1, 2021, 8 pages.
(Continued)

*Primary Examiner* — Catherine M Voorhees
*Assistant Examiner* — Roland Dinga
(74) *Attorney, Agent, or Firm* — Perkins Coie LLP

(57) ABSTRACT

Intraoral electrical stimulation devices are disclosed. A representative device, which can be used to treat sleep apnea, includes an intraoral attachment body, a guide element carried by the attachment body and having a constrained guide path, and an electrode movably supported relative to the guide element and movable along the constrained guide path to a plurality of positions. A positioning member is coupleable to the electrode to move the electrode along the constrained guide path, and a signal generator is coupleable to the electrode to direct a stimulation signal to the electrode.

24 Claims, 46 Drawing Sheets

(51) Int. Cl.
*A61B 5/395* (2021.01)
*A61B 5/11* (2006.01)

(56) References Cited

U.S. PATENT DOCUMENTS

| | | | |
|---|---|---|---|
| 4,947,844 | A | 8/1990 | McDermott |
| 5,146,918 | A | 9/1992 | Kallok et al. |
| 5,190,053 | A | 3/1993 | Meer |
| 5,193,539 | A | 3/1993 | Schulman |
| 5,193,540 | A | 3/1993 | Schulman |
| 5,212,476 | A | 5/1993 | Maloney et al. |
| 5,265,624 | A | 11/1993 | Bowman |
| 5,284,161 | A | 2/1994 | Karell |
| 5,540,732 | A | 7/1996 | Testerman |
| 5,546,952 | A | 8/1996 | Erickson |
| 5,697,076 | A | 12/1997 | Troyk et al. |
| 5,792,067 | A | 8/1998 | Karell |
| 6,132,384 | A | 10/2000 | Christopherson et al. |
| 6,212,435 | B1 | 4/2001 | Lattner |
| 6,240,316 | B1 | 5/2001 | Richmond et al. |
| 6,361,494 | B1 | 3/2002 | Lindenthaler |
| 6,582,441 | B1 | 6/2003 | He et al. |
| 6,587,725 | B1 | 7/2003 | Durand et al. |
| 6,618,627 | B2 | 9/2003 | Lattner et al. |
| 6,636,767 | B1 | 10/2003 | Knudson |
| 7,367,935 | B2 | 5/2008 | Mechlenburg et al. |
| 7,369,896 | B2 | 5/2008 | Gesotti |
| 7,369,991 | B2 | 5/2008 | Manabe et al. |
| 7,371,220 | B1 | 5/2008 | Koh et al. |
| 7,574,357 | B1 | 8/2009 | Jorgensen et al. |
| 7,680,538 | B2 | 3/2010 | Durand et al. |
| 7,684,858 | B2 | 3/2010 | He et al. |
| 7,711,438 | B2 | 5/2010 | Lattner et al. |
| 7,882,842 | B2 | 2/2011 | Bhat et al. |
| 7,890,193 | B2 | 2/2011 | Tingey |
| 7,920,915 | B2 | 4/2011 | Mann |
| 8,200,486 | B1 | 6/2012 | Jorgensen et al. |
| 8,249,723 | B2 | 8/2012 | McCreery |
| 8,359,108 | B2 | 1/2013 | McCreery |
| 8,620,438 | B1 | 12/2013 | Wijting |
| 8,655,451 | B2 | 2/2014 | Klosterman |
| 8,768,474 | B1 | 7/2014 | Thompson et al. |
| 8,774,943 | B2 | 7/2014 | McCreery et al. |
| 8,855,767 | B2 | 10/2014 | Faltys et al. |
| 9,808,620 | B2 | 4/2017 | Kent |
| 9,833,613 | B2 | 12/2017 | Sama |
| 9,895,541 | B2 | 2/2018 | Meadows et al. |
| 10,058,701 | B2 | 8/2018 | Sama |
| 10,195,426 | B2 | 2/2019 | Kent |
| 10,195,427 | B2 | 2/2019 | Kent |
| 10,314,501 | B2 | 6/2019 | Zitnik et al. |
| 10,594,166 | B2 | 3/2020 | Ho et al. |
| 10,744,339 | B2 | 8/2020 | Makansi |
| 10,994,139 | B2 | 5/2021 | Fayram et al. |
| 11,033,738 | B2 | 6/2021 | Steier |
| 2001/0023362 | A1 | 9/2001 | Kobayashi |
| 2003/0069626 | A1 | 4/2003 | Lattner et al. |
| 2003/0195571 | A1 | 10/2003 | Burnes et al. |
| 2004/0073272 | A1 | 4/2004 | Knudson |
| 2004/0147975 | A1 | 7/2004 | Popovic |
| 2005/0038485 | A1* | 2/2005 | Ludwig ............. A61N 1/0548 607/42 |
| 2005/0043644 | A1 | 2/2005 | Stahmann et al. |
| 2005/0261600 | A1 | 11/2005 | Aylsworth |
| 2006/0155206 | A1 | 7/2006 | Lynn |
| 2007/0173893 | A1 | 7/2007 | Pitts |
| 2007/0277836 | A1 | 12/2007 | Longley |
| 2008/0103769 | A1 | 5/2008 | Schultz et al. |
| 2008/0208287 | A1 | 8/2008 | Palermo |
| 2009/0221943 | A1 | 9/2009 | Burbank |
| 2010/0023103 | A1 | 1/2010 | Elborno |
| 2010/0100153 | A1 | 4/2010 | Carlson et al. |
| 2010/0152546 | A1 | 6/2010 | Behan et al. |
| 2010/0152808 | A1 | 6/2010 | Boggs, II |
| 2010/0185254 | A1 | 7/2010 | Lindquist et al. |
| 2010/0201500 | A1 | 8/2010 | Stirling et al. |
| 2010/0280570 | A1 | 11/2010 | Sturm |
| 2011/0093032 | A1 | 4/2011 | Boggs, II |
| 2011/0093036 | A1 | 4/2011 | Mashiach |
| 2011/0152965 | A1 | 6/2011 | Mashiach |
| 2011/0172733 | A1 | 7/2011 | Lima et al. |
| 2011/0172743 | A1 | 7/2011 | Davis et al. |
| 2011/0213438 | A1 | 9/2011 | Lima et al. |
| 2011/0230702 | A1 | 9/2011 | Honour |
| 2011/0264164 | A1 | 10/2011 | Christopherson |
| 2012/0024297 | A1 | 2/2012 | Hedge |
| 2012/0029362 | A1 | 2/2012 | Patangay et al. |
| 2012/0089153 | A1 | 4/2012 | Christopherson |
| 2012/0192874 | A1 | 8/2012 | Bolea |
| 2012/0197340 | A1 | 8/2012 | Tesfayesus |
| 2012/0234331 | A1 | 9/2012 | Totada |
| 2013/0072999 | A1 | 3/2013 | Mashiach |
| 2013/0085537 | A1 | 4/2013 | Mashiach |
| 2013/0085544 | A1 | 4/2013 | Mashiach |
| 2013/0085545 | A1 | 4/2013 | Mashiach |
| 2013/0085558 | A1 | 4/2013 | Mashiach |
| 2013/0085559 | A1 | 4/2013 | Mashiach |
| 2013/0085560 | A1 | 4/2013 | Mashiach |
| 2013/0140289 | A1 | 6/2013 | Barateir |
| 2014/0046221 | A1 | 2/2014 | Mashiach |
| 2014/0135868 | A1 | 5/2014 | Bashyam |
| 2014/0228905 | A1 | 8/2014 | Bolea |
| 2015/0029030 | A1 | 1/2015 | Aoyama |
| 2015/0038865 | A1 | 2/2015 | Shigeto |
| 2015/0057719 | A1 | 2/2015 | Tang |
| 2015/0073232 | A1 | 3/2015 | Ahmed |
| 2015/0112697 | A1 | 4/2015 | Bradley |
| 2015/0134028 | A1 | 5/2015 | Greatbatch |
| 2015/0182753 | A1 | 7/2015 | Harris |
| 2015/0190630 | A1 | 7/2015 | Kent et al. |
| 2015/0206151 | A1 | 7/2015 | Carney |
| 2015/0224307 | A1 | 8/2015 | Cyberonics |
| 2015/0273177 | A1 | 10/2015 | Lizuka |
| 2016/0089540 | A1 | 3/2016 | Bolea |
| 2016/0114159 | A1 | 4/2016 | Kent |
| 2016/0235981 | A1 | 8/2016 | Southwell |
| 2016/0317345 | A1 | 11/2016 | Marie |
| 2017/0014068 | A1 | 1/2017 | Gotoh et al. |
| 2017/0095667 | A1 | 4/2017 | Yakovlev |
| 2017/0135604 | A1 | 5/2017 | Kent |
| 2017/0135629 | A1 | 5/2017 | Kent |
| 2017/0143257 | A1 | 5/2017 | Kent |
| 2017/0143259 | A1 | 5/2017 | Kent |
| 2017/0143280 | A1 | 5/2017 | Kent |
| 2017/0143960 | A1 | 5/2017 | Kent |
| 2017/0224987 | A1 | 8/2017 | Kent |
| 2018/0221660 | A1 | 8/2018 | Suri et al. |
| 2019/0001139 | A1 | 1/2019 | Mishra et al. |
| 2019/0022383 | A1 | 1/2019 | Hadlock |
| 2019/0057700 | A1 | 2/2019 | Kent |
| 2019/0099285 | A1 | 4/2019 | Bachelder et al. |
| 2019/0117967 | A1 | 4/2019 | Scheiner |
| 2019/0374776 | A1 | 12/2019 | Mishra et al. |
| 2020/0001077 | A1 | 1/2020 | Kent |
| 2020/0016401 | A1 | 1/2020 | Papay et al. |
| 2020/0069947 | A1 | 3/2020 | Kent |
| 2020/0346010 | A1 | 11/2020 | Papay et al. |
| 2020/0346016 | A1 | 11/2020 | Caparso et al. |
| 2020/0376261 | A1* | 12/2020 | Stevens ............. A61N 1/0456 |
| 2021/0106824 | A1 | 4/2021 | Caparso et al. |
| 2022/0032052 | A1 | 2/2022 | Kent et al. |

FOREIGN PATENT DOCUMENTS

| | | |
|---|---|---|
| EP | 1128868 | 3/2010 |
| JP | 2014158607 | 9/2014 |
| KR | 10-2019-0049502 | 5/2019 |
| WO | WO-2008100779 | 8/2008 |
| WO | WO-2010006218 | 1/2010 |
| WO | WO-2012027648 | 3/2012 |
| WO | WO-2013172935 | 11/2013 |

(56) References Cited

FOREIGN PATENT DOCUMENTS

WO     WO-2019140404     7/2019
WO     WO-2021163228     8/2021

OTHER PUBLICATIONS

Atkinson, Martin, "Anatomy for Dental Students," OUP Oxford Fourth Edition, Mar. 14, 2013, p. 298.
Caycedo et al., "Electromyographic Analysis for Silent Speech Detection," ARPN Journal of Engineering and Applied Sciences, vol. 12, No. 1 Jan. 2017, 8 pages.
Janke et al., "A Spectral Mapping Method for EMG-based Recognition of Silent Speech," In B-Interface, 2010, 10 pages.
Weaker, Frank, "Structures of the Head and Neck," F.A. Davis, Sep. 24, 2013, p. 77.
Website: CawBing: Snore Stopper Adjustable Snore Reduction Straps Anti Apnea Snore Support Belt Jaw Sleep Band Snoring Chin Strap, https://www.walmart.com/ip/Snore-Stopper-Adjustable-Snore-Reduction-Straps-Anti-Apnea-Snore-Support-Belt-Jaw-Sleep-Band-Snoring-Chin-Strap/788742945, accessed Jun. 2022, 5 pages.
Website: Halo Chinstrap by Breathwear Inc., https://www.cpap.com/productpage/breathewear-halo-chinstrap, accessed Jun. 2022, 3 pages.

\* cited by examiner

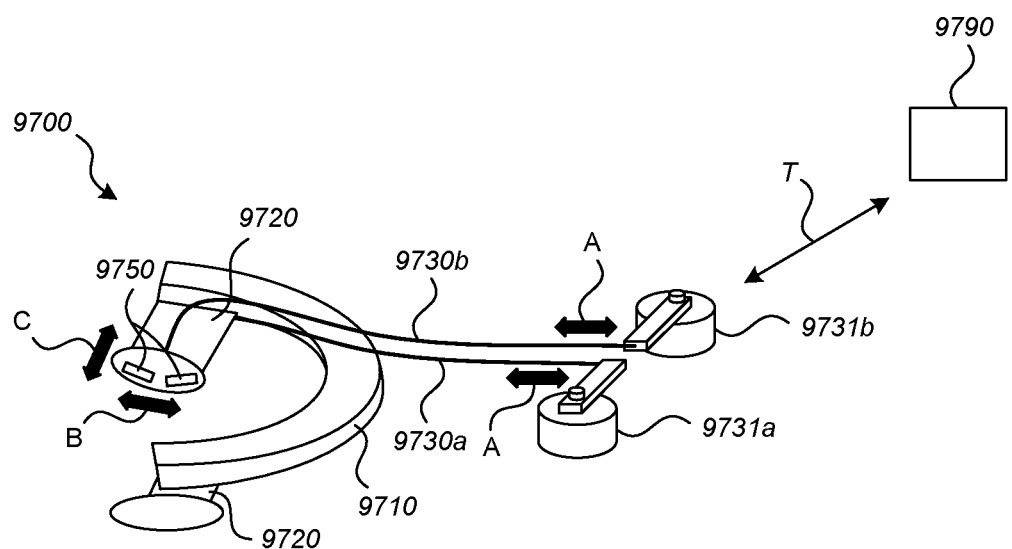
FIG. 38A
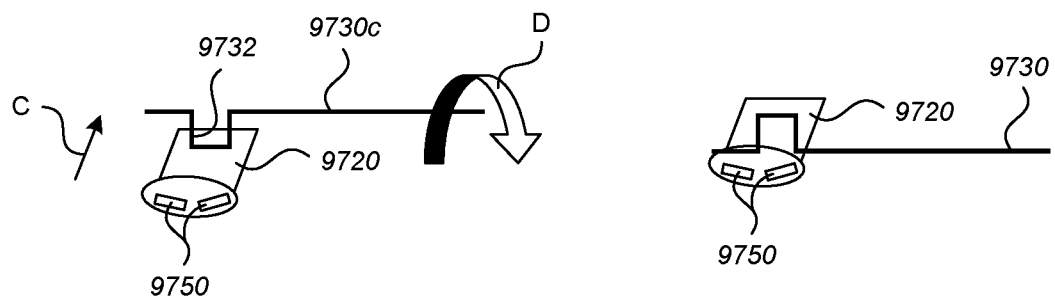
FIG. 38B  FIG. 38C

ADJUSTABLE DEVICES FOR TREATING SLEEP APNEA, AND ASSOCIATED SYSTEMS AND METHODS

CROSS-REFERENCE TO RELATED APPLICATION

The present application claims priority to U.S. provisional application No. 62/916,169, filed on Oct. 16, 2019, and incorporated herein by reference.

TECHNICAL FIELD

Representative devices and methods disclosed herein relate generally to treating obstructive sleep apnea, and in particular embodiments, to non-invasive methods and devices for treating obstructive sleep apnea, including via adjustable devices.

BACKGROUND

Obstructive sleep apnea (OSA) is a medical condition in which a patient's upper airway is occluded (partially or fully) during sleep, causing sleep arousal. Repeated occlusions of the upper airway may cause sleep fragmentation, which in turn may result in sleep deprivation, daytime tiredness, and/or malaise. More serious instances of OSA may increase the patient's risk for stroke, cardiac arrhythmias, high blood pressure, and/or other disorders.

OSA may be characterized by the tendency of soft tissues of the upper airway to collapse during sleep, thereby occluding the upper airway. OSA is typically caused by the collapse of the patient's soft palate and/or by the collapse of the patient's tongue (typically onto the back of the pharynx or into the upper airway), which in turn may obstruct normal breathing and/or cause arousal from sleep.

Some treatments have been available for OSA including, for example, surgery, constant positive airway pressure (CPAP) machines, and electrically stimulating muscles or related nerves associated with the upper airway to move the tongue (or other upper airway tissue). Surgical techniques have included tracheotomies, procedures to remove portions of a patient's tongue and/or soft palate, and other procedures that seek to prevent collapse of the tongue into the back of the pharynx. These surgical techniques are very invasive. CPAP machines seek to maintain upper airway patency by applying positive air pressure at the patient's nose and mouth. However, these machines are uncomfortable, cumbersome, and may have low compliance rates.

Some electrical stimulation techniques seek to prevent collapse of the tongue into the back of the pharynx by causing the tongue to protrude forward (e.g., in an anterior direction) during sleep. For example, U.S. Pat. No. 4,830,008 discloses an invasive technique in which electrodes are surgically implanted into a patient at locations on or near nerves that stimulate the genioglossus muscle to move the tongue forward (e.g., away from the back of the pharynx). U.S. Pat. Nos. 5,190,053 and 6,212,435 disclose electrically stimulating the genioglossus muscle to move the tongue forward in an anterior direction during apnea episodes. In another example, U.S. Pat. No. 7,711,438 discloses a non-invasive technique in which electrodes, mounted on an intraoral device, electrically stimulate the genioglossus muscle to cause the tongue to move forward during respiratory inspiration. In addition, U.S. Pat. No. 8,359,108 teaches an intraoral device that applies electrical stimulation to the hypoglossal nerve to contract the genioglossus muscle, which, as mentioned above, may prevent upper airway collapse by moving the tongue forward during sleep.

Existing techniques for electrically stimulating the hypoglossal nerve and/or the genioglossus muscle may cause discomfort, sleep arousal and/or pain, which is not desirable. Further, invasive techniques for electrically stimulating the hypoglossal nerve and/or the genioglossus muscle undesirably require surgery.

Thus, there is a need for an improved non-invasive treatment for OSA and other sleep disorders.

BRIEF DESCRIPTION OF THE DRAWINGS

Representative embodiments of the present technology are illustrated by way of example and are not intended to be limited by the Figures, where like reference numerals generally refer to corresponding parts throughout.

FIG. 38A is a schematic illustration of a device having electrodes that are movable via one or more automated actuators, in accordance with embodiments of the present technology.

FIGS. 38B and 38C illustrate the motion of a pair of electrodes in accordance with embodiments of the present technology.

DETAILED DESCRIPTION

1. Introduction

Figure 1:
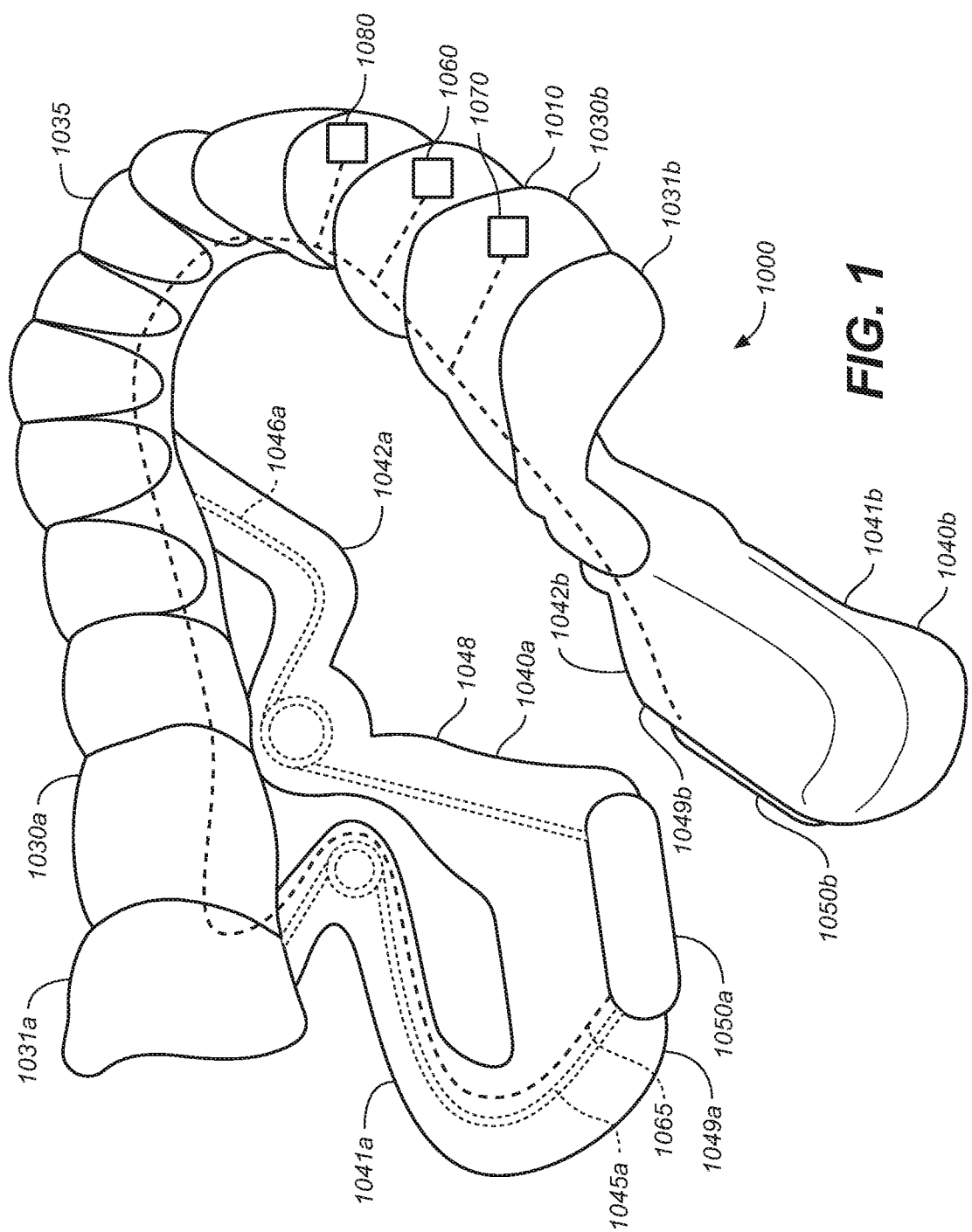
FIG. 1 is an elevated perspective view of an oral appliance configured in accordance with representative embodiments of the present technology.

Electrostimulation treatments for obstructive sleep apnea (OSA) typically involve modulating or stimulating nerves and/or muscles, e.g., to cause the tongue or other soft tissue to move in order to remove an obstruction of the upper airway, or to prevent the tongue or other soft tissue from collapsing or obstructing the airway. As used herein, the terms "modulate" and "stimulate" are used interchangeably to mean having an effect on, e.g., an excitatory effect, inhibitory effect, and/or other effect. Such stimulation may be provided to one or more nerve branches or muscles of the upper airway structures.

Representative methods and apparatuses for reducing the occurrence and/or severity of a breathing disorder, such as OSA are disclosed herein. In accordance with representative embodiments, a non-invasive and removable oral appliance provides electrical stimulation to anatomical structures of a patient's oral cavity (mouth) in a manner that improves upper airway patency and/or improves the tone of the tissue of the intraoral cavity to treat sleep apnea. An electric current generated by the appliance can stimulate at least a portion of a patient's hypoglossal nerve, genioglossus muscle and/or other nerves or muscles associated with the upper airway. By moving the tongue forward and/or by preventing a collapse of the soft tissue and/or tongue onto the back of the patient's pharynx, and/or into the upper airway, the patency or tone of the patient's upper airway can be improved in a non-invasive manner.

Non-invasive methods and apparatuses for treating a patient, for example, for sleep disorders such as OSA and/or snoring, are disclosed herein. A removeable mouthpiece or oral appliance is disclosed that is secured in the oral cavity and comprises one or more stimulation electrodes. The stimulation electrode(s) can be activated to direct electrical current through tissue in the oral cavity to stimulate nerve branches and/or muscles to improve upper airway patency or tone and/or reduce an upper airway obstruction that may contribute to sleep arousal and/or obstructive sleep apnea. The intraoral appliance can also include an electronics circuit, e.g., having a pulse generator powered by a power source such as a rechargeable battery. The stimulation in some representative embodiments, can be timed with respect to the patient's respiration to maintain upper airway patency or tone during sleep in order to reduce the occurrence of apnea events and/or sleep arousal related to upper airway obstruction and/or OSA. The appliance can also include sensors that are used to trigger the stimulation and/or to determine a response to the stimulation and/or other patient conditions. A "patient" as used herein can refer to a person using the device that may be, but is not necessarily, under the care of a physician.

A representative intraoral appliance can include flexible resilient extensions coupled to more rigid attachment structures or anchors of the intraoral appliance. The flexible resilient extensions can moveably position electrodes adjacent to target nerve branches and/or other target stimulation tissue to maintain effective contact with target structures while in use.

A further representative appliance includes elements that are deliberately made to be adjustable. This feature allows practitioners to test multiple electrode positions (and other parameters) in a reproducible manner, which in turn allows the practitioners to efficiently select electrode positions that are patient-specific and/or tailored to a particular patient's physiology and/or condition.

The following additional headings are provided for ease of readability: Heading 2: Representative Stimulation Targets (with a focus on FIGS. 29A-29D) Heading 3: Representative Appliances (with a focus on FIGS. 1-28C, and 30A-32C) Heading 4: Representative Adjustability Features (with a focus on FIGS. 33A-37C) While embodiments of the present technology are described under the selected headings indicated above, other embodiments of the technology can include elements discussed under multiple headings. Accordingly, the fact that an embodiment may be discussed under a particular heading does not necessarily limit that embodiment to only the elements discussed under that heading.

2. Representative Stimulation Targets

Representative embodiments described herein include an intraoral device that can position electrodes in a target location and/or position, e.g., adjacent a nerve and/or muscle tissue within the oral cavity, for example, as described with reference to FIGS. 29A-29D. The target location and/or position of the electrodes can be identified with respect to a patient's anatomy to direct current through tissue in a manner that provides a desired response to the stimulation. Different electrode positions or locations can be used to target different areas, anatomical structures, and/or tissue. For example, representative target locations can include a location on the tongue and/or adjacent or near nerve endings of the hypoglossal nerve and/or other nerves, with the stimulation effect of moving the tongue and/or other soft tissue to improve upper airway patency and/or improved muscle tone or stiffening. According to some representative embodiments, the target location may be within the sublingual sulcus and directed towards nerve roots that may activate the genioglossus muscle and/or the geniohyoid muscle. The target location can be identified with respect to any of, or any combination of, intrinsic or extrinsic muscles and/or associated nerve branches. Such a target location and/or position can also be distal from the salivary glands (e.g., medial to the sublingual salivary gland) and/or other structures to avoid causing pain and/or other undesired effects. According to some aspects of the present technology, such a target location and/or position can include a target angle or orientation so as to direct current to targeted nerve fibers. Location of the electrode as used herein includes an area, region or position with respect to a patient's intraoral anatomical structures, so as to direct current to tissue in a manner that causes a desired stimulation response.

While a patient is sleeping, the soft tissue of the upper airway and the tongue may move in a manner that creates an upper airway obstruction and/or reduces upper airway patency. The tongue may move, for example, while swallowing. In response to electrical stimulation, the patient's soft tissue and/or tongue also move. Accordingly, the flexible extensions of the intraoral appliance can moveably position the electrodes in a manner that accommodates such movement, while maintaining electrical contact with the target tissue to deliver therapeutic electrical stimulation.

To more fully understand the disclosed embodiments, FIGS. 29A-29D illustrate anatomical elements of a patient's upper airway (e.g., including the nasal cavity, oral cavity, and pharynx of the patient). Accordingly, FIGS. 29A-29D illustrate a number of suitable stimulation targets.

Figure 29A:
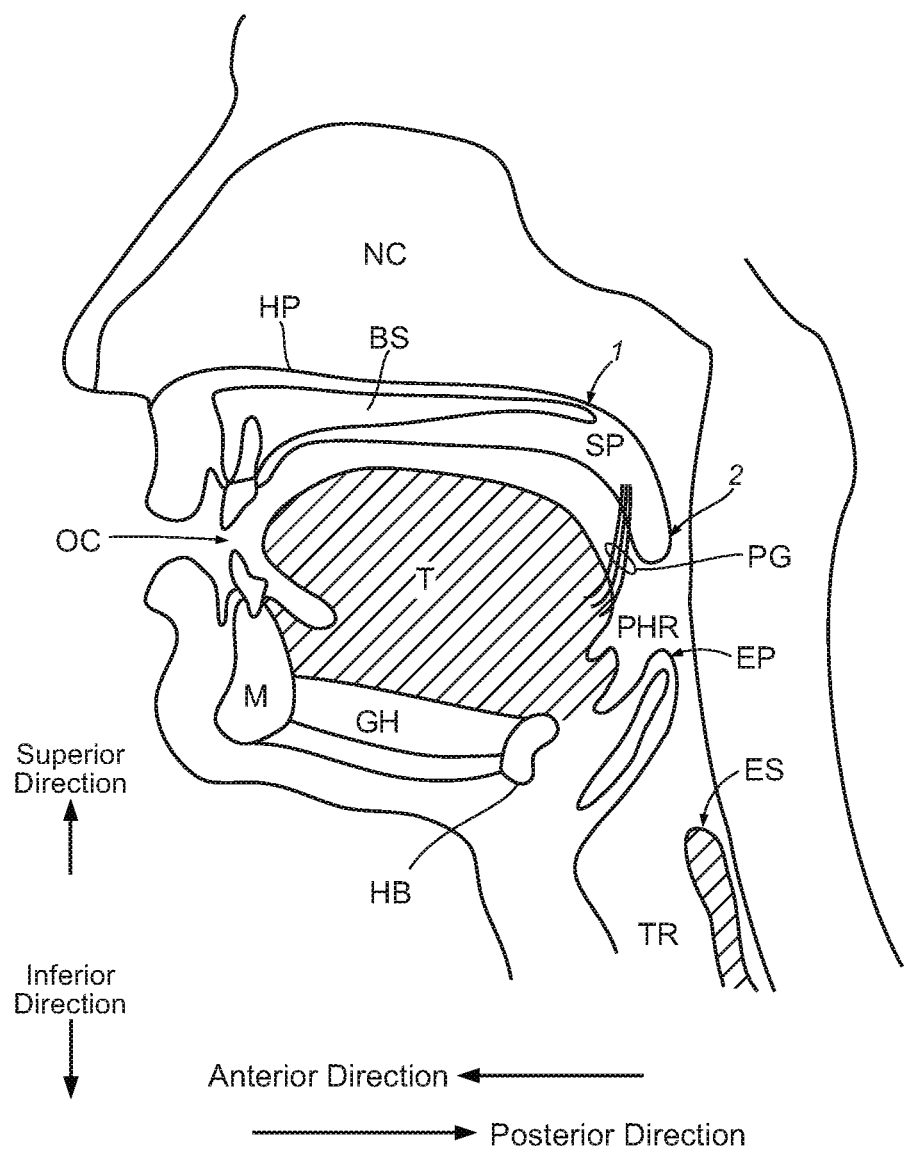
FIG. 29A is a side sectional view depicting a patient's upper airway.
Figure 29B:
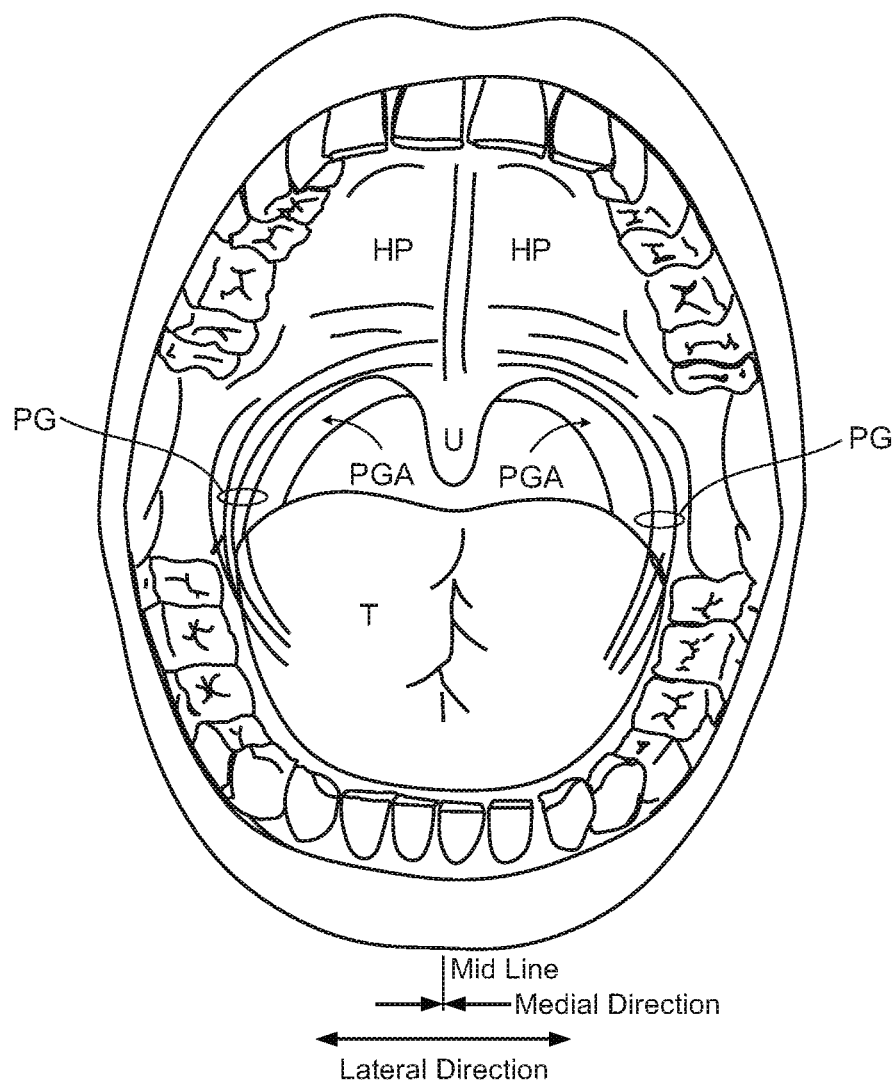
FIG. 29B is a front plan view of the patient's oral cavity.

Referring first to FIGS. 29A and 29B, the hard palate HP overlies the tongue T and forms the roof of the oral cavity OC (e.g., the mouth). The hard palate HP includes bone support BS, and thus does not typically deform during breathing. The soft palate SP, which is made of soft material such as membranes, fibrous material, fatty tissue, and muscle tissue, extends rearward (e.g., in a posterior direction) from the hard palate HP toward the back of the pharynx PHR. More specifically, an anterior end 1 of the soft palate SP is anchored to a posterior end of the hard palate HP, and a posterior end 2 of the soft palate SP is unattached. Because the soft palate SP does not contain bone or hard cartilage, the soft palate SP is flexible and may collapse onto the back of the pharynx PHR and/or flap back and forth (e.g., especially during sleep).

The pharynx PHR, which passes air from the oral cavity OC and the nasal cavity NC into the trachea TR, is the part of the throat situated inferior to (below) the nasal cavity NC, posterior to (behind) the oral cavity OC, and superior to (above) the esophagus ES. The pharynx PHR is separated from the oral cavity OC by the palatoglossal arch PGA, which runs downward on either side to the base of the tongue T. Although not shown for simplicity, the pharynx PHR includes the nasopharynx, the oropharynx, and the laryngopharynx. The nasopharynx lies between an upper surface of the soft palate SP and the wall of the throat (i.e., superior to the oral cavity OC). The oropharynx lies behind the oral cavity OC, and extends from the uvula U to the level of the hyoid bone HB. The oropharynx opens anteriorly into the oral cavity OC. The lateral wall of the oropharynx includes the palatine tonsil, and lies between the palatoglossal arch PGA and the palatopharyngeal arch. The anterior wall of the oropharynx includes the base of the tongue T and the epiglottic vallecula. The superior wall of the oropharynx includes the inferior surface of the soft palate SP and the uvula U. Because both food and air pass through the pharynx PHR, a flap of connective tissue called the epiglottis EP closes over the glottis (not shown for simplicity) when food is swallowed to prevent aspiration. The laryngopharynx is the part of the throat that connects to the esophagus ES, and lies inferior to the epiglottis EP.

Figure 29C:
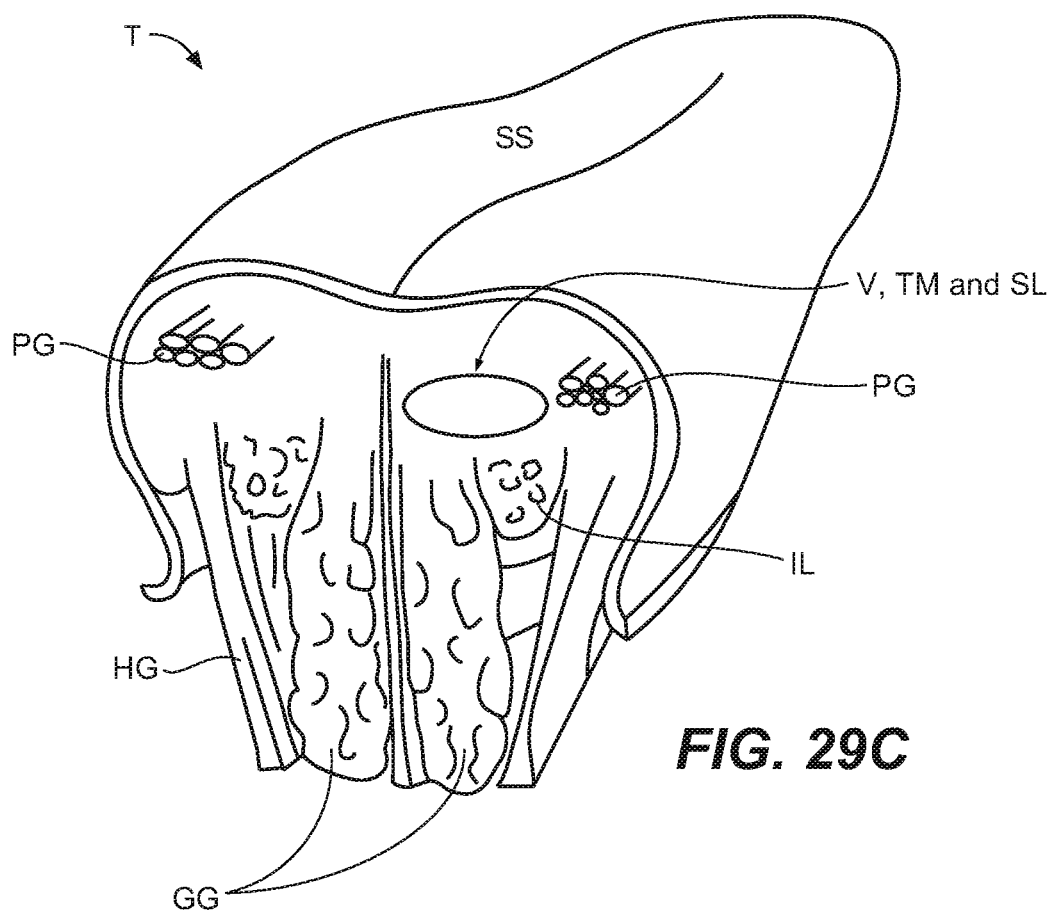
FIG. 29C is an elevated sectional view of the patient's tongue.
Figure 29D:
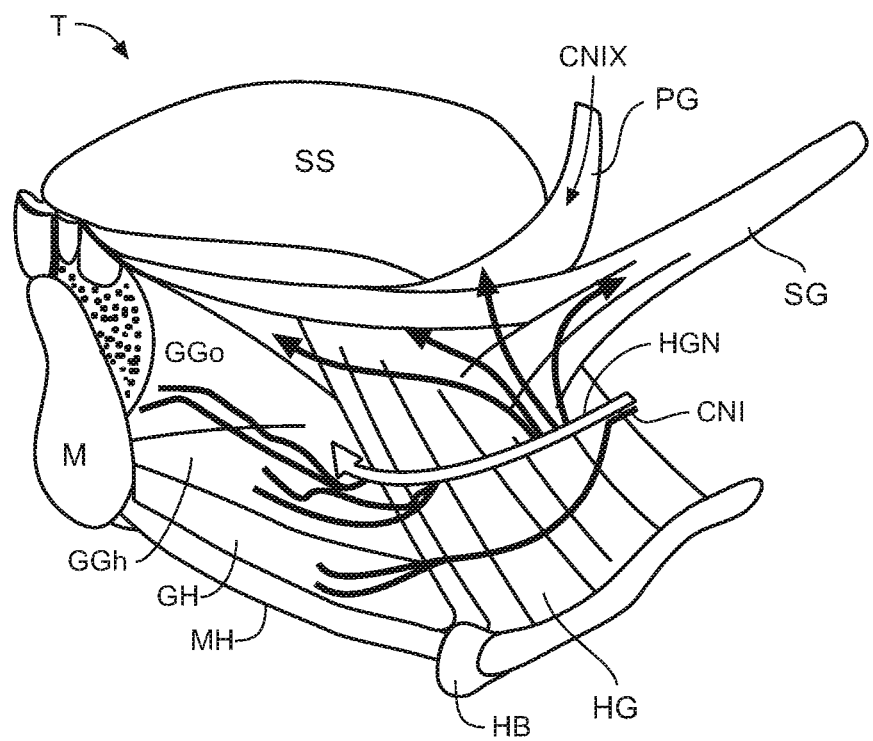
FIG. 29D is a side sectional view of the patient's tongue.

Referring also to FIGS. 29C and 29D, the tongue T includes a plurality of muscles that may be classified as either intrinsic muscles or extrinsic muscles. The intrinsic muscles, which lie entirely within the tongue T and are responsible for altering the shape of the tongue T (e.g., for talking and swallowing), include the superior longitudinal muscle SL, the inferior longitudinal muscle IL, the vertical muscle V, and the transverse muscle TM. The superior longitudinal muscle SL runs along the superior surface SS of the tongue T under the mucous membrane, and may be used to elevate, retract, and deviate the tip of the tongue T. The inferior longitudinal muscle IL lines the sides of the tongue T, and is attached to the styloglossus muscle SG. The vertical muscle V is located along the midline of the tongue T, and connects the superior and inferior longitudinal muscles together. The transverse muscle TM divides the tongue at the middle, and is attached to the mucous membranes that run along the sides of the tongue T. The intrinsic muscles are innervated by branches of the hypoglossal nerve.

The extrinsic muscles that attach the tongue T to other structures and are responsible for repositioning (e.g., moving) the tongue, include the genioglossus muscle GG, the hyoglossus muscle HG, the styloglossus muscle SG (FIG. 29D), and the palatoglossus muscle PG. The genioglossus muscle GG is made up of several muscle fibers including the horizontal fibers of the genioglossus horizontal GGh and the oblique fibers of the genioglossus oblique GGo. The genioglossus muscle GG may be used to protrude the tongue T and to depress the center of the tongue T. The genioglossus horizontal GGh connects to the mandible in the anterior, and the back of the tongue in the posterior, where it interdigitates with other muscles of the tongue. When activated, the genioglossus horizontal pulls the bulk of the tongue, including the tongue base, forward. The activation of the genioglossus horizontal GGh may also have the effect of pulling the soft palate forward. The hyoglossus muscle HG may be used to depress the tongue T. The styloglossus muscle SG may be used to elevate and retract the tongue T. The palatoglossus muscle PG may be used to depress the soft palate SP and/or to elevate the back (posterior portion) of the tongue T. The extrinsic muscles of the tongue T described above, except for the palatoglossus muscle PG, are innervated by branches of hypoglossal nerve HGN. The palatoglossus muscle PG is innervated by the pharyngeal branch of the vagus nerve (or CN IX).

The geniohyoid muscle GH, is also shown in FIG. 29D above the mylohyoid muscle MH. The geniohyoid muscle GH also connects from the mandible M to the hyoid bone HB. When the geniohyoid GH contracts, it pulls the hyoid bone HB forward and opens the lower portion of the airway including the epiglottis EP which is one of the collapsed areas in an OSA patient. The geniohyoid muscle GH is stimulated by the CNI branch of the nerve that follows the hypoglossal nerve (and can be considered to be part of the hypoglossal nerve). The mylohyoid muscle MH connects from the hyoid bone HB to the mylohyoid ridge MHR (FIG. 30B) of the mandible M.

During awake periods, the muscles of the upper airway (as well as the hypoglossal nerve) are inherently active and stimulated, and may maintain upper airway patency or tone by preventing the soft palate SP from collapsing and/or by preventing the tongue T from prolapsing onto the back of the pharynx PHR. However, during sleep periods, a relatively relaxed state of the soft palate SP may allow the soft palate SP to collapse and obstruct normal breathing, and a relatively relaxed state of the tongue T may allow the tongue T to move in a posterior direction (e.g., onto the back of the pharynx PHR) and obstruct normal breathing.

The directions and/or positions referred to herein with respect to the structures of the intraoral appliance typically refer to anatomical directions or locations when the intraoral appliance is positioned in a patient's oral cavity. The medial-lateral direction is generally the x direction as shown in various Figures herein. The posterior-anterior direction is generally the y direction as shown in various Figures herein. The superior-inferior direction is generally the z direction as shown in various Figures herein. Accordingly, the sagittal plane is the y-z plane, the coronal plane is the x-z plane and the axial plane is the x-y plane.

3. Representative Appliances

Flexible resilient extensions described herein can be used to position electrodes adjacent to and/or in electrical contact with specific locations or anatomical structures in a patient's oral cavity while permitting controlled flexibility and movement. A flexible resilient extension as used herein can, among other things, include or operate as a tether, a position stabilizer, a strut, a support and/or an electrode positioning element. The flexible resilient structure can have one or more arms extending from the attachment structure (e.g., to operate as an anchor). The flexible resilient extension can allow desired movement during use while limiting such movement to maintain the target electrode positioning. The flexible resilient extension can include one or more resilient or spring elements that permit movement of the flexible extension in anterior/posterior directions, while biasing electrodes toward the target tissue for stimulation. The flexible/resilient characteristics of the extensions can also permit the extensions to move in superior/inferior directions and/or medial/lateral directions, while biasing electrodes toward the target tissue.

The one or more flexible resilient extensions can provide controlled flexibility with respect to the angular orientation of the electrodes. The one or more flexible resilient extensions can permit electrodes to roll or rotate about the y axis while controlling or restricting such electrode movement. The one or more flexible extensions can permit the electrodes to pitch or rotate about the x axis while also controlling or restricting such electrode movement. The one or more flexible extensions can permit the electrodes to yaw or rotate about the z axis while also controlling or restricting such electrode movement.

In addition to allowing the electrode(s) to move with the patient's movements, the controlled flexibility of the extensions also allows for proper seating of the electrodes in or at a target location. For example, a representative target location includes the sublingual sulcus, which is an anatomical fold or pocket in which the electrodes may be seated. Some controlled flexibility (including, but not limited to, that with respect to the angular orientation of the electrodes) can permit or enhance positioning the electrode(s) within the sublingual sulcus. Also, the controlled flexibility of the extensions can direct moving elements of the appliance to soft tissue regions where movement occurs and away from harder tissue where moving elements can cause patient discomfort.

The flexible resilient extensions can include struts that limit linear movement in one or more directions and may also limit angular movement such as roll, pitch, yaw or any combination thereof. The flexible resilient extensions can include a resilient material and/or resilient (e.g., spring) elements. The resilient materials in some representative embodiments can be biased or can bias or control movement of the flexible resilient extensions in an inferior direction and/or in a medial direction with respect to the lateral segment to which the extension is coupled. The flexible resilient extensions, which can include resilient elements, in some representative embodiments can be biased or can bias or control movement of the flexible resilient extensions in an anterior direction or a posterior direction, depending on the electrode positioning with respect to desired target anatomical structures, and in order to direct the electrical stimulation current toward target stimulation tissue, areas or regions. In some representative embodiments, the resilient elements can bias the extensions toward an angular orientation. In some representative embodiments, the resilient elements can bias the extensions with respect to a predetermined plane, for example with respect to a sagittal plane, coronal plane, axial plane or a combination thereof. The bias of the structures may also be determined based on the desired position of orientation of the electrodes with respect to anatomical structures.

The flexible resilient extensions described herein may provide flexion points, segments, portions, axes, regions, locations, and/or areas that permit the electrodes to move (within limits) in a variety of directions, e.g., medial-lateral, anterior-posterior, superior-inferior directions, angular orientations, and/or combinations thereof. The flexible resilient extensions can include segments, portions, locations, regions, areas and/or flexion points and/or axes that have a relatively higher flexibility than that of the anchor structure (or other more rigid portions) of the attachment body. In combination, the more rigid anchor structure can be used to prevent electrode movement in particular regions while the flexible resilient extensions can allow movement in particular regions. The flexible resilient extensions may comprise some segments, portions, locations, regions, areas or flexion points or axes that have a relatively higher flexibility than that of other more rigid portions of the flexible resilient extensions. Portions of the flexible resilient extensions can be reinforced with more rigid structures and/or can have a greater material thickness to provide a stiffer or more rigid region of the flexible resilient extension. Flexible resilient extensions herein can optionally include cut-outs, notches, openings or split struts, that permit additional desired flexion of the extensions (or flexion points) and movement of the extensions or electrodes. The cut-outs, notches, openings or split structures can also allow the extensions to avoid certain anatomical structures (for example, salivary glands).

Figure 2:
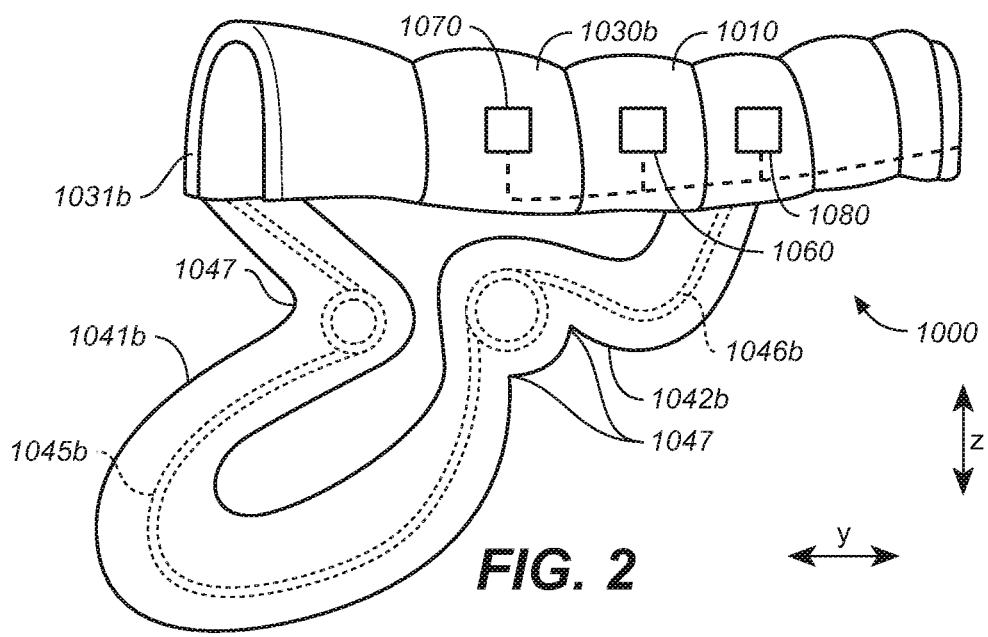
FIG. 2 is a side view of the oral appliance of FIG. 1.
Figure 3:
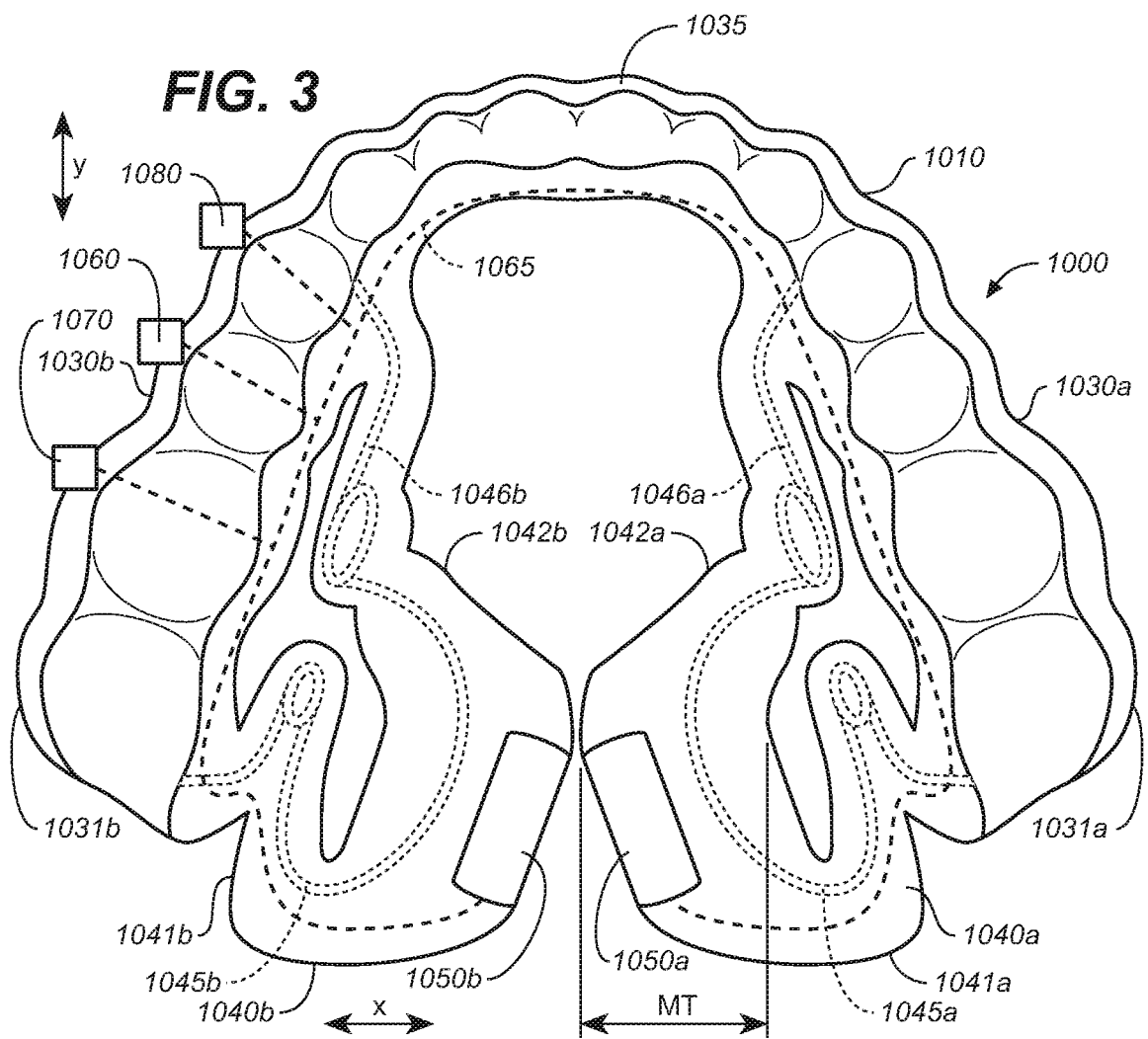
FIG. 3 is a bottom plan view of the oral appliance of FIG. 1.

FIGS. 1-3 illustrate a representative removeable intraoral appliance 1000. The intraoral appliance 1000 can include an attachment body 1010 configured to secure the intraoral appliance 1000 within an oral cavity of a patient. The attachment body 1010 can include one or more lateral portions or lateral segments 1030*a*, 1030*b*. The lateral segments 1030*a*, 1030*b*, in some representative embodiments, can be coupled to each other at a medial location of an anterior portion 1035 of the attachment body 1010, or the lateral segments can be integrally formed together. Each lateral segment 1030*a*, 1030*b*, respectively, can include a posterior, inferior molar portion 1031*a*, 1031*b* that is configured to secure the intraoral appliance 1000 to, or adjacent to, the posterior inferior molars of the patient. For example, a lateral segment can include an attachment element (e.g., an attachment structure or anchor) that is configured to attach or affix the intraoral appliance to one or more of the patient's teeth. The attachment element of the attachment body 1010 can be or can include a structure for example, that is molded or formed, in whole or in part, to fit over the patient's teeth to secure the appliance to one or more teeth. The attachment element can be positioned on only one side of the cavity or can be bilateral. The attachment element can be one of a plurality of attachment elements, e.g., one on each side of the mouth. A brace, clip, or retainer-like structure can be used to anchor the appliance to the teeth, and/or the friction between the attachment element and the teeth can provide this function. The attachment element can be rigid or can have some flexibility. In some representative embodiments, the attachment element can be more rigid than the extension member that positions an electrode in the oral cavity, so as to anchor at least part of the attachment element relatively immovably within the oral cavity. The attachment element may or may not be customized for an individual patient, depending on the implementation.

Flexible, resilient extensions (also referred to herein as extension members) 1040*a* and 1040*b* are respectively coupled to the lateral segments 1030*a* and 1030*b* at the respective posterior molar portions 1031*a*, 1031*b* of the attachment body 1010. The flexible resilient extensions 1040*a*, 1040*b* extend inferior and medial of the lateral segments 1030*a*, 1030*b*. The flexible resilient extensions 1040*a*, 1040*b* can comprise a soft or relatively lower durometer material (e.g., lower than the lateral segments 1030*a*, 1030*b*), forming a tissue interface portion 1048.

The flexible resilient extensions 1040*a*, 1040*b* can each include a posterior arm 1041*a*, 1041*b* and an anterior arm 1042*a*, 1042*b*. The posterior arms 1041*a*, 1041*b* are coupled to the corresponding posterior molar portions 1031*a*, 1031*b* of the lateral segments 1030*a*, 1030*b*. The anterior arms 1042*a*, 1042*b* are coupled to the attachment body 1010 at a position anterior to the posterior arms 1041*a*, 1041*b*. The flexible resilient extensions 1040*a*, 1040*b* can include a plurality of bends, curves notches or other flexion points 1047 that permit flexion and/or operate to relieve stress on the extension when experiencing movement within the oral cavity. The arms can also include or can operate as struts to provide structural support and/or as tethers to restrict movement.

Electrodes 1050*a*, 1050*b* are coupled to the corresponding extensions 1040*a*, 1040*b* at inferior-medial ends 1049*a*, 1049*b* of the extensions where the posterior arms 1041*a*, 1041*b* join the anterior arms 1042*a*, 1042*b*. The posterior arms 1041*a*, 1041*b* couple the respective electrodes 1050*a*, 1050*b* to the respective posterior molar portions 1031*a*, 1031*b* of the corresponding lateral segments 1030*a*, 1030*b*. The anterior arms 1042*a*, 1042*b* also couple the electrodes 1050*a*, 1050*b* to the lateral portions 1030*a*, 1030*b*.

The medial ends 1049*a*, 1049*b* are sized to have a medial thickness (MT, shown in FIG. 3) that fills a medial-lateral space under a patient's tongue to limit and/or reduce medial-lateral movement of the electrodes 1050*a*, 1050*b* when positioned in the oral cavity.

As shown in FIGS. 1-3, first resilient elements (e.g., springs) 1045*a*, 1045*b* can be incorporated into the posterior arms 1041*a*, 1041*b*. They can be attached, encased or otherwise integrated with the flexible resilient extensions 1040*a*, 1040*b*. Second resilient elements 1046*a*, 1046*b* are respectively incorporated into the anterior arms 1042*a*, 1042*b*. Any of the foregoing resilient elements can bias the extensions 1040*a*, 1040*b* in a variety of directions in order to direct the electrodes toward contact with the target stimulation tissue, areas or regions. For example, the extensions can be biased in a medial, inferior and/or posterior direction. In some representative embodiments, the resilient elements can bias the extensions to or toward an angular orientation, for example, with respect to a predetermined plane, including but not limited to, with respect to a sagittal plane, coronal plane or medial plane or a combination thereof. The first resilient elements 1045*a*, 1045*b* can bias the posterior arms so that the attached electrode contacts tissue for stimulation. Likewise, the second resilient elements 1046*a*, 1046*b* can bias the anterior arms so that the attached electrode contacts tissue at the target location. In some representative embodiments, the second resilient elements 1046*a*, 1046*b* can be configured to bias the extensions 1040*a*, 1040*b* in a posterior direction so that if the tongue moves forward and pushes the extensions 1040*a*, 1040*b* forward, the extensions 1040*a*, 1040*b* will tend to move posteriorly toward their original positions.

The extensions 1040*a*, 1040*b* can be configured to be more rigid in one direction than another. For example, the flexible extensions 1040*a*, 1040*b* can be relatively more rigid in a medial-lateral direction than in the anterior-posterior direction. Such a configuration can provide more consistent tissue contact and direction of current flow by allowing more movement in the anterior-posterior directions when the tongue moves forward and back while maintaining contact against tissue at a target location. In some representative embodiments, the flexible extensions 1040*a*, 1040*b* can also be relatively more rigid in a medial-lateral direction than in an inferior-superior direction. In some representative embodiments, the flexible extensions 1040*a*, 1040*b* can also be relatively more rigid in an inferior-superior direction than in an anterior-posterior direction.

The posterior arms 1041*a*, 1041*b* and the anterior arms 1042*a*, 1042*b* together can guide, limit and/or control the movement of the electrodes 1050*a*, 1050*b* while the electrodes are positioned in the oral cavity of a patient. Accordingly, the extensions 1040*a*, 1040*b*, the posterior arms 1041*a*, 1041*b* and the anterior arms 1042*a*, 1042*b* can position the electrodes 1050*a*, 1050*b* at a target location with respect to the patient's anatomy to direct current through tissue to provide a desired stimulation response.

According to representative embodiments, the posterior arms 1041*a* 1041*b* can limit movement in an anterior direction while the anterior arms 1042*a*, 1042*b* can limit movement in a posterior direction. The arms can also limit angular movement such as roll, pitch, yaw or any combination thereof. Thus, the extensions can allow movement, for example of the tongue and surrounding soft tissue, and the electrodes within the oral cavity, while allowing but limiting and controlling the movement of the extensions 1040*a*, 1040*b* and therefore the electrode position.

The electrodes 1050*a*, 1050*b* are shown oriented at approximately 45 degrees with respect to a sagittal plane (or a y-z plane, as described later with reference to FIGS. 28A-28C). However, the electrodes can be oriented at other angles, as is also described in more detail later. The orientation of the electrode angle shown or described herein, in some representative embodiments is an "original angle", i.e., the angle that the electrode is at prior to being positioned in the oral cavity. When positioned in the oral cavity, the angle may change due to contact between the appliance 1000 and the anatomical features of a patient's oral cavity. However, in representative embodiments, the electrodes are biased toward the original angular orientation.

Figure 20:
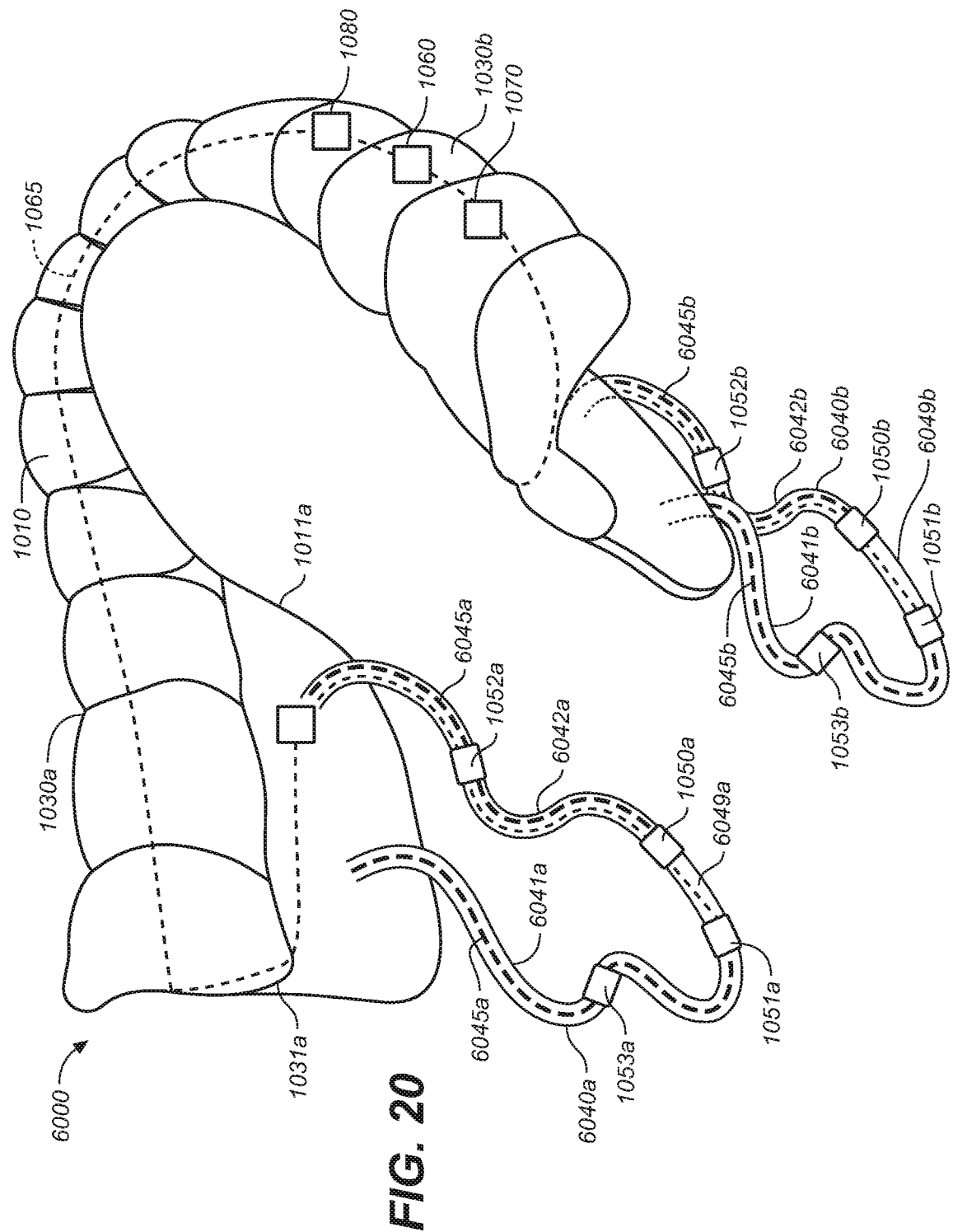
FIG. 20 is an elevated perspective view of an oral appliance configured in accordance with representative embodiments of the present technology.
Figure 21:
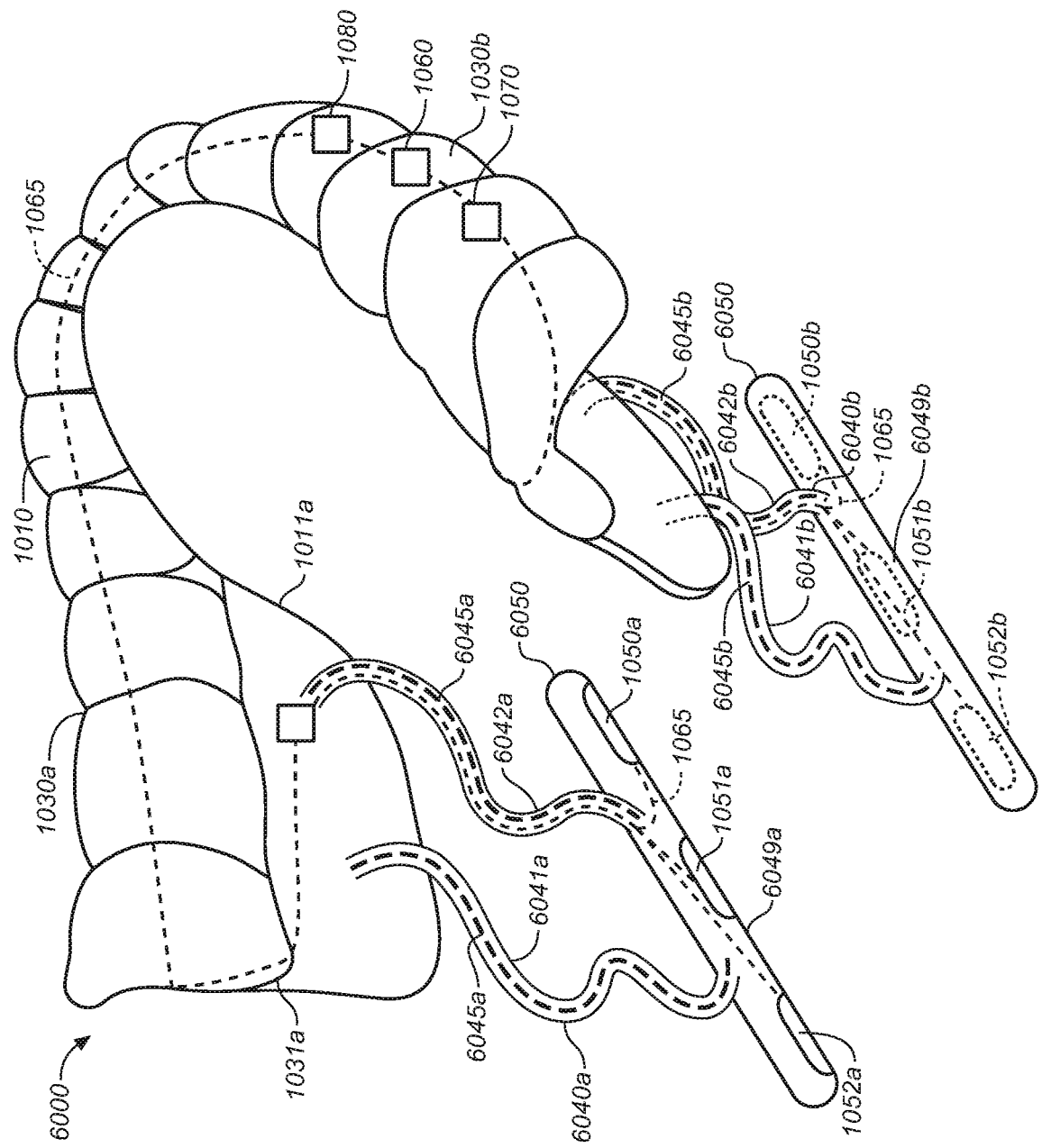
FIG. 21 an elevated perspective view of an oral appliance configured in accordance with representative embodiments of the present technology.
Figure 27:
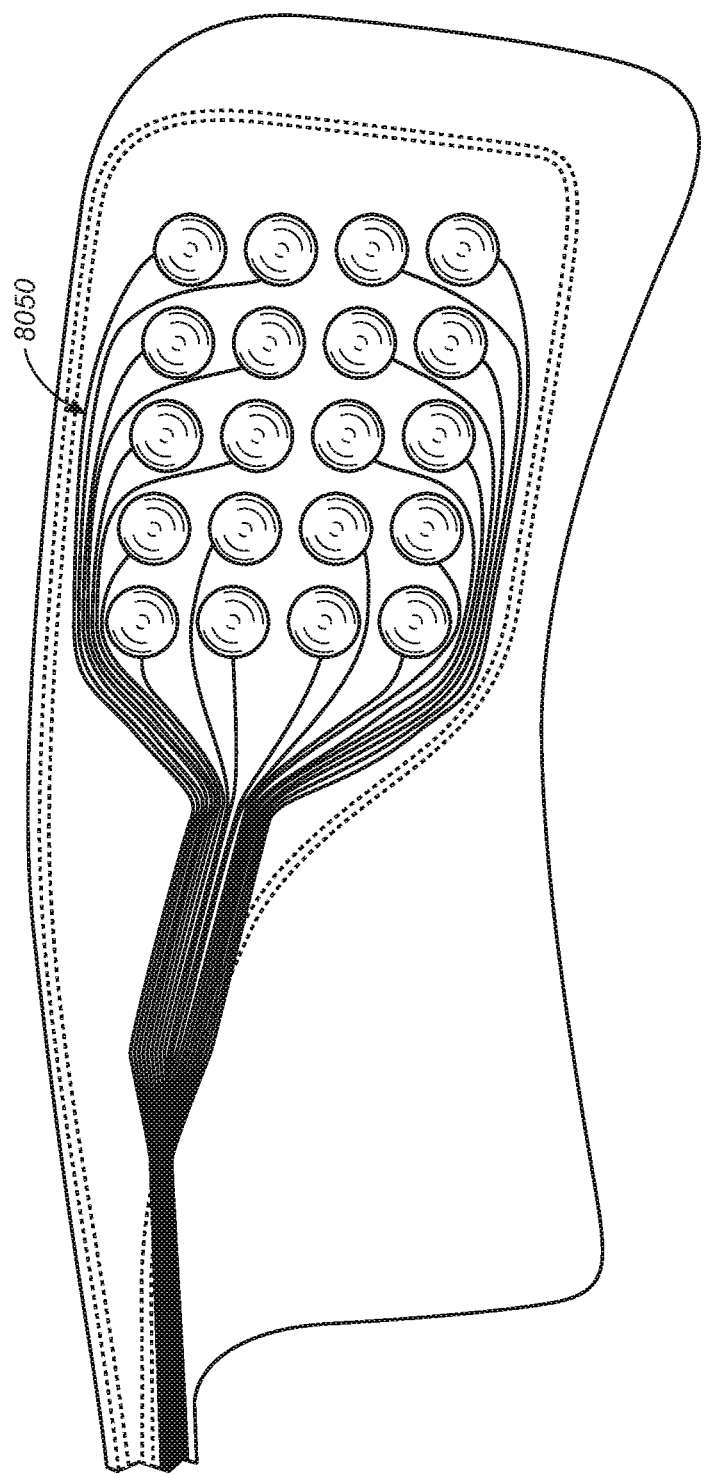
FIG. 27 is a side view of an electrode array of an oral appliance configured in accordance with representative embodiments of the present technology.

The electrodes 1050*a*, 1050*b* can have a variety of suitable shapes and/or sizes. The electrodes can include flat or rounded portions or arced surfaces to enhance (e.g., optimize) tissue contact and stimulation response. The electrodes 1050*a*, 1050*b* can include a single electrode carried by each lateral segment 1030*a*, 1030*b*, or a plurality of electrodes (e.g., an array) that may be selected (individually or as a set or subset) for a target stimulation response. FIGS. 20, 21, and 27, described in further detail later, illustrate representative arrays.

In some embodiments, the intraoral appliance 1000 is customized to fit a particular patient's oral cavity. For example, the elements forming the appliance 1000 can be specifically sized and/or shaped to provide tissue contact at a particular patient's anatomical location, and/or in a location that is identified to provide a desired therapeutic response in a particular patient. The intraoral appliance can be further customized to provide more efficient and/or better-directed electrical stimulation to the oral cavity tissue of an individual patient. The customized attachment body can be constructed from a mold, or can be 3D printed to conform or fit on one or more inferior teeth of the particular patient, accounting for the particular patient's bite.

The attachment bodies described herein with respect to the various Figures can be constructed from a variety of suitable materials, including ethylene vinyl acetate, polycarbonate, nylon, and/or other thermoplastics. The soft or relatively low durometer material forming the tissue interfaces described herein can include, for example, a silicone, urethane, polyurethane, and/or polyurethane foam. The flexible resilient structures described herein can include an elastic material, a resilient material, and/or a spring material such as, for example, stainless steel, nitinol and/or a combination of materials having suitable flexibilities and rigidities. In addition, the flexible resilient structures can have a varying flexibility and/or other mechanical properties, along the length of the structures. The resilient elements can be incorporated into the extensions in a number of manners including but not limited to being embedded in, attached or otherwise coupled to, injected into, or otherwise formed with the extensions. In some embodiments, a low durometer material is combined with a resilient structure, material or spring element or material to provide a soft exterior or tissue interface.

A practitioner or manufacturer can identify a predetermined electrode position to target a particular tissue or tissue region in the patient's oral cavity. In some embodiments, a customized device can then target such tissue, with the customized parameters including but not limited to, electrode position, electrode angle, extension dimensions, strut dimensions, flexion point locations and/or flexion directions. Such customized device parameters can be based on a preliminary test of the patient's response to various stimulation parameters, device geometry parameters, and/or the patient's own particular anatomy. As described in more detail with respect to FIGS. 33A to 37C herein, a test device may be used to preliminarily test a patient's response to various stimulation parameters, device geometry patterns and/or material properties (e.g., flexibility and resilience), and/or electrode positions.

As shown in FIGS. 1-3, the intraoral appliance can further include an electronics circuit 1060 (shown schematically) optionally including a pulse generator, logic circuitry and/or a controller. The electronics circuit is electrically coupled by way of one or more electrical connections 1065 (e.g., wires) to one or more electrodes 1050a, 1050b (also referred to herein with reference numbers 1051a, 1051b) and configured to deliver electrical stimulation through tissue within the oral cavity of a patient.

The intraoral appliance 1000 can further include a sensor 1070 configured to sense biometric information corresponding to one or more patient parameters including, but not limited to, respiration parameters (e.g., inhalation and exhalation cycles/waveforms), sleep arousal, pulse oxygen, oxygen saturation, heart rate, body temperature, stimulation response parameters, apnea events, body position, jaw, tongue, soft tissue movement or position, and/or other patient movement or position, tongue location, location of tongue with respect to mouthpiece, nose breathing versus mouth breathing, detection of when in a breathing cycle mouth versus nose breathing occurs, detection of rescue breaths, and/or other parameters indicative of conditions of the patient or the patient's upper airway/oral cavity. Sensors, for example, can include but are not limited to, temperature sensors such as thermistors and/or thermocouples, sound sensors, vibration sensors, pressure sensors, force sensors, strain gauges, magnetometers, accelerometers, gyroscopes, impedance sensors, EMG sensors, gas sensors and/or chemical sensors, oxygen saturation sensors, and/or other sensors that can sense conditions of the patient. In some representative embodiments, the patient's respiration parameters can be used to trigger stimulation based on the patient's breathing cycle as well as information that may indicate an apnea event is occurring or is likely to occur.

This information obtained from the sensor(s) can be used to determine when to stimulate. For example, electrical stimulation can be provided to the patient immediately prior to inhalation to ensure upper airway patency or tone during inhalation. Stimulation can be provided at other times as well, for example at the end of exhalation and into an inhalation cycle, or when an apnea event is detected. Stimulation can also be triggered by other parameters. In some representative embodiments, for example, stimulation can be triggered by sensing tongue position or movement. Stimulation can also be generally constant, e.g., always on. When on, the applied electrical current can be applied to different electrodes, e.g., in a repeated cycle.

Sensors can also be used to detect the patient's response to stimulation and can be used to adjust the stimulation parameters, including which electrode(s) are active at any particular time. EMG sensors can also be used to sense muscle contraction or force to determine the patient's response to stimulation. Impedance sensors on the mouthpiece can sense the location of the tongue with respect to the mouthpiece, extension or electrodes. In addition to or in lieu of the foregoing functions, one or more sensors can be used to determine system performance, electrode/tissue contact and/or effectiveness, and/or movement of the electrodes and/or extensions coupled to the electrodes.

The overall system can include logic circuitry to control one or more aspects of the electrical stimulation provided to the patient via the intraoral appliance. The logic circuitry can be programmed to determine or select target stimulation parameters, to assess the patient's response to the stimulation, to select a stimulation protocol (e.g., including which electrodes are active, and when), to use sensed information to initiate, adjust, modify and/or cease stimulation, and/or to transmit, receive and/or record data related to treatment or patient condition or related stimulation parameters. A power source, e.g., a battery 1080 can provide power to the pulse generator, sensors, controller and/or logic circuits and can be replaceable or rechargeable. One or more electrodes described herein can be used to sense information from within the patient's oral cavity such as, for example, via EMG or detecting NCV (nerve conduction velocity), or for detecting impedance. The logic circuit can include a controller programmed with a logic program configured to receive input from the sensor(s) and to control the stimulation delivered to the patient in response to one or more logic conditions.

Various representative embodiments throughout this application may be shown with elements having the same or similar reference numbers as elements that are described in FIGS. 1-3 or other Figures, and accordingly can have the same or generally the same characteristics and operation as described with reference to FIGS. 1-3 or such other Figures.

Figure 4:
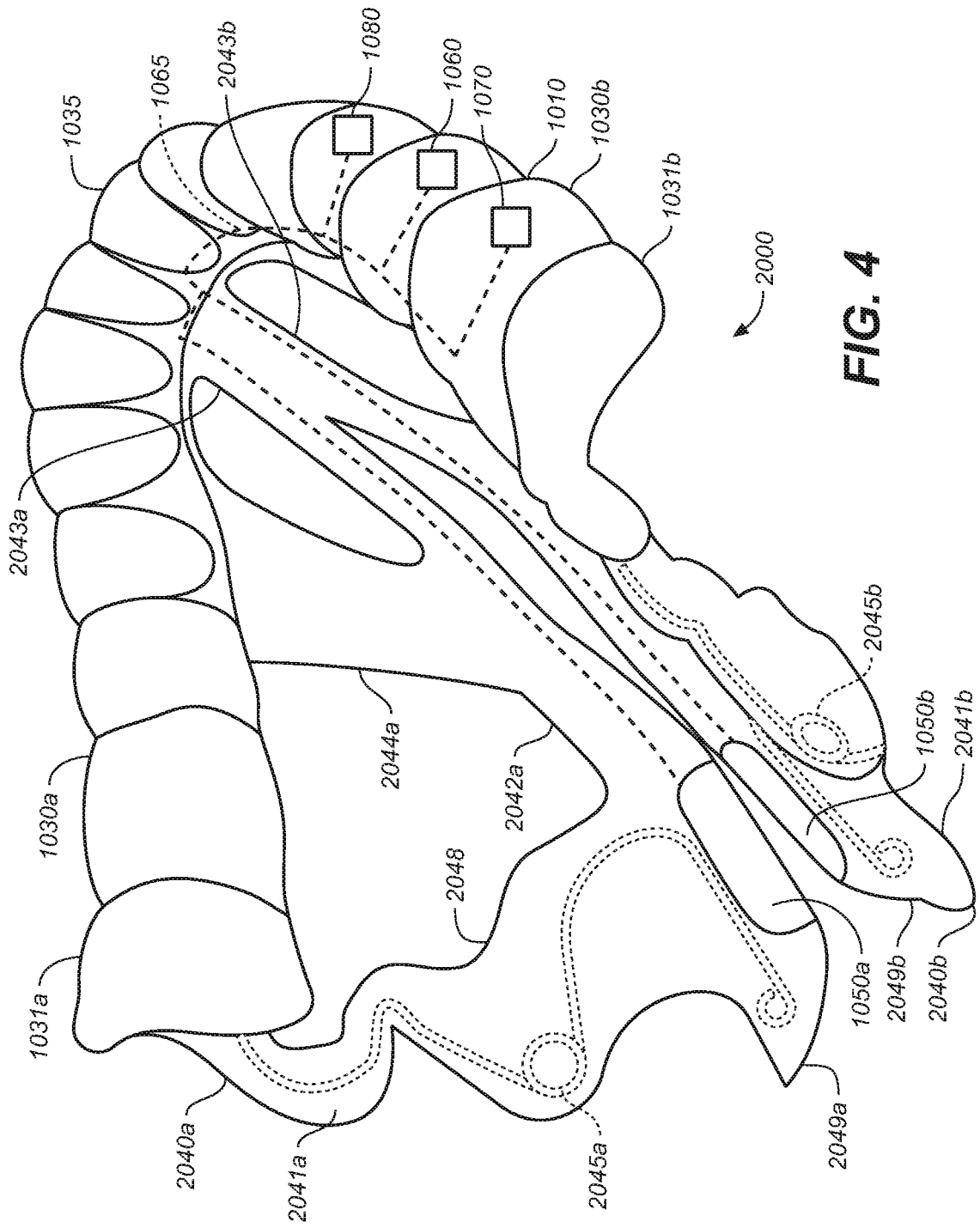
FIG. 4 is an elevated perspective view of an oral appliance configured in accordance with representative embodiments of the present technology.
Figure 5:
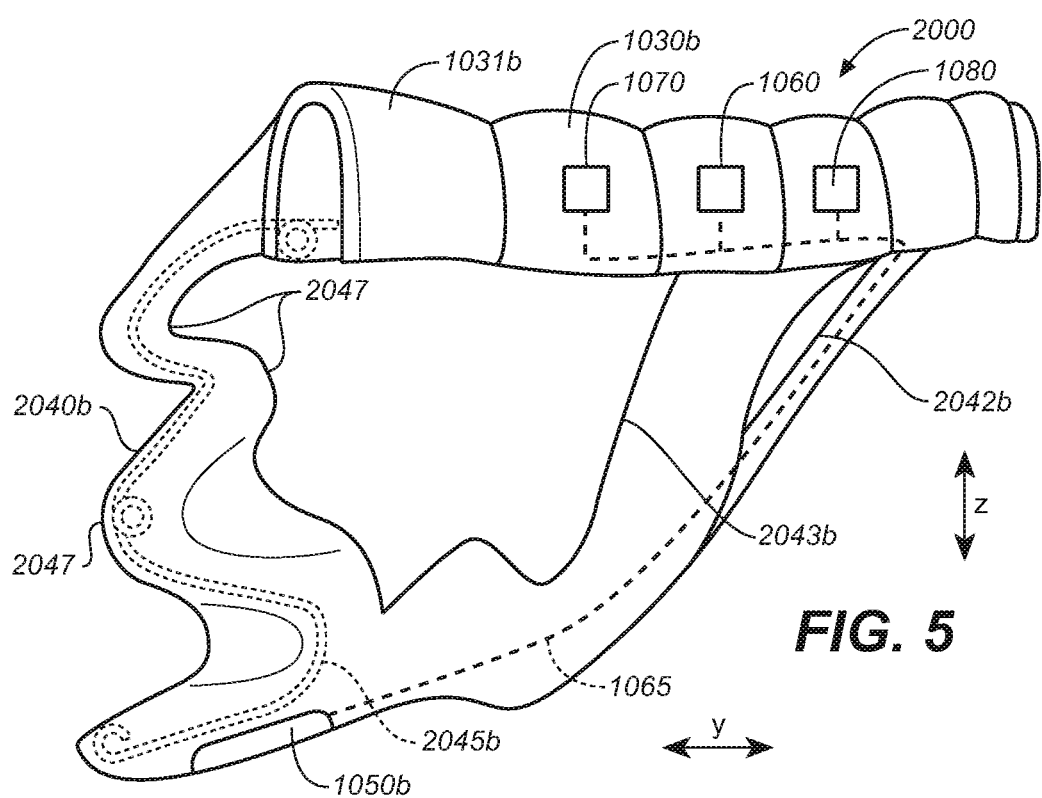
FIG. 5 is a side view of the oral appliance of FIG. 4.
Figure 6:
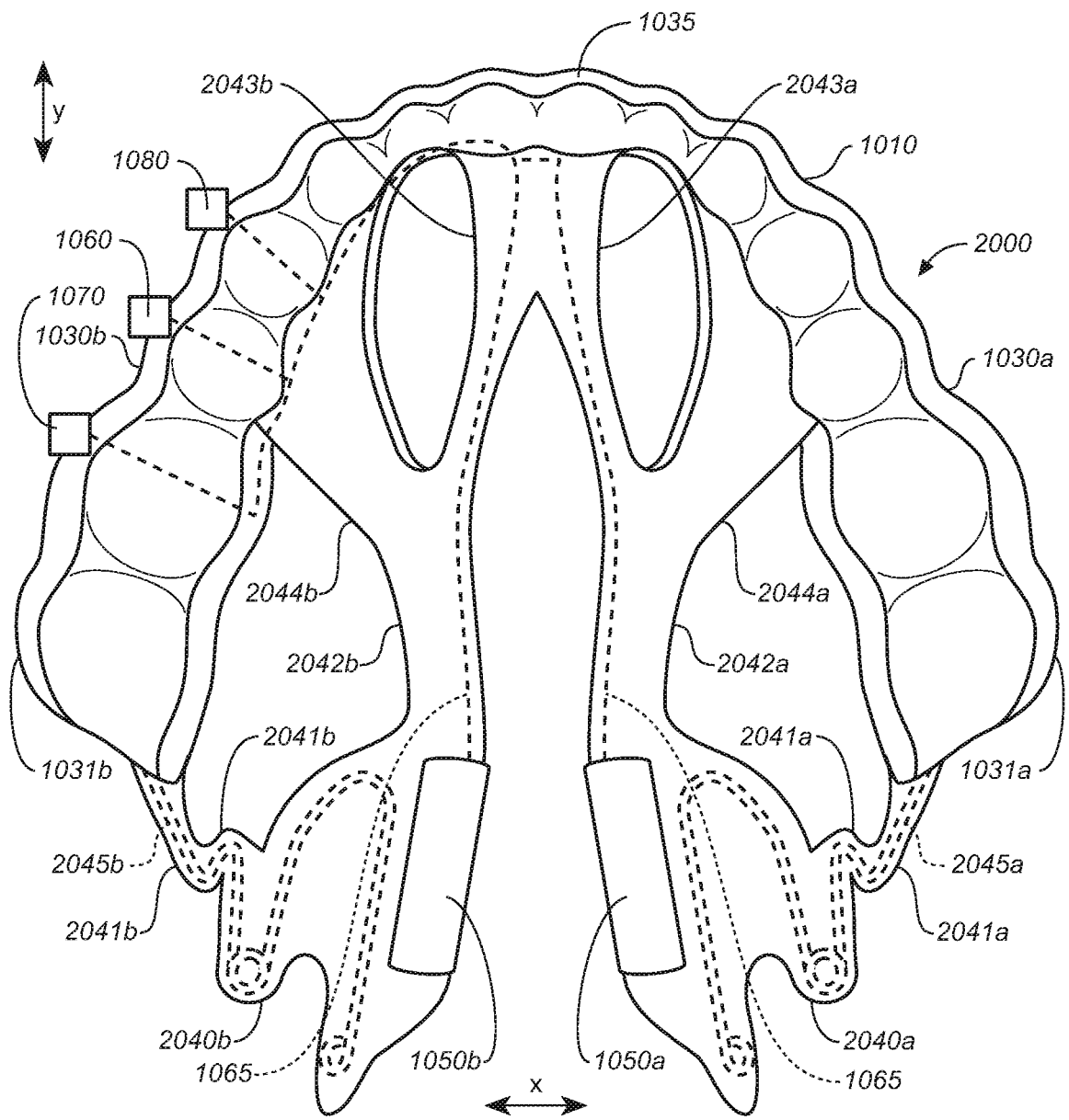
FIG. 6 is a bottom plan view of the oral appliance of FIG. 4.

FIGS. 4-6 illustrate a removeable intraoral appliance 2000 configured in accordance with some embodiments of the present technology. The intraoral appliance 2000 includes an attachment body 1010. Flexible, resilient extensions 2040a and 2040b are respectively coupled to the corresponding lateral segments 1030a and 1030b at the corresponding posterior molar portions 1031a, 1031b of the attachment body 1010. The flexible resilient extensions 2040a, 2040b can extend inferior and medial of the lateral segments 1030a, 1030b. The flexible resilient extensions 2040a, 2040b can include a patient interface portion 2048 that includes a relatively lower durometer material. The flexible resilient extensions 2040a, 2040b comprise a plurality of bends, curves, notches or other flexion points 2047.

The flexible resilient extensions 2040a, 2040b can each include a posterior arm 2041a, 2041b and an anterior arm 2042a, 2042b. The posterior arms 2041a, 2041b are coupled to posterior molar portions 1031a, 1031b of the lateral segments 1030a, 1030b. The anterior arms 2042a, 2042b are coupled to the attachment body 1010 at a location anterior to the posterior arms 2041a, 2041b. The anterior arms 2042a and 2042b can include anterior branches 2043a, 2043b and lateral branches 2044a, 2044b, respectively. The anterior branches 2043a, 2043b are attached to the anterior segment or location 1035 in a location anterior to the posterior molar portions 1031a, 1031b. The anterior branches 2043a, 2043b can also be attached to each other. The lateral branches 2044a, 2044b connect the anterior arms 2042a, 2042b to the lateral segments 1030a, 1030b.

Electrodes 1050a, 1050b are coupled to the corresponding extensions 2040a, 2040b at the inferior-medial ends 2049a, 2049b where the posterior arms 2041a, 2041b and anterior arms 2042a, 2042b are coupled together. As shown in FIGS. 4-6, the resilient elements 2045a, 2045b are incorporated into the posterior arms 2041a, 2041b. The resilient elements can bias the extensions 2040a, 2040b in one or more directions (e.g., medial/lateral, inferior/superior, anterior/posterior directions and/or toward an angular orientation) in order to direct the electrodes toward the target stimulation tissue, areas and/or regions. Extensions 2040a, 2040b may be configured to be more rigid in one direction versus another or to have more permitted motion in one direction versus another.

As further illustrated, the anterior arms 2042a, 2042b do not include resilient elements similar to the resilient elements 2045a, 2045b carried by the posterior arms 2041a, 2041b. The anterior arms 2042a, 2042b are less bulky than the anterior arms of FIGS. 1-3 because they do not include an encased spring member and are accordingly more comfortable to the patient. While the anterior arms 2042a, 2042b do not include spring elements that bias the anterior arms 2042a, 2042b in a posterior direction, they operate as tethers or stabilizers that prevent twisting or other undesired movement (rotational, medial-lateral, inferior-superior and/or superior inferior movement) of the posterior arms 2040a, 2040b and the attached electrodes 1050a, 1050b. The anterior arms 2042a, 2042b in representative embodiments can instead or in addition, include additional spring elements.

The anterior arms 2042a, 2042b each have multiple attachment points (i.e., with anterior branches 2043a, 2043b and lateral branches 2044a, 2044b) to the body 1010 with different locations and orientations that, in combination, resist movement in multiple directions. Connecting the anterior branches 2043a, 2043b of the extension members to the anterior location 1035 of the body can keep the electrodes closer to the frenulum. Connecting the anterior arms 2042a, 2042b together can maintain similar posterior-anterior positions of the electrodes 1050a, 1050b with respect to each other. While increasing control of electrode position and movement, connecting the branches 2042a, 2042b at the anterior location 1035 may prevent posterior movement of the electrodes, such movement which may be desirable to maintain electrode contact when the tongue moves. Additionally, while increasing control of electrode movement, the multiple branches of the anterior arms can increase the number of device contact points under a subject's tongue which may reduce comfort. Such multiple attachment point elements can be further useful in customized devices where anatomical structure of an individual patient may be identified and avoided for patient comfort using a more customized device construction.

In some representative embodiments, the anterior arms 2042a, 2042b can be constructed of a material with resilient properties that allow the arms to more elastically restrain electrode movement. Although not shown, in some representative embodiments resilient elements (e.g., similar to elements 2045a, 2045b) may be included in the anterior arms 2042a, 2042b to provide additional spring bias or structural rigidity in a manner similar to FIGS. 1-3, e.g., if comfortable for the patient and/or required for suitable electrode placement.

Figure 7:
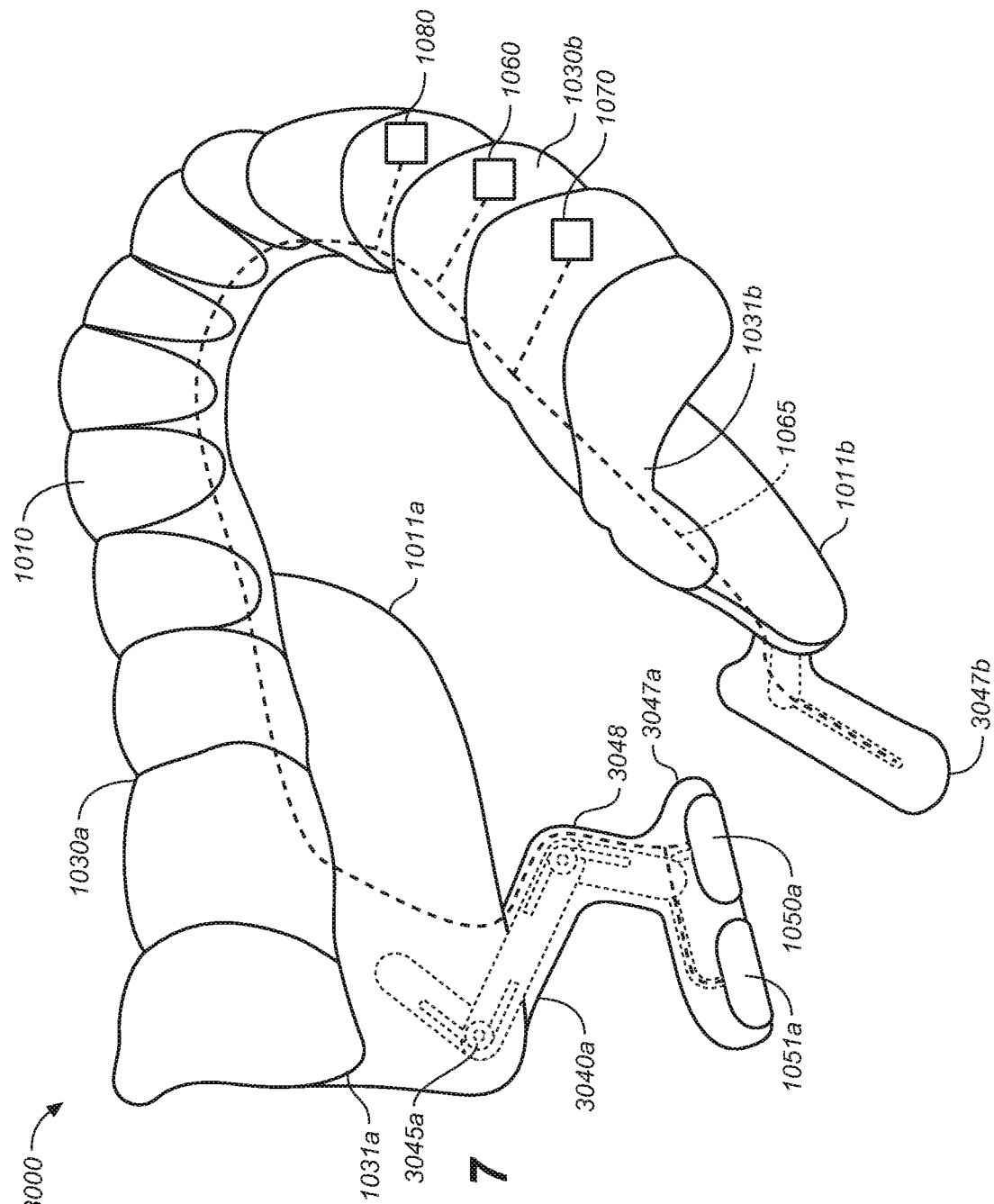
FIG. 7 is an elevated perspective view of an oral appliance configured in accordance with representative embodiments of the present technology.
Figure 8:
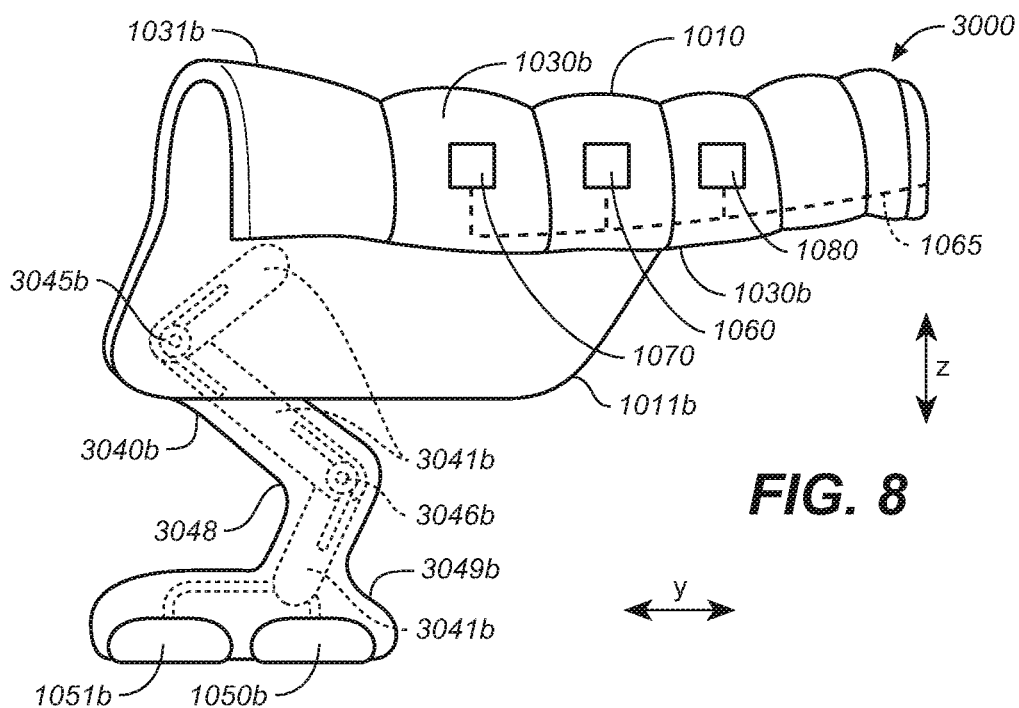
FIG. 8 is a side view of the oral appliance of FIG. 7.
Figure 9:
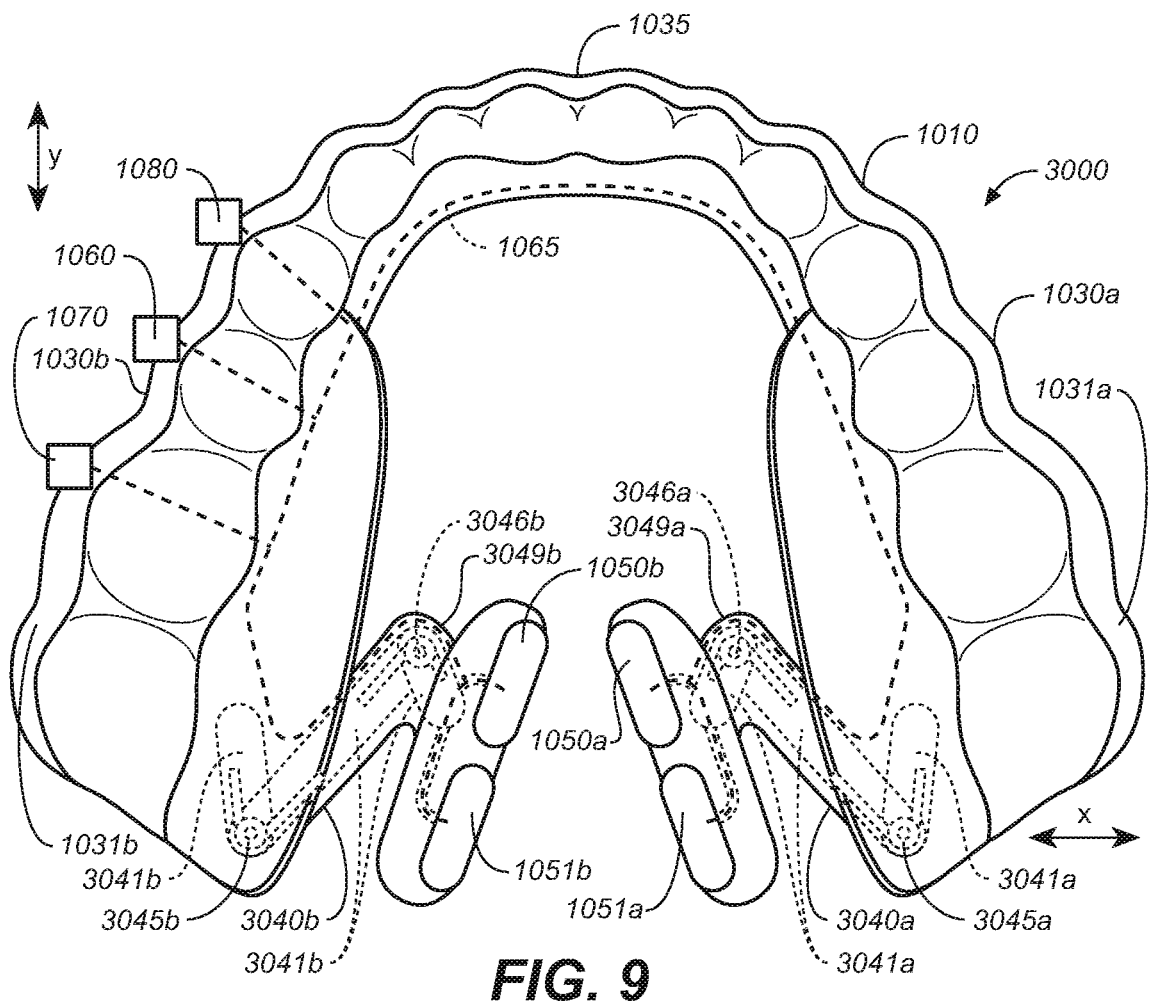
FIG. 9 is a bottom plan view of the oral appliance of FIG. 7.

FIGS. 7-9 illustrate another representative removeable intraoral appliance 3000 that includes extensions 3040a, 3040b having an arrangement of flexibly linked rigid segments. In addition, the mouthpiece body 1010 includes inferiorly extending, posterior rigid flaps (or wings) 1011a, 1011b. (See also FIGS. 28A and 30B). The posterior rigid flaps 1011a, 1011b extend in an inferior direction from corresponding posterior molar portions 1031a, 1031b. The flexible, resilient extensions 3040a and 3040b are coupled to corresponding posterior rigid flaps 1011a, 1011b.

In a further aspect of the arrangement shown in FIGS. 7-9, the flexible resilient extensions 3040a, 3040b include a single arm with a plurality of more rigid segments 3041a, 3041b joined by resilient connectors 3045a, 3045b and 3046a, 3046b. The rigid segments 3041a, 3041b and resilient connectors 3045a, 3045b, 3046a, 3046b may be attached, encased or otherwise integrated with the flexible extension structure. For example, the rigid segments 3041a, 3041b and resilient connectors 3045a, 3045b, 3046a, 3046b may be covered with a patient interface portion 3048 that comprises a relatively lower durometer material. The flexible resilient extensions 3040a, 3040b provide a single attachment location to the body 1010.

In a representative arrangement, each extension 3040a, 3040b includes a corresponding plurality of electrodes 1050a, 1051a and 1050b, 1051b coupled to its distal (inferior) end. For example, first electrodes 1050a, 1051a are positioned on one electrode support 3047a which is coupled to the inferior end 3049a of a first extension 3040a, and second electrodes 1050b, 1051b are positioned on another electrode support 3047b which is coupled to the inferior end 3049b of extension 3040b.

The resilient connectors (e.g., springs or other suitable structures) can bias the extensions 3040a, 3040b in a medial/lateral, inferior/superior, and/or anterior/posterior direction, and/or toward an angular orientation, so as to direct the electrodes towards target stimulation tissue, areas or regions. Each connector may move in a different direction and have a different flexibility. The rigid elements 3041a, 3041b can be more rigid than the resilient connectors 3045a, 3045b, 3046a, 3046b. The rigid elements 3041a, 3041b can provide segments of support to the extension members while the resilient connectors 3045a, 3045b, 3046a, 3046b provide flexion points between segments, regions, portions, areas, or locations of the device. The multiple connectors can allow specifically directed or biased movement while the rigid segments can limit the amount of flexion or directions of flexion of segments of the extensions 3040a, 3040b. Accordingly, aspects of both the single arm extension and the combination of rigid and flexible elements can create more simple, predictable electrode movement within the oral cavity. The rigid elements can also prevent undesired movement. The flexible connectors can include spring elements that bias the electrodes toward a desired tissue contact location. The combination of the rigid elements with controlled flexion points may also avoid buckling of the extension members. In addition, the single arm can be more comfortable to a patient (particularly when the patient's mouth/tongue move) because it has fewer elements positioned in the oral cavity and near the tongue.

Conversely, manufacturing the device with rigid elements and flexible connectors may be more complicated due to a greater number of parts and smaller parts, and may require greater manufacturing precision to ensure precise movement. In addition, encasing such parts may make the device bulkier. Also, while the movement is repeatable, the more controlled flexion points may not be suitable for a wide range or variety of oral cavity anatomies that may vary from patient to patient.

The flexible resilient extensions 3040a, 3040b can be attached at, and extend inferior and medial, of the posterior rigid flaps 1011a, 1011b. The posterior rigid flaps 1011a, 1011b can extend from the lateral segments 1030a, 1030b in an inferior direction approximately to or adjacent the mylohyoid ridge MHR (FIG. 30B) of the mandible M (FIG. 30B) (a location where the mylohyoid muscle MH attaches to the mandible M, and, below which the target soft tissue structures are located). (See also FIGS. 28A and 30B for representative positioning of flaps 1011a, 1011b). To improve comfort, the motion of the flexible components of the extension members can be limited to the areas of soft tissue, avoiding movement in regions of hard tissue. Further, the motion of the flexible connectors can be limited to the locations where strain relief from tissue movement (e.g., tongue movement) is desired.

The range of motion of the extensions can allow the electrodes follow the range of motion of the soft tissue so that it can maintain contact during soft tissue movement, while restricting electrode movement beyond and out of soft tissue contact. Accordingly, the flexible resilient extensions 3040a, 3040b are attached to the posterior rigid flaps 1011a, 1011b so that they can flex in a superior direction within a broad, full, and/or predetermined range of soft tissue below the mandibular ridge, but only so that the electrodes stay within a region of the soft tissue of the oral cavity inferior to the mylohyoid ridge. The posterior rigid flaps 1011a, 1011b can be generally positioned in a region in the oral cavity adjacent the harder tissue of the mandible. The location of the mylohyoid ridge may vary from patient to patient and accordingly the posterior rigid flaps and or the extension flexibility range can be customized for individual patients.

Multiple electrodes on each extension in this and other representative embodiments herein can provide benefits and/or options for the patient and/or practitioner. For example, electrode pairs may be selected from the multiple electrodes for a variety of reasons prior to or during treatment stimulation. Use of different electrodes can provide alternative tissue contact points as well as alternative current paths through the tissue. Different electrodes and/or stimulation parameters can be used to target different areas, anatomical structures, and/or tissue. One or both of electrodes 1050a, 1051a on one side of the appliance may be selected as having a first polarity while one or more of electrodes 1050b, 1051b on the opposite side may be selected as having an opposing polarity where current is directed from one side of the oral cavity to the other through the target tissue. First electrodes 1050a, 1051a, may be used as an electrode pair of opposite polarity located on one side of the oral cavity. Likewise, second electrodes 1050b, 1051b may be used as an electrode pair of opposite polarity on the opposite side of the oral cavity. The pairs may be activated alternately or simultaneously. Electrodes may be selected from electrode arrays, for example, as shown in representative embodiments herein. Electrode selection can, for example, be based on testing prior to use of the appliance or as an adjustment after initial use of an appliance. Electrode selection can also be made during use of the device. Electrode selection can be based on an algorithm, based on sleep lab and/or other response observations, based on sensed stimulation responses, and/or based on movement within the oral cavity (for example, tongue movement that occurs with electrical stimulation and/or a change in body position) and/or other sensed information.

Different waveforms or variations of pulse width, amplitude and frequency may also be selected and/or implemented in a similar manner to that described with respect to electrode selection. For example, as the patient's tongue base widens in a posterior direction, changing the pulse width and amplitude may compensate for the varying thickness of the muscle and/or greater distance between opposing electrodes. Different electrode pairs at different locations can deliver different waveforms. The practitioner can also vary the waveform from patient to patient, and/or use multipolar electrode configurations. Electrodes, stimulation parameters and/or programs may be selected or adjusted prior to and/or after deployment. They may be selected based on response in a testing mode, for example, by observing or sensing responses or during sleep in a sleep lab or similar environment. Patient responses may be observed using visualization or sensing of upper airway parameters, other patient parameters, and/or other appropriate criteria such as the AHI (Apnea, Hypopnea Index). Electrodes and/or stimulation parameters or programs may be selected and/or adjusted during use in response to a position change of the extension members or electrodes. For example, if the tongue moves the electrodes forward, the more posteriorly situated electrodes 1051a, 1051b may be selected. Electrode response may also change during sleep or during treatment due to movement of the electrodes, and/or patient movement and/or position change. Electrodes stimulation parameters and/or stimulation programs may be adjusted based on observations in a sleep lab or otherwise during sleep. Further, different electrodes, stimulation parameters and/or stimulation programs may be selected if the patient habituates to a particular form of stimulation, in order to elicit a more effective response.

The electrodes 1050a, 1051a, 1050b, 1051b may be selectively activated via logic or controller circuitry of the circuit 1060. The electrodes may be selected based on feedback from sensors (e.g., sensor 1070) that indicate the efficacy of the patient's response to stimulation, including changes that may occur, for example, due to electrode position change or habituation. Accordingly, the sensors may provide information to the electronic circuitry or logic that will be used to adjust the stimulation parameters, including electrode selection (e.g., which electrode(s) is/are active). According to representative embodiments, a body position sensor may be used to determine the position of a subject and to select electrodes based on body position and expected electrode position based on the sensed body position. For example, if a patient is lying on his or her back, the more posterior electrode may be selected assuming that the tongue may move back in a subject's oral cavity in this position. Further, for example, if a left side patient position is sensed, the left electrode pair may be selected for stimulation. In some embodiments, one or more dedicated sensors 1070 provide feedback to control the therapy delivery process. In some embodiments, in addition to or in lieu of the dedicated sensor(s) 1070, the electrodes 1050a, 1051a, 1050b, 1051b, can operate as sensors, as well as therapy signal delivery devices. For example, the electrodes can sense the patient's response during times when the electrodes are not actively delivering an electrical signal. As discussed herein, such breaks in the signal delivery process can occur between pulses of the therapy signal, and/or as a result of the therapy signal being active during only portions of the patient's breathing cycle.

In addition to facilitating electrode selection, multiple electrodes may be used in a program that cycles automatically through patterns of electrodes to improve stimulation results, for example to avoid habituation. Additionally, switching electrode pairs can occur during a single stimulation cycle. For example, during a single breath the electrode selection may switch from electrodes at one location to electrodes at another location. For example, a more anterior electrode may be selected immediately prior to inhalation. And, in order to maintain effective electrode target contact, a posterior electrode may be selected after initiation of inhalation, assuming that the tongue will move the inferior or distal end of the extension forward.

Figure 10:
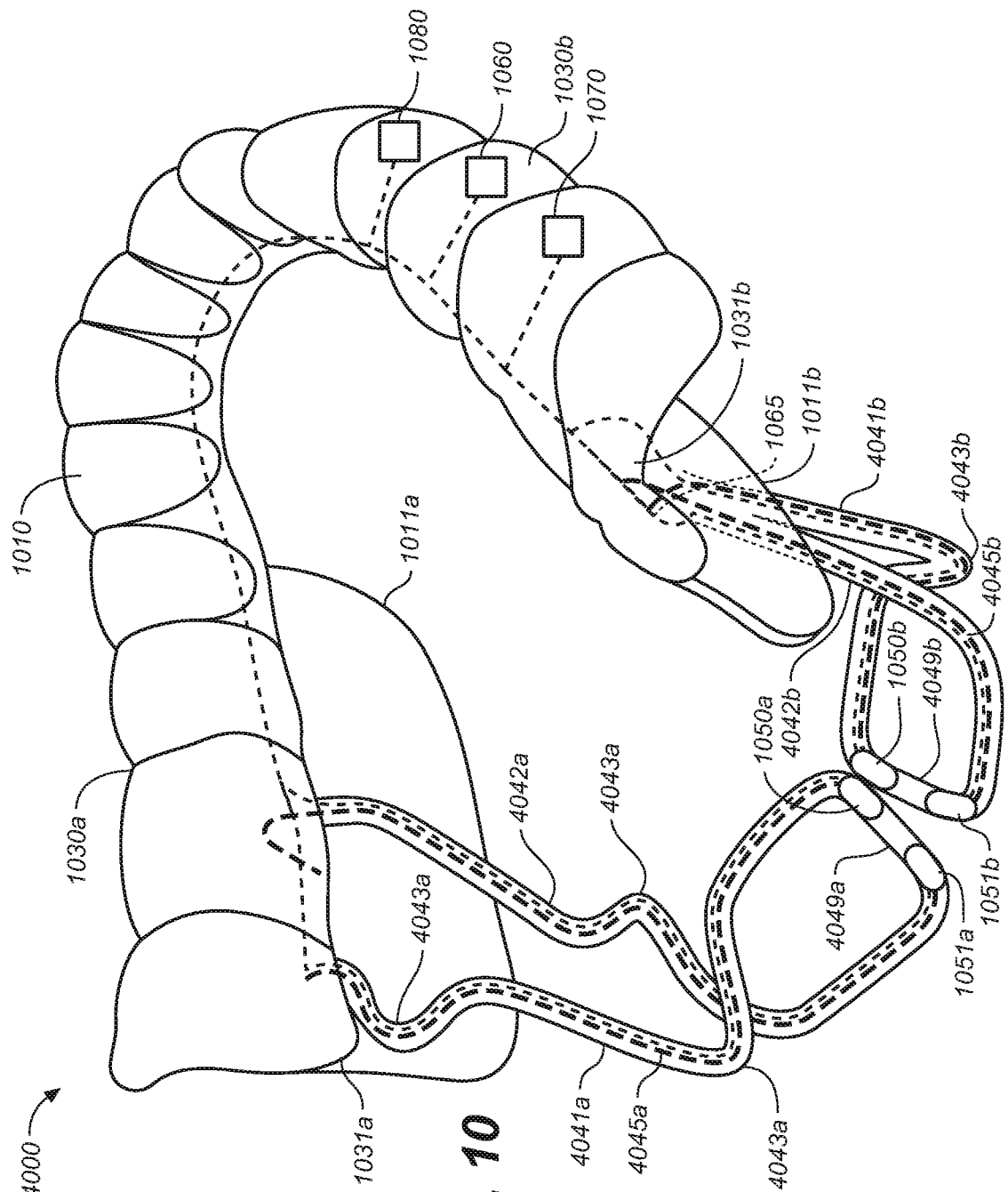
FIG. 10 is an elevated perspective view of an oral appliance configured in accordance with representative embodiments of the present technology.
Figure 11:
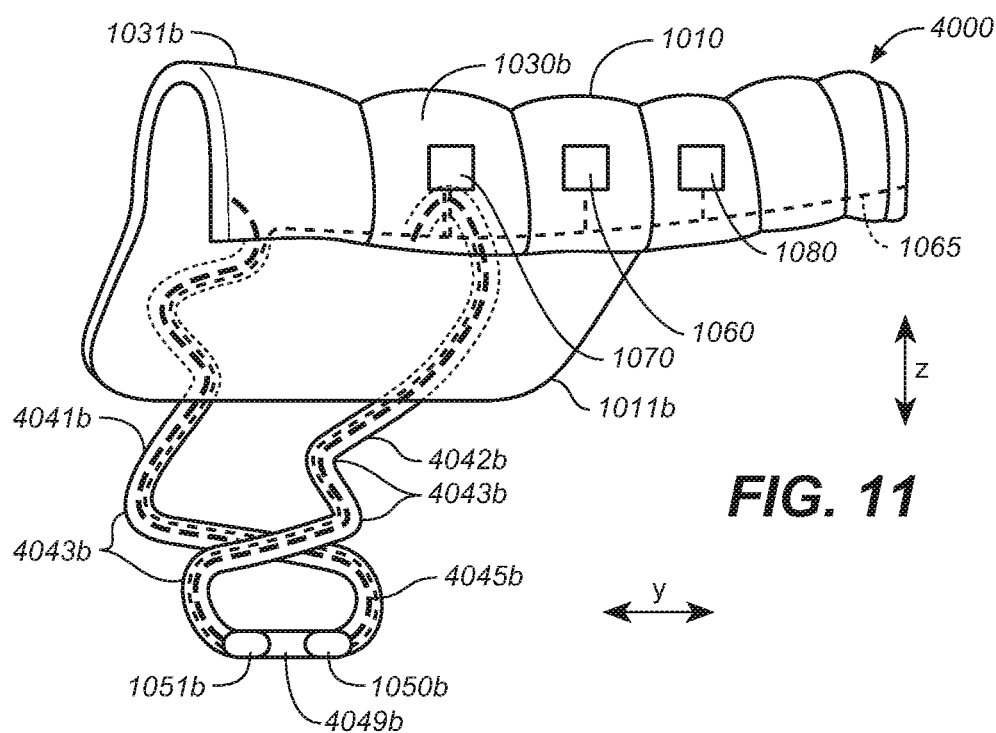
FIG. 11 is a side view of the oral appliance of FIG. 10.
Figure 12:
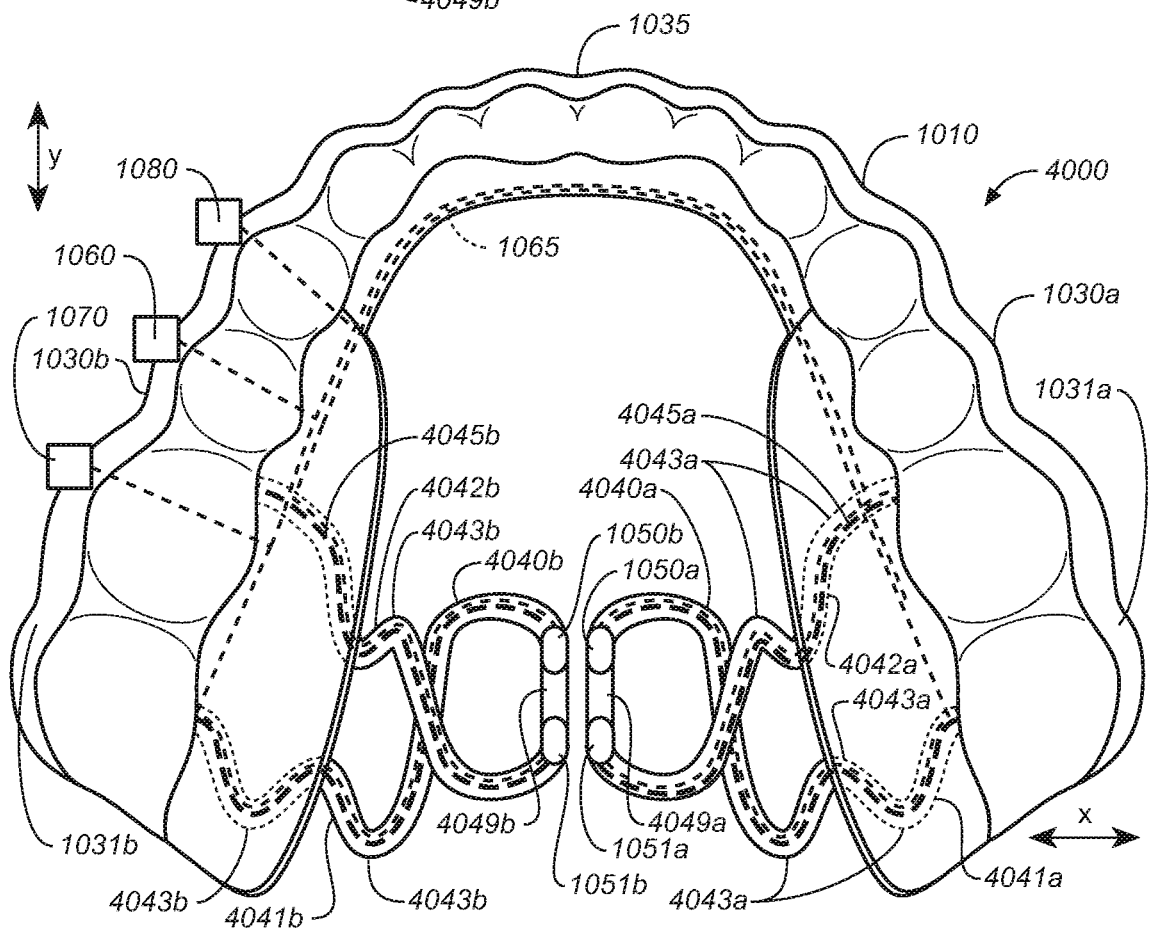
FIG. 12 is a bottom plan view of the oral appliance of FIG. 10.

FIGS. 10-12 illustrate a representative removeable intraoral appliance 4000 having an attachment body 1010. Flexible, resilient extensions 4040a and 4040b are coupled to the corresponding flaps 1011a, 1011b which are coupled to lateral segments 1030a and 1030b at the corresponding posterior molar portions 1031a, 1031b. The flexible resilient extensions 4040a, 4040b may extend inferior and medial of the flaps 1011a, 1011b. In some representative embodiments, the flexion points or stress relief points of the extensions 4040a, 4040b can be positioned to limit flexion or movement to locations inferior to the flaps 1011a, 1011b.

And, as will be described in further detail below, the extensions can each comprise one or more arms coupled to the attachment body flaps at multiple points with the arms crossing over each other to provide stress relief and flexion points. The resulting shape can also form openings that avoid/limit potentially painful or uncomfortable tissue contact. For example, in FIG. 28A, representative extension member 4040b is shown positioned adjacent a sublingual salivary gland, with the salivary gland seated between arms 4041b, 4042b. Thinner less bulky extension members can provide more comfort to the patient.

First electrodes 1050a, 1051a are positioned on the inferior end 4049a of a first extension member 4040a, and second electrodes 1050b, 1051b are positioned on the inferior end 4049b of a second extension member 4040b. The extension members 4040a, 4040b, respectively, couple the electrodes to the corresponding flaps 1011a, 1011b of the body 1010.

The flexible extensions 4040a, 4040b can each include a corresponding posteriorly originating arm 4041a, 4041b coupled to the flaps 1011a, 1011b, and an anteriorly originating arm 4042a, 4042b coupled to flaps 1011a, 1011b in a location anterior to the posteriorly originating arms 4042a, 4042b. The posteriorly originating arms 4041a, 4041b and anteriorly originating arms 4042a, 4042b can each have a plurality of bends or undulations 4043a, 4043b along their lengths to provide flexion points or regions. Each posteriorly extending arm 4041a, 4041b crosses over a corresponding anteriorly originating arm 4042a, 4042b before attaching or joining at their corresponding inferior ends 4049a, 4049b. The crossed-over arms 4041a, 4042a and 4041b, 4042b can form openings adjacent the inferior ends 4049a, 4049b that can provide relief for anatomical structures. For example, such openings can be positioned adjacent salivary glands to avoid painful contact with the glands. (See FIG. 28A). The crossed over arms 4041a, 4042a and 4041b, 4042b also form stress relief or flexion points.

The arms 4041a, 4041b, 4042a, 4042b can include a flexible material. The flexible material may also be resilient and/or can comprise wires 4045a, 4045b that act as spring elements or stiffening elements that may be encased in a lower durometer material. The arms 4041a, 4041b, 4042a, 4042b are relatively thinner than the arms shown in FIGS. 1-3 and in particular, the inferior ends 4049a, 4049b are thinner and less bulky which allows for greater comfort but permits greater movement of the inferior ends 4049a, 4049b and corresponding electrodes 1050a, 1050b, 1051a, 1051b. According to particular representative embodiments, wires 4045a, 4045b bias the inferior ends 4049a, 4049b in a medial direction toward electrical contact in a target tissue area. Wires 4045a, 4045b can bias any one or more of the arms 4041a, 4041b, 4042a, 4042b in a variety of other directions in order to direct the corresponding electrodes toward target stimulation tissue, areas or regions. The wires or other support elements described herein may support the extensions while the cross-over regions, bends or undulations 4043a, 4043b may provide flexion points or regions that allow controlled movement as described with respect to various representative embodiments herein. The arms 4041a, 4041b, 4042a, 4042b may also operate as tethers or range of motion limiters for the extensions and attached electrodes.

Figure 13:
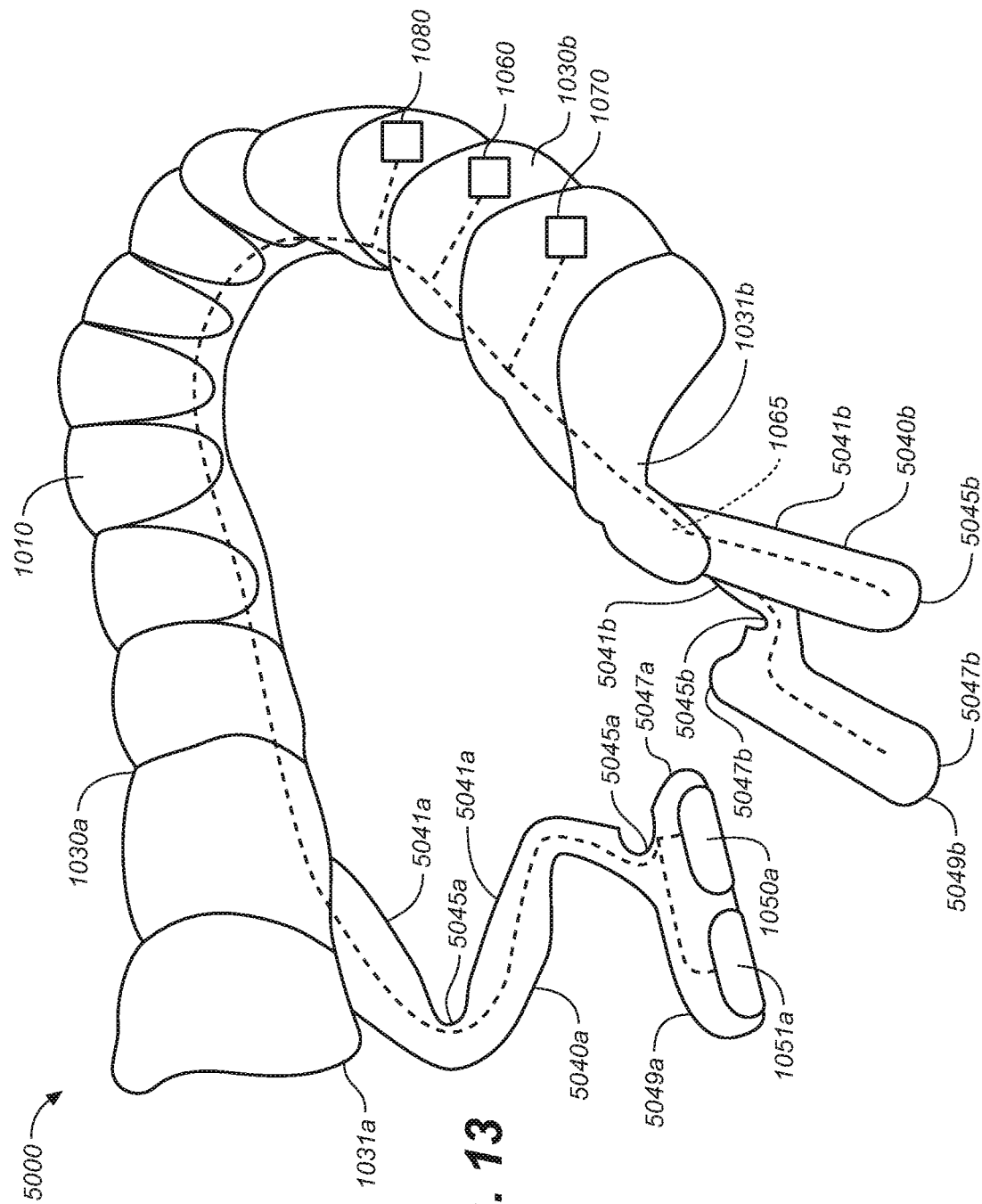
FIG. 13 is an elevated perspective view of an oral appliance configured in accordance with representative embodiments of the present technology.
Figure 14:
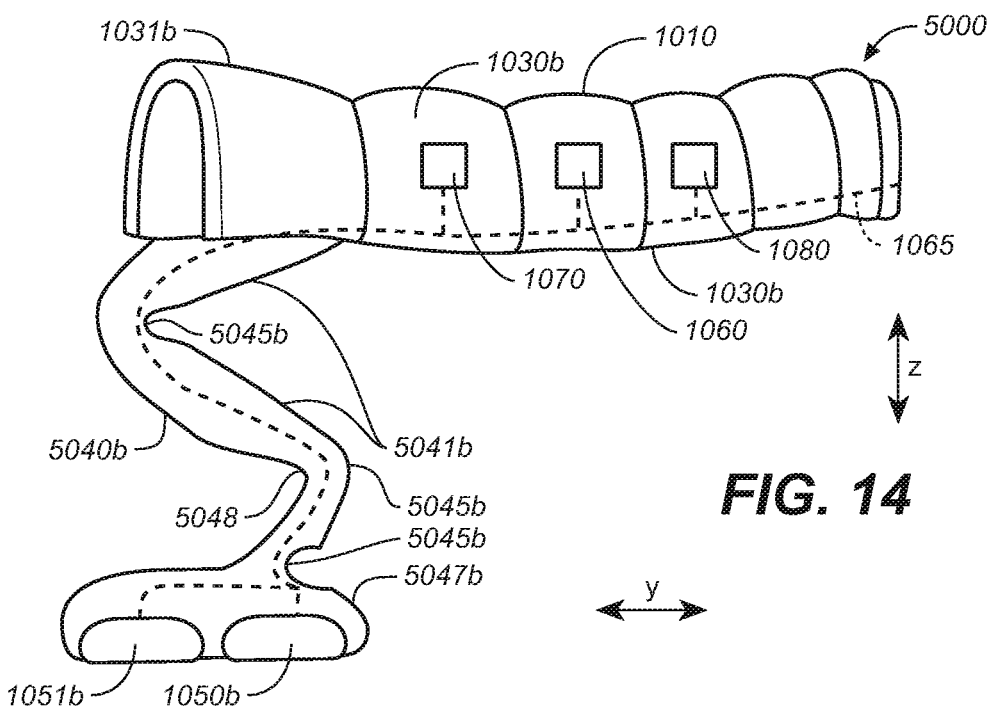
FIG. 14 is a side view of the oral appliance of FIG. 13.
Figure 15:
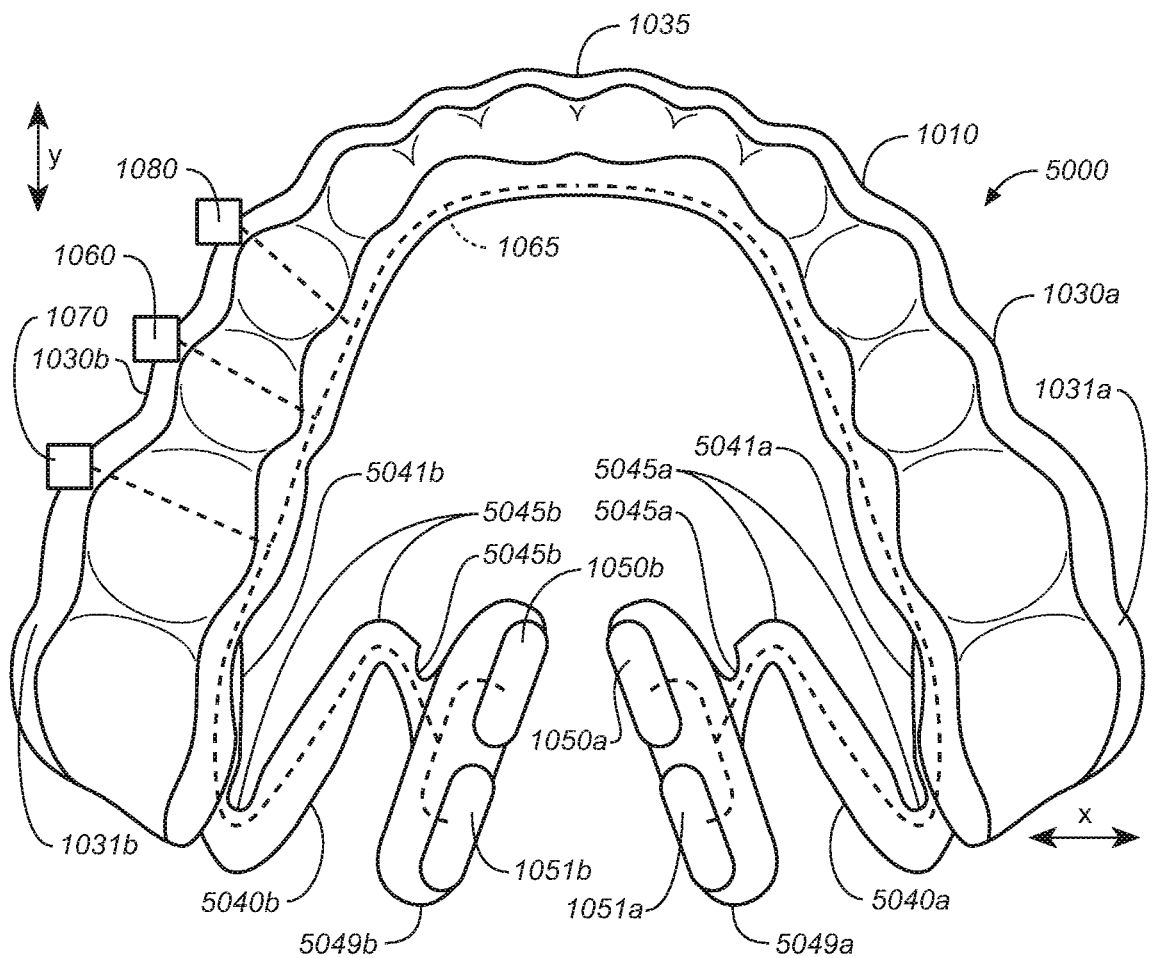
FIG. 15 is a bottom plan view of the oral appliance of FIG. 13.
Figure 16:
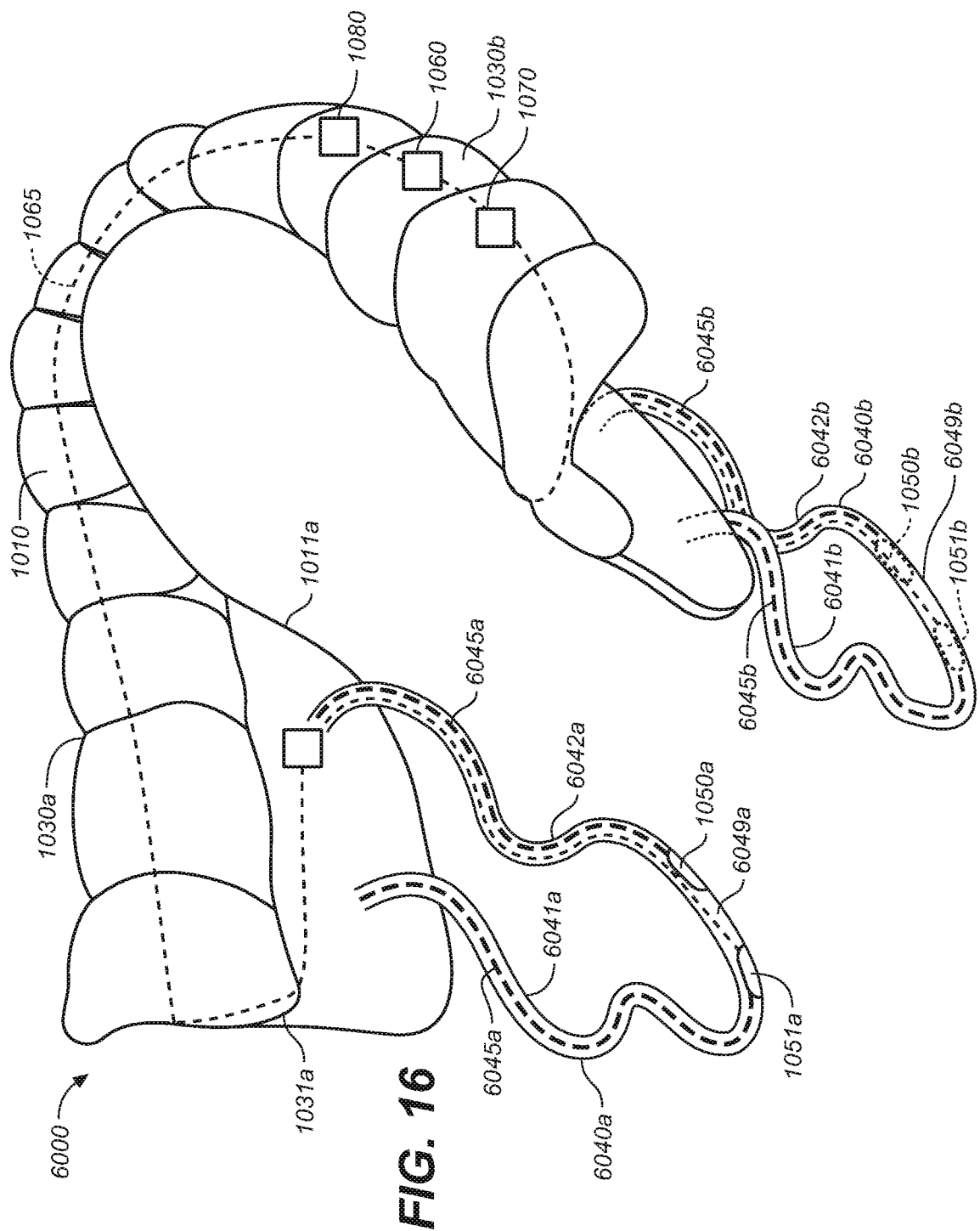
FIG. 16 is an elevated perspective view of an oral appliance configured in accordance with representative embodiments of the present technology.
Figure 17:
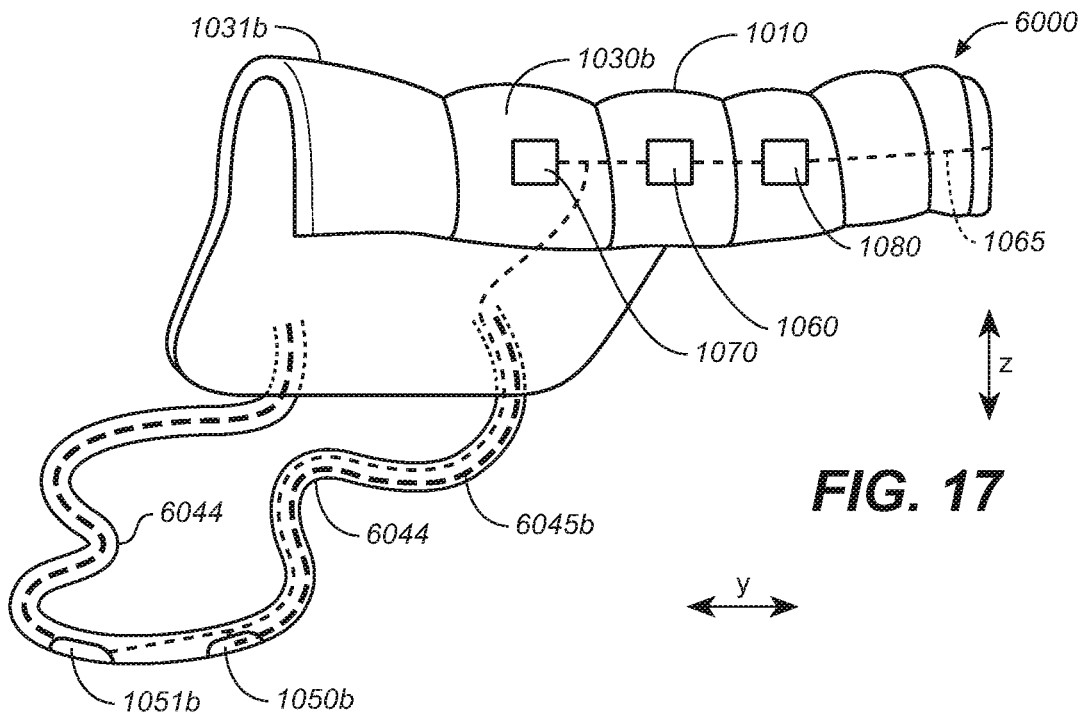
FIG. 17 is a side view of the oral appliance of FIG. 16.
Figure 18:
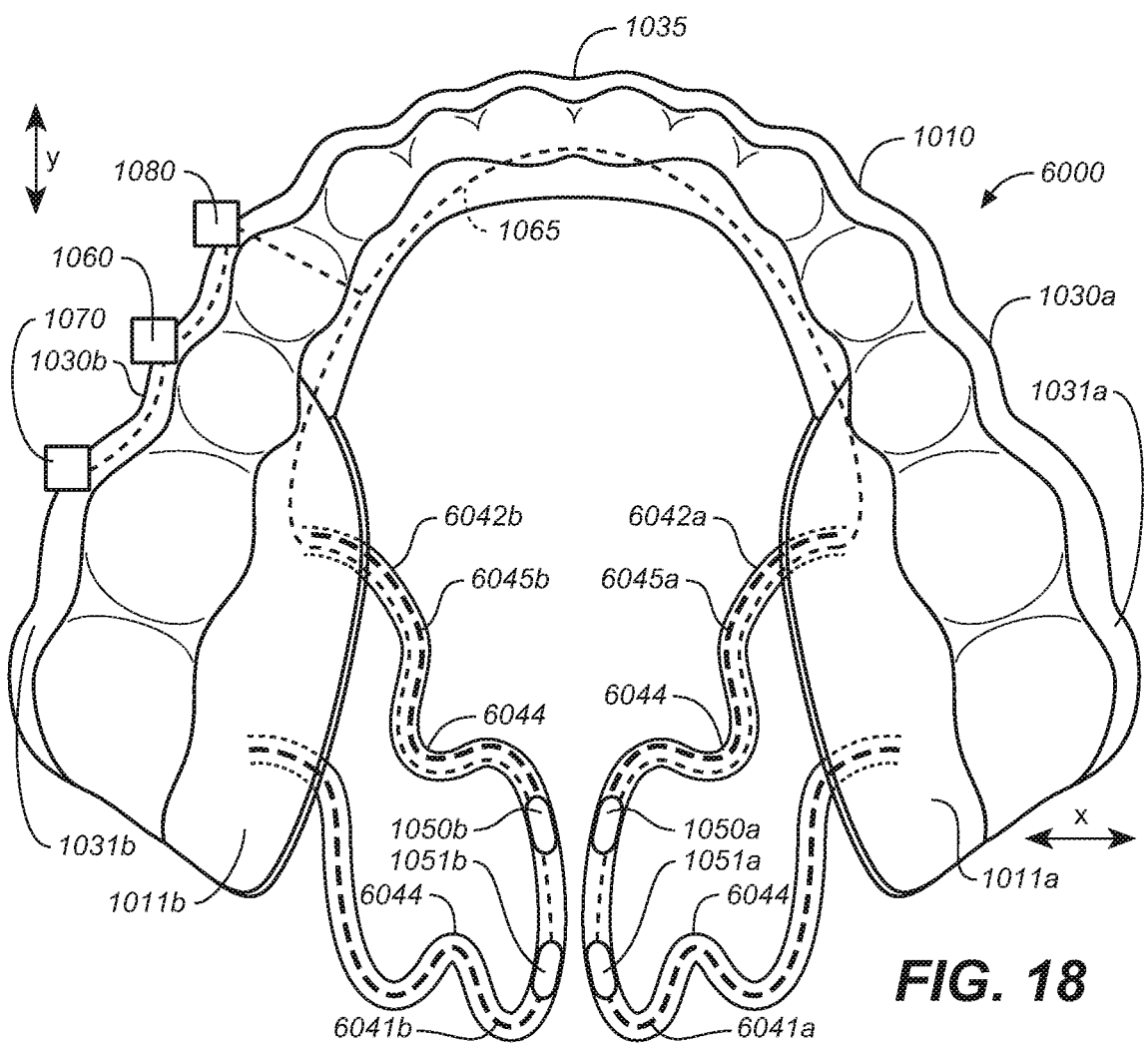
FIG. 18 is a bottom plan view of the oral appliance of FIG. 16.

FIGS. 13-15 illustrate a representative removeable intraoral appliance 5000 having an attachment body 1010. The intraoral appliance includes flexible, resilient extensions 5040a and 5040b coupled to the corresponding lateral segments 1030a and 1030b at the respective posterior molar portions 1031a, 1031b. The flexible resilient extensions 5040a, 5040b may extend inferior and medial of the lateral segments 1030a, 1030b. The flexible resilient extensions 5040a, 5040b may comprise a patient interface portion 5048 that comprises a relatively lower durometer material.

First electrodes 1050a, 1051a are positioned on a first electrode support 5047a which is coupled to an inferior end 5049a of a first extension 5040a. Second electrodes 1050b, 1051b (FIG. 15) are positioned on a second electrode support 5047b which is coupled to an inferior end 5049b of a second extension 5040b.

Similar to FIGS. 7-9, the extensions 5040a, 5040b can each comprise a single arm that includes a plurality of more rigid regions 5041a, 5041b joined by more flexible regions 5045a, 5045b ("flexion regions"). However, rather than flexibly linked rigid members, the flexible resilient extensions 5040a, 5040b are formed of a single flexible resilient element with physical features such as thicker regions and/or thinner regions that provide different amounts, degrees and/or directions of flexion along the length of the extension that effectively form segments, areas, locations, regions, portions, points, and/or axes of greater or lesser flexion and varied directions and degrees of flexion. The resilient properties of the element can bias the extensions in a medial/lateral, inferior/superior, and/or anterior/posterior direction, and/or towards an angular orientation, so as to direct or urge the electrodes towards target stimulation tissue, areas or regions. A relatively simple device or manufacturing process (e.g., injection molding) can be used to form the overall shapes of the extensions, possibly including regions having different thicknesses to allow for different degrees of flexibility. More complex (e.g., out of plane) flexion characteristics can be provided, for example, using notches, cut outs and/or other features. Individualized or customized devices can be 3D printed, injection molded, or otherwise constructed. As illustrated in FIG. 14, the less flexible regions 5041a, 5041b do not include additional support or more rigid structures. However, additional support structures or more rigid elements, and resilient elements can be included in some representative embodiments.

FIGS. 16-19 illustrate another representative removeable intraoral appliance 6000 having an attachment body 1010 and flexible, resilient extensions 6040a and 6040b coupled to corresponding flaps 1011a, 1011b. The flexible resilient extensions 6040a, 6040b may extend inferior and medial of the flaps 1011a, 1011b to limit flexion or movement to locations inferior to the flaps 1011a, 1011b. The extensions 6040a, 6040b can each include at least one corresponding arm 6042a, 6042b coupled to the attachment body flaps at multiple points. The arms 6042a, 6042b can have undulations or bends 6044 along their lengths to provide flexion points, segments, regions, portions, areas, locations, and/or areas that provide stress relief and allow controlled movement, generally as described elsewhere herein. Similar to the arrangement shown in FIGS. 10-12, the arms 6042a, 6042b are thinner and less bulky to provide more comfort to a patient. However, to provide more support along their lengths, the arms 6042a, 6042b do not cross over as they do in FIGS. 10-12.

As shown in FIGS. 16-19, the flexible extensions 6040a, 6040b can each include a corresponding posteriorly originating arm 6041a, 6041b connected to a corresponding anteriorly originating arm 6042a, 6042b. The anteriorly originating arms 6042a, 6042b are coupled to the flaps 1011a, 1011b at a location anterior to where the posteriorly originating arms 6042a, 6042b attach to the flaps 1011a, 1011b. First electrodes 1050a, 1051a are positioned at the inferior end 6049a of the first extension 6040a, and second electrodes 1050b, 1051b are positioned on inferior end 6049b of the second extension 6040b.

The arms 6041a, 6041b, 6042a, 6042b can include a flexible material. The flexible material may also be resilient and/or can comprise wires 6045a, 6045b that act as spring elements or stiffening elements that may be encased in a lower durometer material. The wires 6045a, 6045b can bias the inferior ends 6049a, 6049a in a variety of directions and toward electrical contact with target tissue. The arms 6041a, 6041b, 6042a, 6042b may also operate as tethers or range of motion limiters for the extensions and attached electrodes. The anteriorly and posteriorly originating arms on each side of the appliance 6000 are joined to each other, and, can be formed integrally as a generally U-shaped element, with bends and curves as described above.

Figure 19:
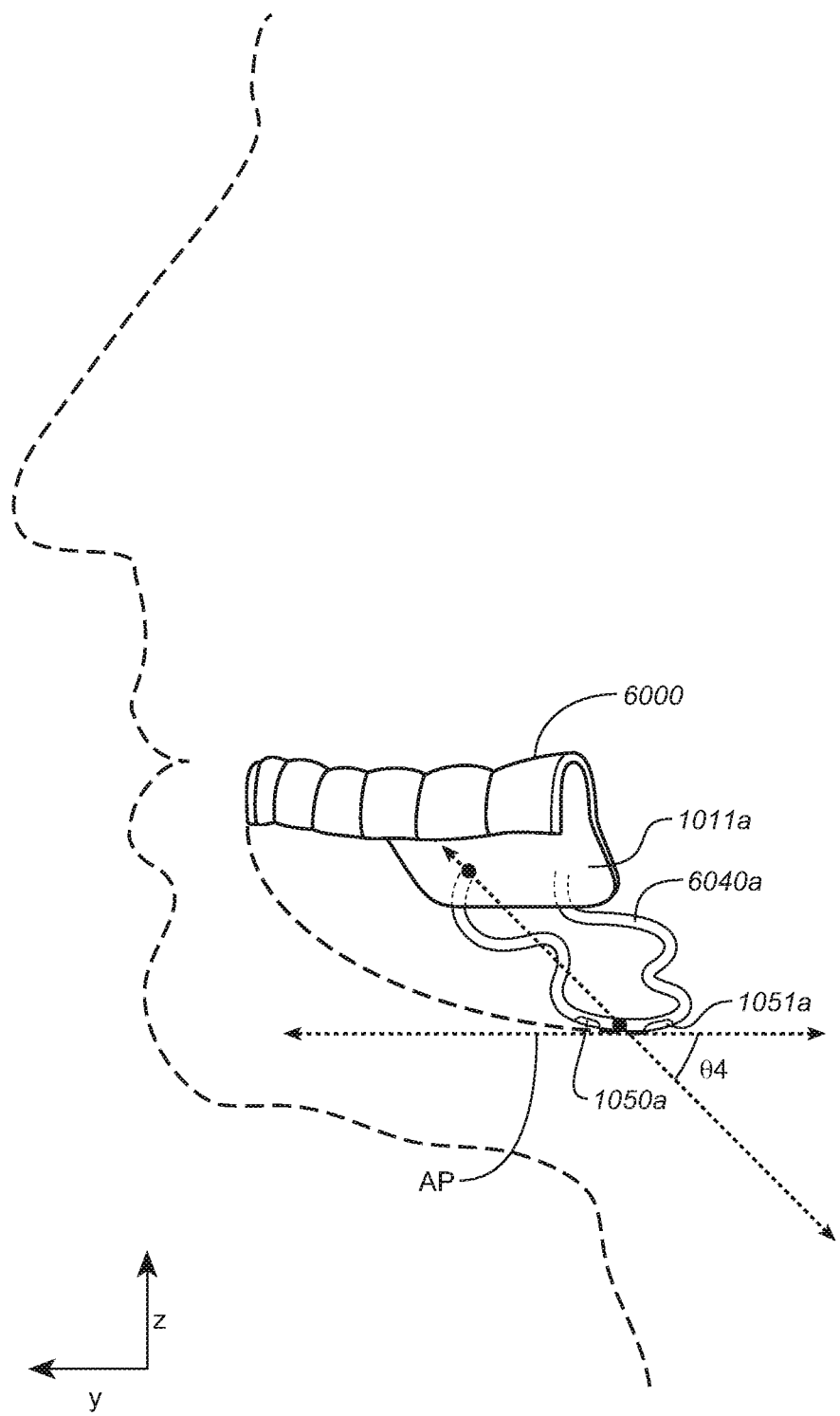
FIG. 19 is a partially schematic cut-away sagittal view of the patient's head depicting the oral appliance of FIG. 16 positioned in the oral cavity and configured in accordance with representative embodiments of the present technology.

The anteriorly originating arms 6042a, 6042b are attached in anterior positions on the flaps 1011a, 1011b. Referring now to FIG. 19, the anterior attachment points along with the midpoint of the inferior ends 6049a, 6049b define corresponding lines forming angles θ4 with respect to the axial plane AP (as viewed from the y-z plane). The angle is more acute than would be formed by the arrangement shown in FIGS. 10-12. It is expected that the more acute angle will provide greater anterior-to-posterior support of the attached electrodes. The angle θ4 is similar to the angle that would be formed by the anterior arm shown in FIGS. 1-3. However, in the arrangement shown in FIGS. 16-19, the motion of the extensions 6040a, 6040b is limited to areas of soft tissue by the attachment to the flaps 1011a, 1011b as described with reference to FIGS. 10-12, in order to provide greater patient comfort. In representative embodiments, the angle θ4 may range from between 35 degrees and 110 degrees.

FIG. 20 illustrates the intraoral appliance 6000 of FIGS. 16-19 with additional electrodes 1052a, 1053a, 1052b, 1053b located on the arms 6042a, 6042b of the extensions 6040a, 6040b. The electrodes 1050a, 1051a, 1052a, 1053a on extension 6040a and electrodes 1050b, 1051b, 1052b, 1053b on extension 6040b can be selected for activation using any of the techniques described herein. The multiple electrodes 1050a, 1051a, 1052a, 1053a, 1050b, 1051b, 1052b, 1053b can be used to target different areas, anatomical structures, and/or tissue. The electrodes 1050a, 1051a, 1052a, 1053a, and/or 1050b, 1051b, 1052b, 1053b may operate as an array as described herein. In general, in this and other representative embodiments, the different electrode positions on the extensions, and/or an electrode array, can allow the practitioner, patient and/or the device logic to select different current paths and/or directions of current paths through tissue to obtain a desirable stimulation response. Accordingly, prior to deploying the intraoral stimulation device and/or in adjusting a deployed intraoral stimulation device, the stimulation program and electrode selection therein can be tested and updated (e.g., optimized).

FIG. 21 illustrates the intraoral appliance 6000 generally similar to that shown in FIGS. 16-19, but with each extension 1040a, 1040b further including an elongate bar 6050 positioned at the distal end of the extensions 6040a, 6040b. The bars 6050 extend generally in a posterior-to-anterior direction with electrodes 1050a, 1051a and 1052a positioned along one bar 6050 and electrodes 1050b, 1051b, 1052b positioned on the laterally opposing bar. The electrodes and stimulation parameters can be selected as described herein with respect to FIG. 20. The bars 6050 in some representative embodiments can be more flexible, more rigid, or may exhibit generally similar material properties as the arms 6042a, 6042b. More flexible bars can allow the bars to conform to the tissue. The elongate bars can provide stimulation options particularly when the tongue moves (which tends to move the extensions and electrodes posteriorly and anteriorly). The electrodes 1050a, 1051a, 1052a, and/or 1050b, 1051b, 1052b, may operate as an array as described in more detail herein.

Figure 22:
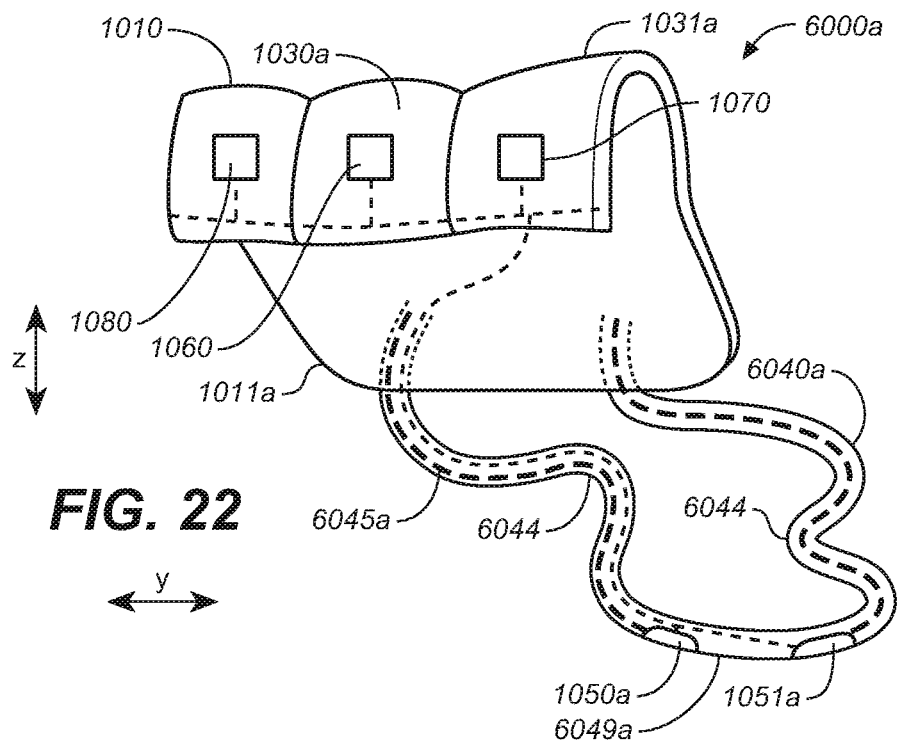
FIG. 22 is an elevated side perspective view of an oral appliance configured in accordance with representative embodiments of the present technology.

FIG. 22 illustrates a representative removeable intraoral appliance 6000a having a single lateral element 1030a and a flap 1011a with a single attached extension 6040a and electrodes 1050a, 1051a. The intraoral appliance attachment body 1010a attaches to one side of the patient's oral cavity and has one extension instead of two extensions on laterally opposite sides of the oral cavity. The appliance 6000a may be used to provide electrical stimulation to one side of the oral cavity by directing current between electrodes 1050a, 1051a.

Figure 23A:
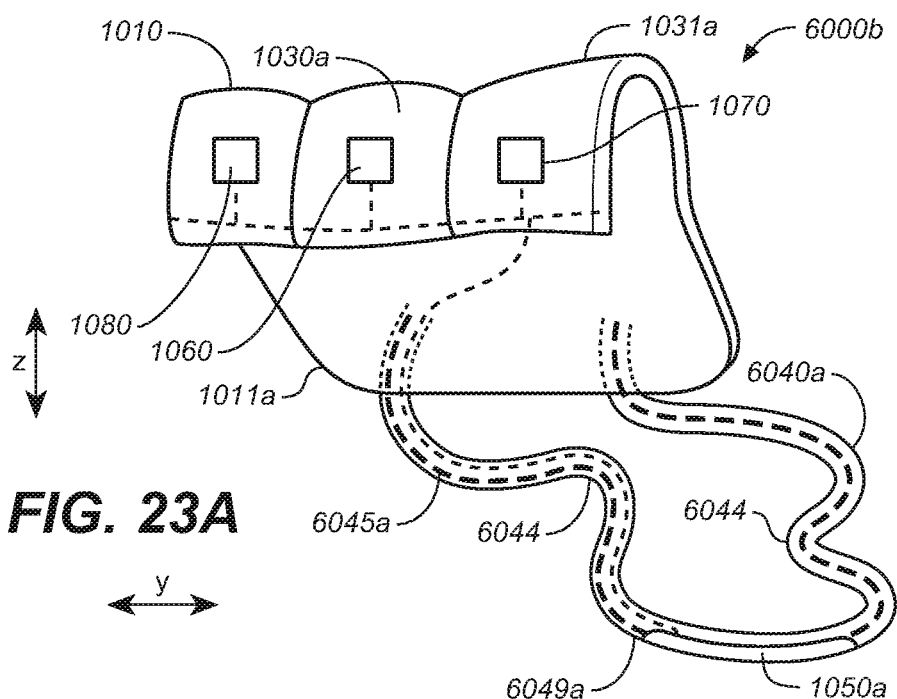
FIG. 23A is an elevated side perspective view of an oral appliance configured in accordance with representative embodiments of the present technology.
Figure 23B:
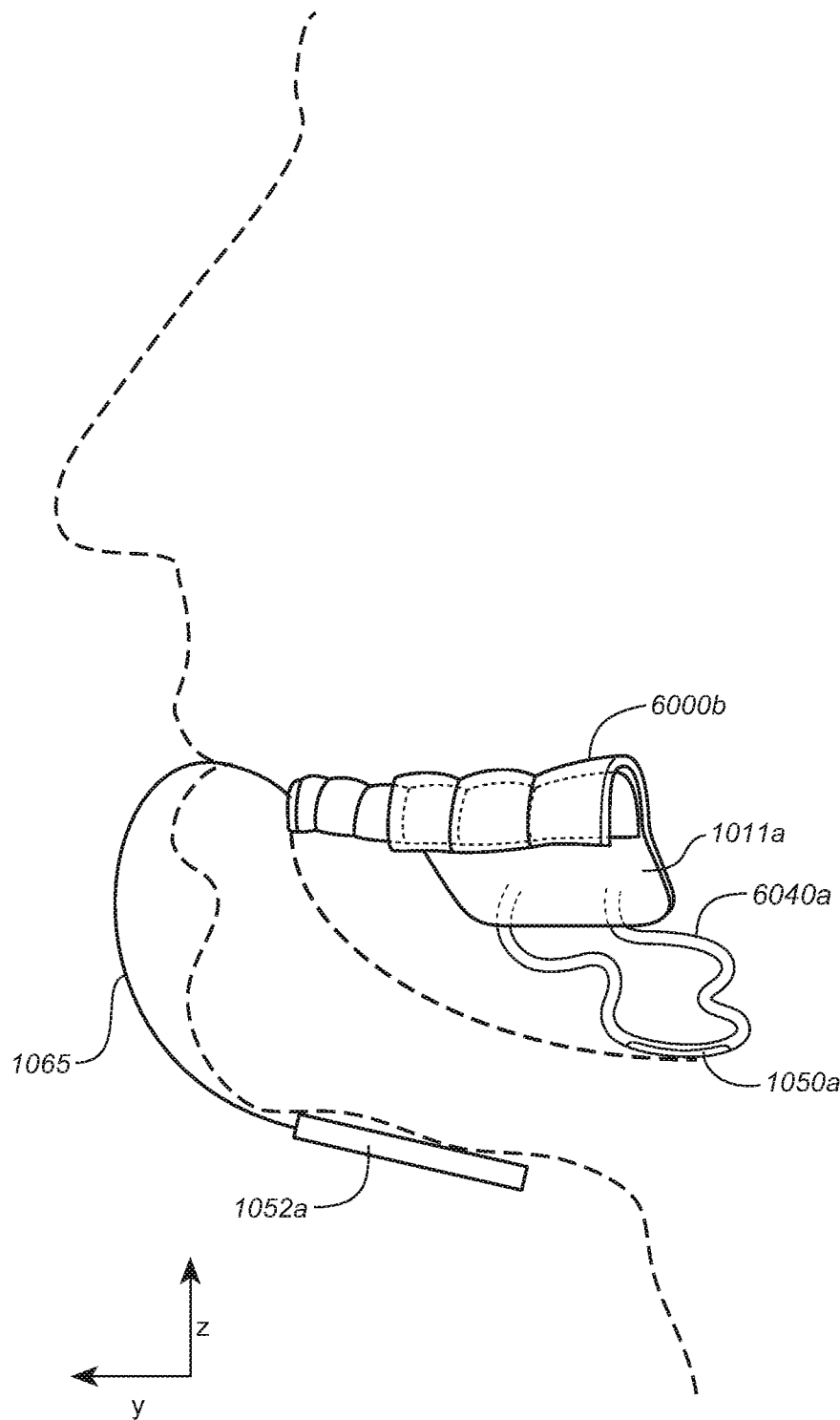
FIG. 23B is a partially schematic cut-away sagittal view of the patient's head depicting the oral appliance of FIG. 23A positioned in the oral cavity and configured in accordance with representative embodiments of the present technology.

FIGS. 23A and 23B illustrate another representative removeable intraoral appliance 6000b having a single lateral element 1030a and a flap 1011a with a single attached extension 6040a and one or more first electrodes 1050a. The intraoral appliance attachment body 1010a attaches to one side of an oral cavity and has one extension instead of two extensions on laterally opposite sides of the oral cavity. A second (opposing) electrode 1052a may be coupled to a location external to the oral cavity, as shown in FIG. 23B. The appliance 6000b can be used to provide electrical stimulation to the tissue of the oral cavity by directing current between the first and second electrodes 1050a, 1052a. The second electrode 1052a can be coupled to the electronic circuitry with a connector or wire 1065. By changing the position of the (external) electrode 1052a, the practitioner and/or patient can controllably direct the electrical current to the target tissue.

Figure 24:
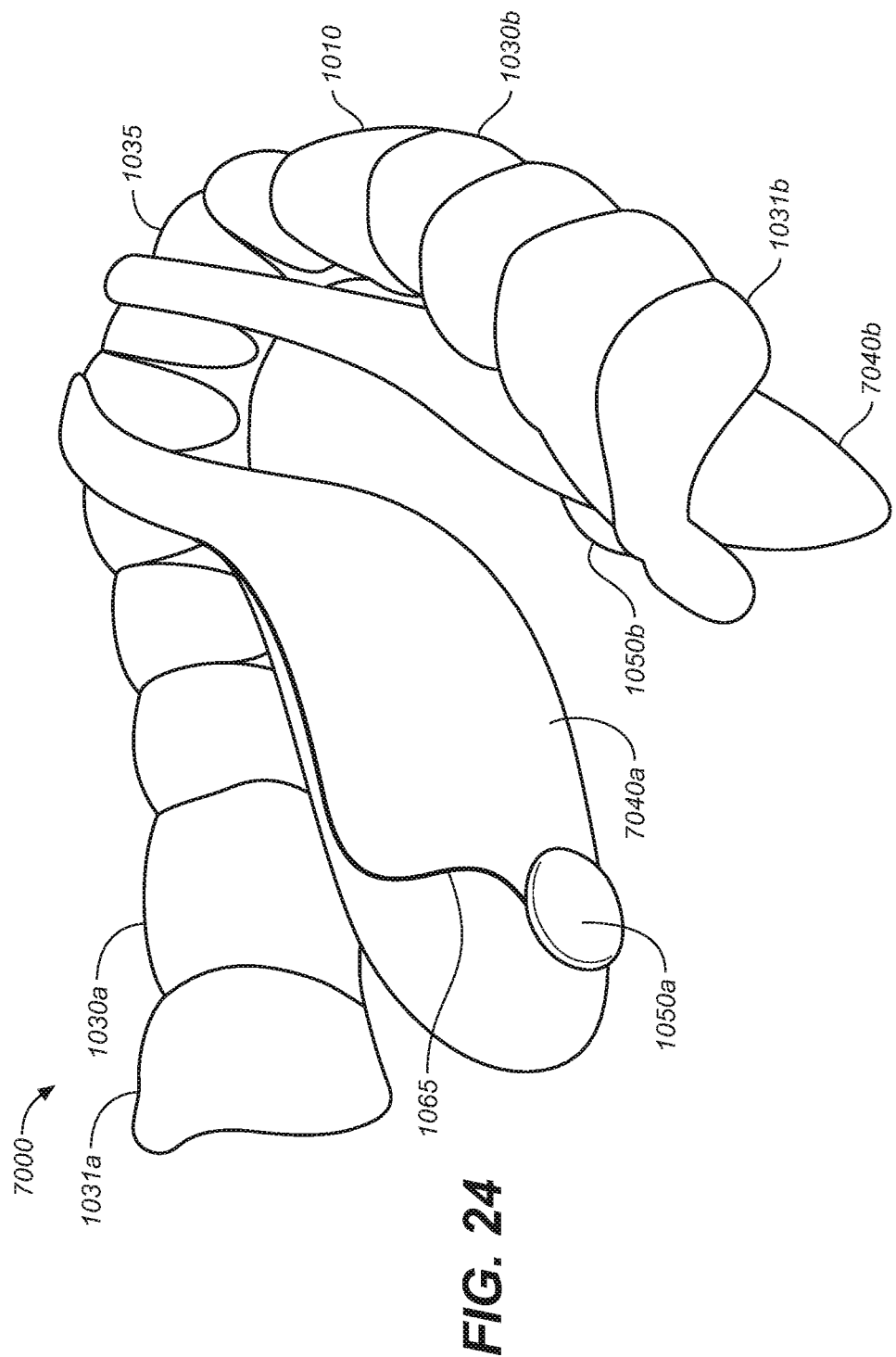
FIG. 24 is an elevated perspective view of an oral appliance configured in accordance with representative embodiments of the present technology.
Figure 25:
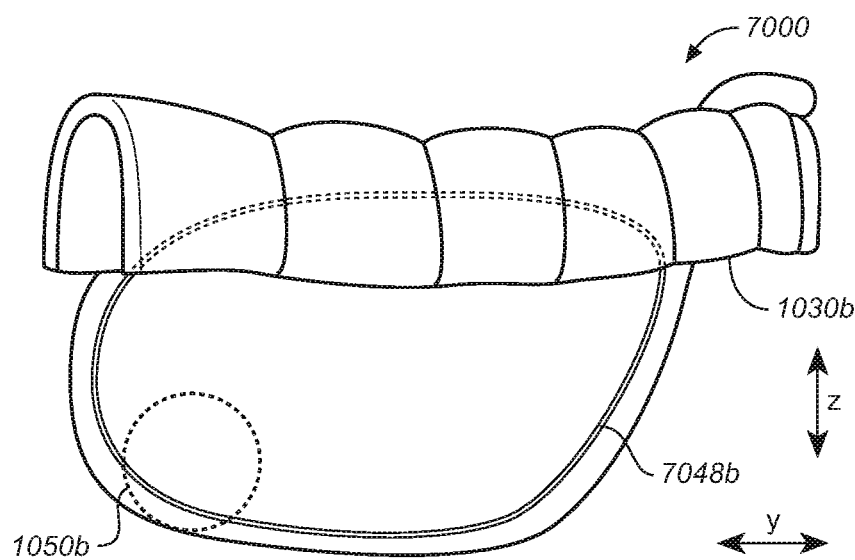
FIG. 25 is a side perspective view of the oral appliance of FIG. 24.
Figure 26:
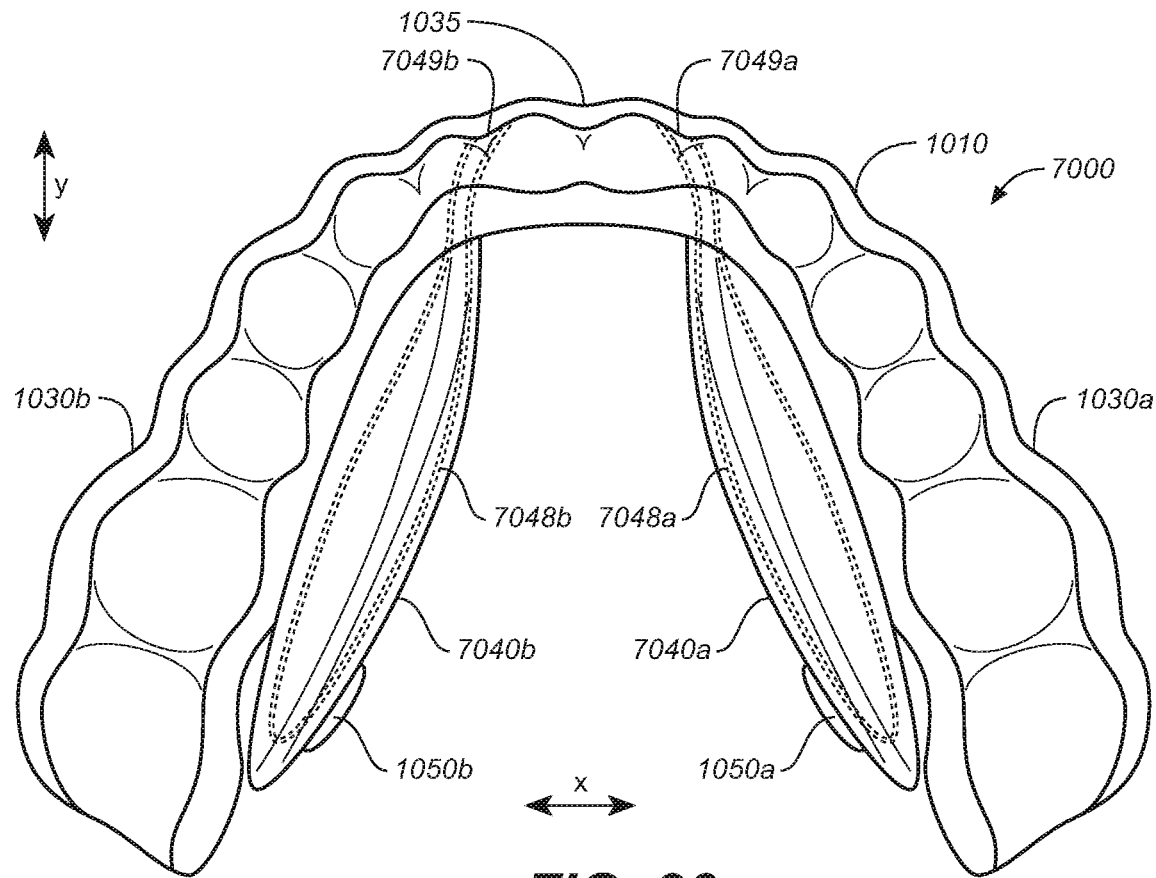
FIG. 26 is a bottom plan view of the oral appliance of FIG. 24.

FIGS. 24-26 illustrate another representative removeable intraoral appliance 7000 configured in accordance with embodiments of the present technology. The appliance 7000 includes electrodes 1050a, 1050b coupled to corresponding inflatable flexible resilient extensions 7040a, 7040b which are then respectively coupled to the medial or anterior portion 1035 of the attachment body 1010. The flexible resilient extensions 7040a, 7040b can alternatively be coupled to the lateral segments 1030a, 1030b at a posterior or other location. The electrodes 1050a, 1050b can be coupled to the extensions 7040a, 7040b at an inferior end of the extensions. Referring to FIG. 26, the flexible resilient extensions 7040a, 7040b can include bladders 7048a, 7048b and valves 7049a, 7049b for receiving a fluid inflation medium (e.g., air or a liquid or polymer, such as a polymer that cures to or forms a malleable structure). The bladders 7048a, 7048b can be inflated to provide a flexible resilient electrode support that positions the electrodes 1050a, 1050b at corresponding target locations. The flexible resilient extensions 7040a, 7040b can have a shape that further facilitates positioning the electrodes medial to sublingual and/or other salivary glands.

The inflation level can be adjusted for an individual patient to provide comfort and proper electrode positioning, and can allow anatomical movement while at the same time providing support and proper fit. While the electrical stimulation can be generally as described herein, the inflatable elements of the extensions can reduce undesirable movement by the extension elements while maintaining some flexibility. The inflatable elements can also provide patient comfort due to the conformability of the extensions to an individual patient's oral cavity. The bladder or bladders can also be inflated, for example, during testing to ensure good electrode contact during evaluation. The bladders can also be used as sensors that sense pressure. Pressure changes can indicate a response to stimulation, for example by tongue movement. Pressure changes can also indicate patient position. For example, a differential pressure between connected bladders on opposing lateral sides can indicate patient movement or position. The bladder may form an entire extension or may be positioned on a portion of an extension. One or more bladders or inflatable elements can be positioned on extensions including, but not limited to, the extensions illustrated in FIGS. 1-37C. FIG. 37C (described in further detail later) also illustrates a bladder positioned on a portion of an extension.

FIG. 27 illustrates an array of electrodes 8050 that may be used instead of any single electrode or electrode pair described in FIGS. 1-26 herein (e.g., electrodes 1050a, 1050b, 1051a, 1051b). The electrodes of the array 8050 are coupled to the electronic circuitry 1060 (FIG. 1), which may include a program or controller logic to selectively activate any one or more of these electrodes at an anodic or cathodic current or voltage, or any electrode can operate as one of a multipolar electrode arrangement. An opposing electrode array can be positioned on an opposite lateral side of the patient's oral cavity, with individual electrodes forming one or more electrode pairs with the opposing array. Electrodes and electrode pairs can be selected based on feedback from one or more sensors 1070 (FIG. 1) that indicate the effectiveness of the stimulation. One or more of the electrodes in the array 8050 can be used to sense the patient's response to electrical stimulation, in additional to or in lieu of delivering the stimulation. Electrodes can also be selected in view of changes in the patient's response to electrical stimulation (e.g., during sleep) due to movement of the electrodes, and/or other factors (e.g., habituation).

Figure 28A:
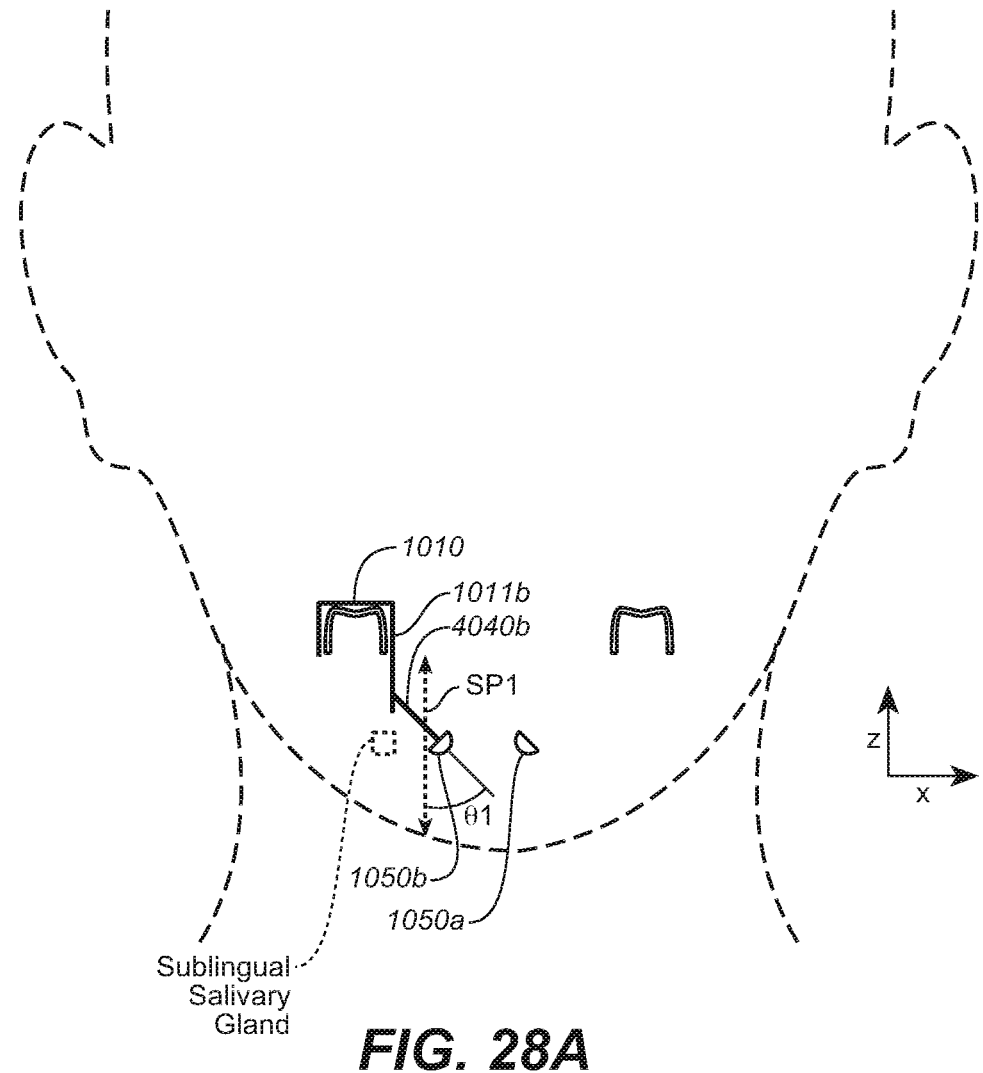
FIG. 28A is a partially schematic, cut-away coronal view of a patient's head depicting electrodes positioned in the oral cavity and configured in accordance with representative embodiments of the present technology.

FIG. 28A is a partially schematic, cut-away coronal view of a patient illustrating first and second electrodes 1050a, 1050b positioned in the patient's oral cavity. Extension member 4040b is shown as a representative example, extending medially and inferior to the flap 1011b of the body 1010 and positioned adjacent a sublingual salivary gland. Other representative extension members can be similarly positioned in a patient's oral cavity. The second electrode 1050b is shown oriented at an initial angle θ1 with respect to a sagittal plane SP1 which is perpendicular to the coronal plane. The angular rotation of the electrode (about the y axis) with respect to the sagittal plane is referred to herein as the roll. Any of the foregoing representative oral appliances shown in FIGS. 1-26 can be configured to orient the electrode(s) at a predetermined roll angle or within a range of predetermined roll angles in order to direct the electrodes, or current from the electrodes, toward the target stimulation tissue, areas and/or regions. An "initial" angle θ1 as used herein is evident when the oral appliance is not yet positioned in the patient's oral cavity. The value of the angle may change once the appliance is actually positioned in an oral cavity, for example due to an individual patient's particular anatomy. However, the electrode will continue to be biased toward the "initial angle". When positioned in the patient's oral cavity, the flexible extension of the appliance can flexibly permit the electrode to roll. The extension member can also be resilient, causing the electrode to tend to move toward the initial angle θ1. The extension member can include struts, wires, springs, material thickness variations, supports, reinforcements with stiffer materials and/or other features that limit the amount of roll. The initial angle θ1 can be from about 5 degrees to about 90 degrees with respect to the sagittal or x-z plane (with 0 degrees being in the inferior direction), or between 25 and 75 degrees with respect to the sagittal or x-z plane, or between 25 and 50 degrees with respect to the sagittal or x-z plane. According to some embodiments herein, the initial angle θ1 of the electrode is selected based on an individual patient's anatomy and/or response to the electrical stimulation. The amount of roll flexibility, e.g., the degree to which the extension will allow an electrode to roll away from the initial angle, can also be controlled or preset. For example, in some representative embodiments, the roll flexibility can be up to 45 degrees from the initial angle, in either direction.

Figure 28B:
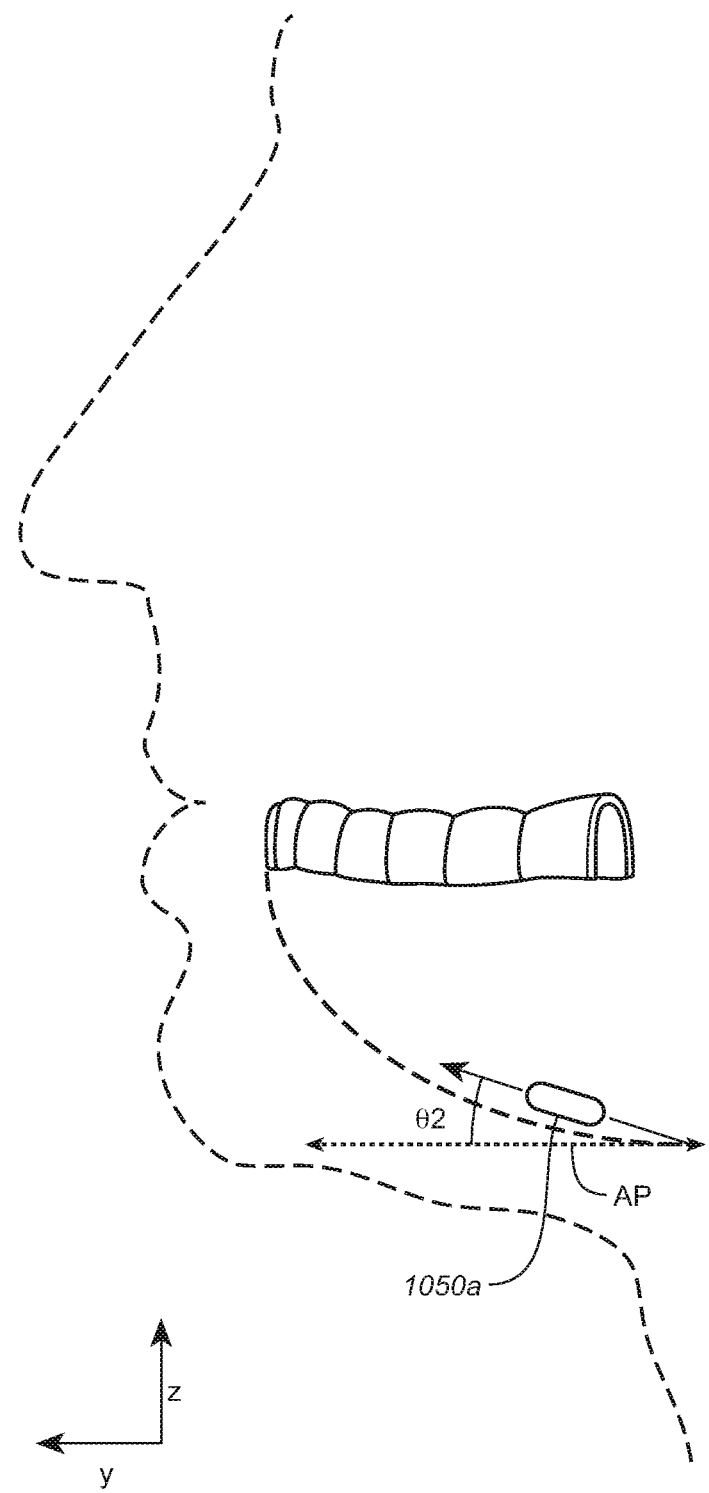
FIG. 28B is a partially schematic, cut-away sagittal view of the patient's head depicting electrodes positioned in the oral cavity and configured in accordance with representative embodiments of the present technology.

FIG. 28B is a partially schematic, cut-away sagittal view of the patient illustrating the first electrode 1050a oriented at an initial angle θ2 with respect to a transverse plane AP which is perpendicular to the sagittal plane. The angular rotation of the electrode (about the x axis) with respect to the axial plane is referred to herein as the pitch. The oral appliance 1000 can be configured to bias the first electrode 1050a toward an initial pitch angle in order to direct the electrode (or current from the electrode), toward the target stimulation tissue, areas or regions. According to some representative embodiments, the initial pitch angle can be between 0 and 45 degrees. The amount of pitch flexibility, i.e., the amount the extension will allow an electrode to pitch from the initial angle can also be controlled or preset. For example, in some representative embodiments, the pitch flexibility can be up to 45 degrees from the initial angle, in either direction.

Figure 28C:
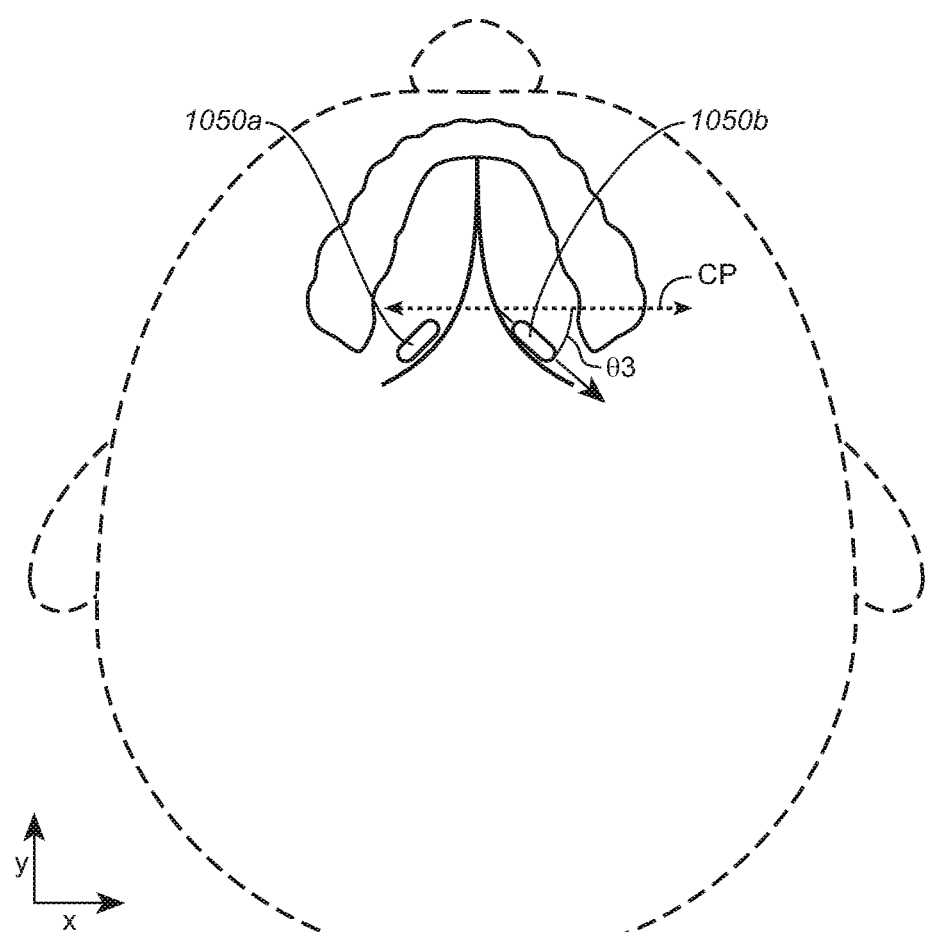
FIG. 28C is a partially schematic, cut-away transverse view of the patient's head depicting electrodes positioned in the oral cavity and configured in accordance with representative embodiments of the present technology.

FIG. 28C is a partially schematic, cut-away transverse view of the patient depicting the first and second electrodes positioned in the oral cavity. The second electrode 1050b is shown oriented at an initial angle θ3 with respect to a coronal plane CP which is perpendicular to the axial plane. The angular rotation of the electrode (about the z axis) with respect to the coronal plane is referred herein to as the yaw. The corresponding oral appliance can be configured to bias the electrode toward an initial yaw angle in order to direct the electrodes (or current from the electrode), towards target stimulation tissue, areas or regions. According to some representative embodiments the initial yaw angle can be between 0 and 45 degrees. The amount of yaw flexibility, i.e., the amount the extension will allow an electrode to yaw from the initial angle can also be controlled or preset. For example, in some representative embodiments, the yaw flexibility can be up to 45 degrees from the initial angle, in either direction.

Any of the electrodes described herein can have an angular orientation defined by one or more of the roll, pitch and/or yaw angles. The specific angle or combination of angles can be preset to fit a large portion of the patient populations or can be tailored to a specific patient.

Figure 30A:
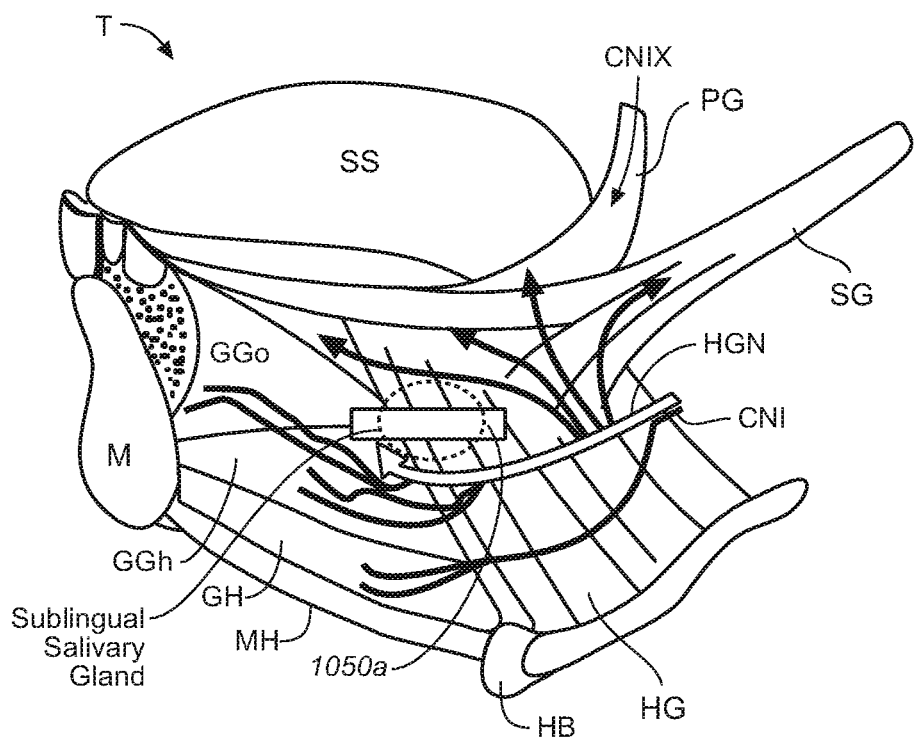
FIG. 30A is a side sectional view of a patient's tongue with an electrode of an intraoral stimulation device in an optional position for stimulation, in accordance with representative embodiments of the present technology.
Figure 30B:
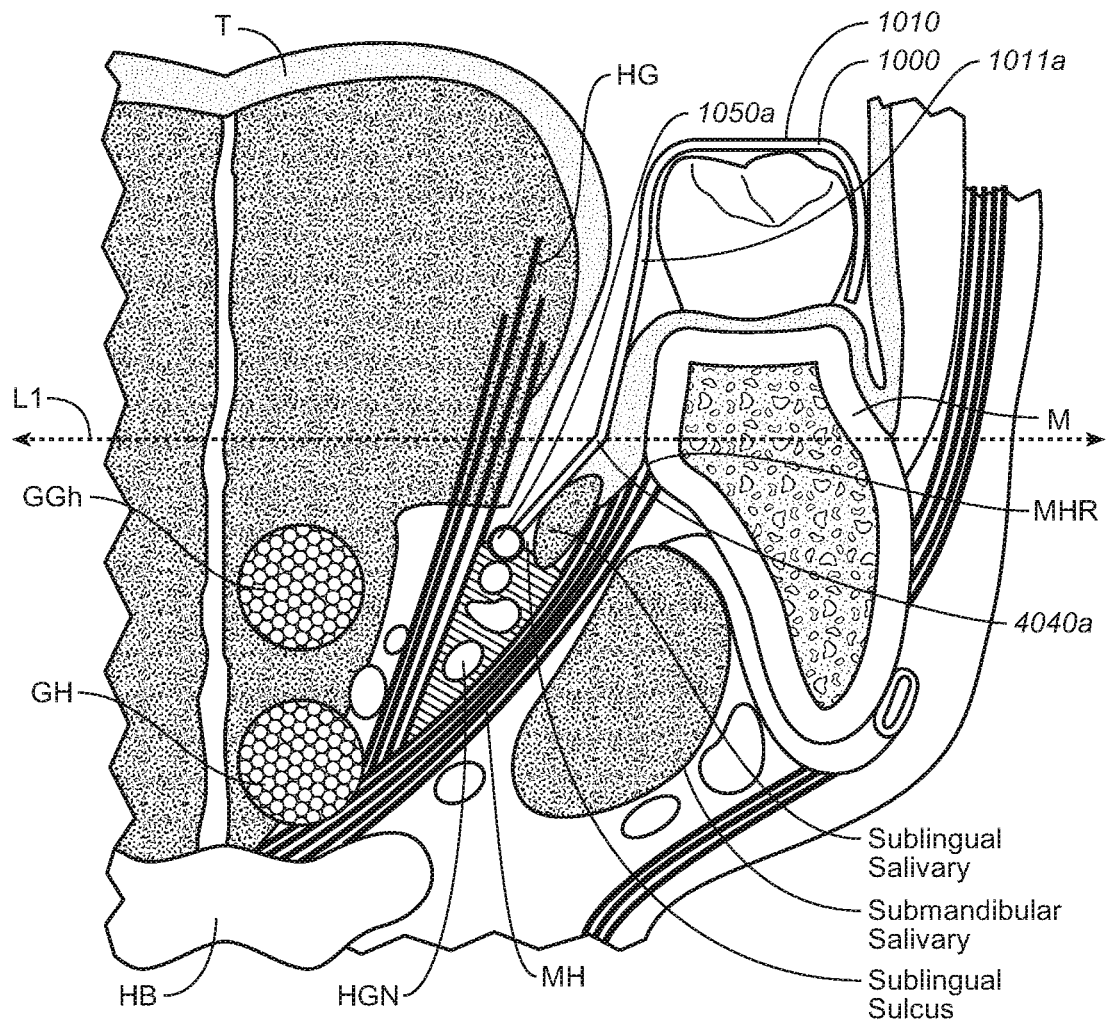
FIG. 30B is a frontal section anterior view sectioned behind the first molar of the patient's oral cavity and with an electrode of an intraoral stimulation device in an optional position for stimulation, in accordance with representative embodiments of the present technology.

FIGS. 30A and 30B illustrate a representative example in which an intraoral appliance having any one or combination of the features described above with reference to FIGS. 1-37C positions any of the electrodes described herein within the sublingual sulcus near the nerve branches that activate the geniohyoid muscle GH and the genioglossus horizontal muscle GGh. Several of the physiological features shown in FIG. 30A are also shown in FIG. 29A, discussed previously.

As an example, a representative electrode 1050a is coupled to a representative extension 4040a (FIG. 30B) as positioned medial with respect to the sublingual salivary gland and the submandibular salivary gland. The flexible resilient extension 4040a of the intraoral appliance shown in FIG. 30B extends medially of the attachment body 1010 to constrict and/or bias the electrode 1050a to a position within the sublingual sulcus. The flexible resilient extension 4040a positions the electrode 1050a in a manner that facilitates the electrode seating itself within the sublingual sulcus. The flexible resilient extension 4040a permits the electrode 1050a to move when the tissue or tongue move, for example, because of a change in the patient position, sleep state and/or tongue and/or muscle position in the upper airway. A second electrode or electrode array (not shown in FIG. 30B) can be positioned in the laterally opposing sublingual sulcus and current can be directed between the electrodes on opposing sides of the tongue.

FIG. 30B also shows a line L1 about at which the mylohyoid muscle attaches to the mylohyoid ridge of the mandible. Above the line L1, where relatively less soft tissue movement occurs, the rigid flap 1011a can prevent significant movement of the attached extension member 4040a. Below the line L1, is a region of soft tissue in which the extension 4040a and attached electrode 1050a are permitted greater range of motion. Accordingly, in order to improve electrode/tissue contact and patient comfort, the motion of the flexible components of the extension members can be limited to the areas of soft tissue. Further, the motion of the flexible connectors can be limited to the location where strain relief from movement is desired. This region of tissue movement is generally below the mandible.

While FIGS. 30A and 30B illustrate a particular potential stimulation target, there are a number of other targets within the oral cavity that, when stimulated, will potentially prevent or reduce collapse or obstruction of the upper airway. Accordingly, an oral appliance as described herein can position one or more electrodes to target a variety of anatomical and/or nerve structures of the upper airway/oral cavity to improve upper airway patency or tone.

The electronics circuit described herein can include a signal generator (e.g., a pulse generator) that is powered by a rechargeable battery and that can deliver stimulation pulses, such as a biphasic waveform. The stimulation pulses may be symmetrical or asymmetrical, depending on the application. The stimulation waveform can be adjustable within a range of waveforms, via the electronic circuitry. Such adjustments may be based on sensed feedback. The stimulation may occur continuously or periodically (e.g., in accordance with a duty cycle) and/or can be triggered by a sensed parameter.

Figure 31A:
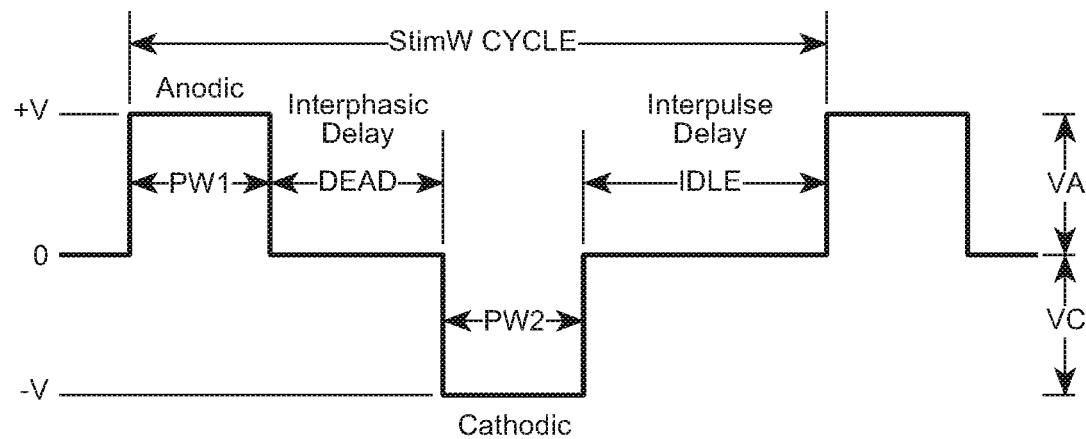
FIG. 31A is a representative example of a stimulation cycle of a stimulation waveform.
Figure 31B:
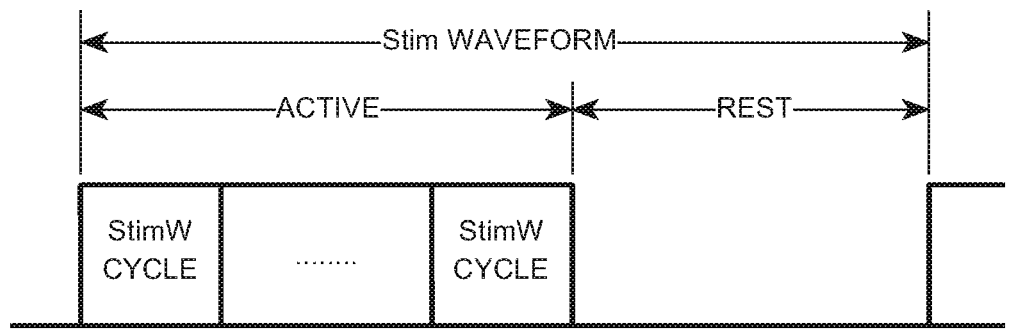
FIG. 31B is a representative example of a stimulation waveform including active and resting periods.

A variety of suitable electrical stimulation waveforms and techniques can be used to stimulate the patient's tissue. Representative examples are illustrated in FIGS. 31A and 31B and include a series of a biphasic stimulation pulses or stimulation wave cycles (identified as StimW CYCLE). The stimulation waveform parameters can include active cycles and rest cycles. The active cycles include one or more stimulation wave cycles. The stimulation wave cycle shown in FIG. 31A comprises an anodic pulse followed by an interphasic delay, a cathodic pulse and then an interpulse delay. Accordingly, a stimulation wave cycle includes the following parameters: anodic pulse width (PW1), anodic amplitude (e.g., voltage or current amplitude VA), interphasic delay/dead time, cathodic pulse width (PW2), cathodic amplitude (e.g., voltage or current amplitude VC), interpulse delay/idle time, and peak-to-peak amplitude (PP). The parameters may also include identity of the electrode(s) to which the signal is directed. The anodic pulse width (PW1) in some representative embodiments is between 40 μs and 300 μs. The anodic amplitude (VA) in some representative embodiments ranges from 0.3V to 11V. The interphasic delay in some representative embodiments can be from 10 μs to 100 μs. The cathodic pulse width (PW1) is some representative embodiments is between 40 μs and 300 μs. The cathodic amplitude (VA) in some representative embodiments ranges from 0.3V to 11V. The interpulse delay in some representative embodiments can be from 10 μs to 100 μs. The peak-to-peak amplitude in some representative embodiments can be from about 5 mAmp to 20 mAmp. Representative frequencies range from about 30 Hz to about 300 Hz.

FIG. 31B illustrates a stimulation waveform comprising an active cycle and a rest cycle. The active cycle includes one or more of stimulation cycles (StimW CYCLE) as shown in FIG. 31A. The rest cycle has no stimulation cycles. According to some representative embodiments, the ratio of active duration to rest duration can be between 1:1 and 1:9. As a representative example, if the ratio is 1:9, and there are 300 active cycles, there can be 2700 rest cycles.

In a representative example the stimulation voltage may be presented independently to each contact or electrode. For the positive pulse, the positive contact can be pulled to the drive voltage and the negative contact is pulled to ground. For the negative pulse, the negative contact can be pulled to the drive voltage and the positive contact is pulled to ground. For dead time and idle time, both contacts are driven to ground. For the rest time, both contacts are at a high impedance. To prevent DC current in the contacts, each half-bridge can be coupled to the contact through a capacitor, for example, a 100 μF capacitor. In addition, a resistor can be placed in series with each capacitor to limit the current in the case of a shorted contact. The pulses of the therapeutic waveform cycle may or may not be symmetric, but, are generally shaped to provide a net-zero charge across the contacts.

Figure 32:
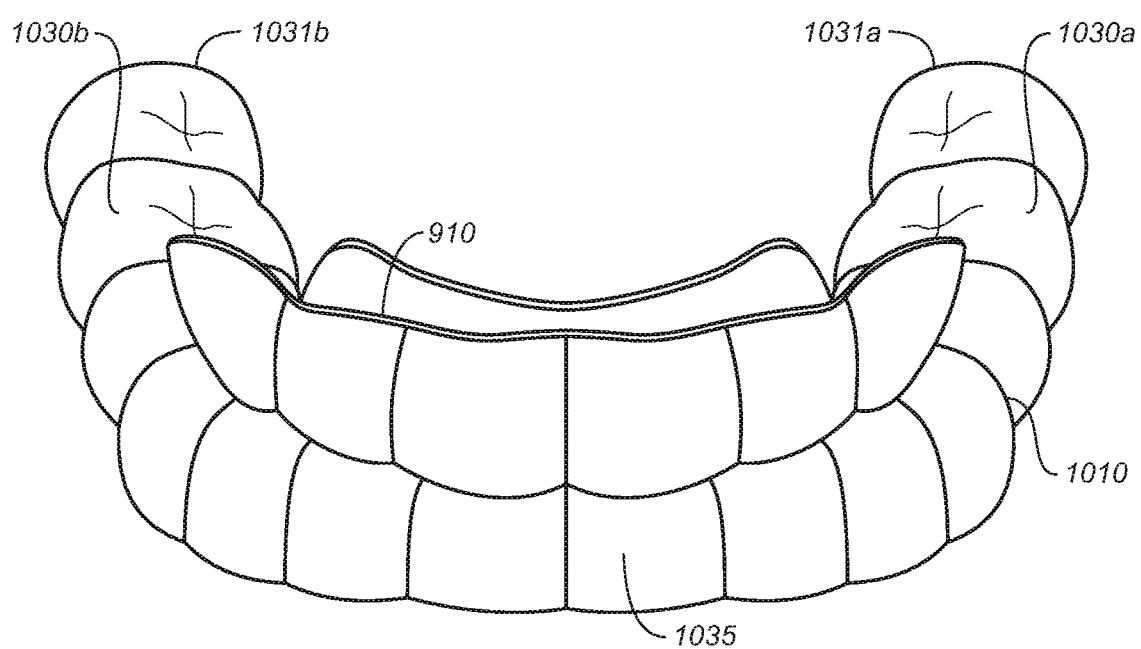
FIG. 32 is a front elevational view of an intraoral appliance configured in accordance with representative embodiments of the present technology.

FIG. 32 illustrates a body 1010 of an oral appliance that may be similar to the oral appliance of any of the foregoing representative embodiments. The appliance further includes an upper body 910 coupled to the body 1010. The upper body 910 is configured to secure to one or more of the upper teeth of the upper jaw so that when the appliance is position in an oral cavity, the upper jaw and lower jaw are generally more stationary with respect to each other. This additional attachment to the upper teeth provides a more stable electrode connection to the tissue of the oral cavity by preventing extra movement of the upper and lower jaws with respect to each other. The attachment can be flexible or rigid. The body 1010 can be configured to engage any suitable combination of upper and lower teeth, including front teeth and/or molars.

4. Representative Adjustability Features

Intraoral stimulation devices configured in accordance with embodiments of the present technology can be used to screen patients to identify those likely to respond to the therapies disclosed herein, and/or to test out elements of the system and/or system parameters before finalizing or solidifying elements of the system for long term use. Accordingly, representative devices have moveable electrodes that can be moved to various positions so that when placed in a patient's oral cavity they can be at different locations. Thus, the electrodes can be positioned in different locations to obtain a desired response and identify a desired electrode position (configuration). Each individual patient's anatomy is different, and a more effective stimulation response can be obtained for an individual patient by identifying positions of, and/or locations for, electrodes, and placing electrodes in these desired positions and/or locations. The electrodes can be moved in one or more directions. For example, the electrodes can be moved in anterior-posterior, inferior-superior, and/or medial-lateral directions. In addition to or in lieu of axial motion, the electrode(s) can be moved to different angular orientations.

In addition to positioning electrodes for a desired response, a test device can be used to position electrodes in different locations prior to manufacture of an individualized intraoral stimulation device, in order to identify desired device dimensions and electrode positions. With this information, an individualized or tailored intraoral device can be manufactured. Depending on the embodiment, representative intraoral stimulation response test devices can be used to (1) vary electrode positions and/or electrode selection or configurations; (2) vary stimulation parameters or programs; and/or (3) detect the response of the upper airway. According to some representative embodiments, a nasal endoscope can be used to observe the upper airway response of at least some anatomical structures, for example, tissue tensing and bulk movement. The anatomical structures observed can include, but are not limited to: the velum, oropharynx, epiglottis and/or tongue base. The response can be scored by an observer and the results used to select a final extension member and/or electrode configuration. Alternatively, or in addition, sensors can be used to sense response to stimulation as described herein as well as measurements in a sleep lab or similar environment where effectiveness can be evaluated, for example using an AHI.

Still further, devices with moveable electrodes can be used for long-term therapy, in addition to, or in lieu of being used as a test or screening device. For example, the patient can sleep with device having moveable electrodes, and the electrode position can be changed by automatic actuators via a feedback loop. The feedback loop can be based on a feedback signal corresponding to the patient's breathing, EMG signal, tongue motion, and/or other suitable parameters.

Figure 33A:
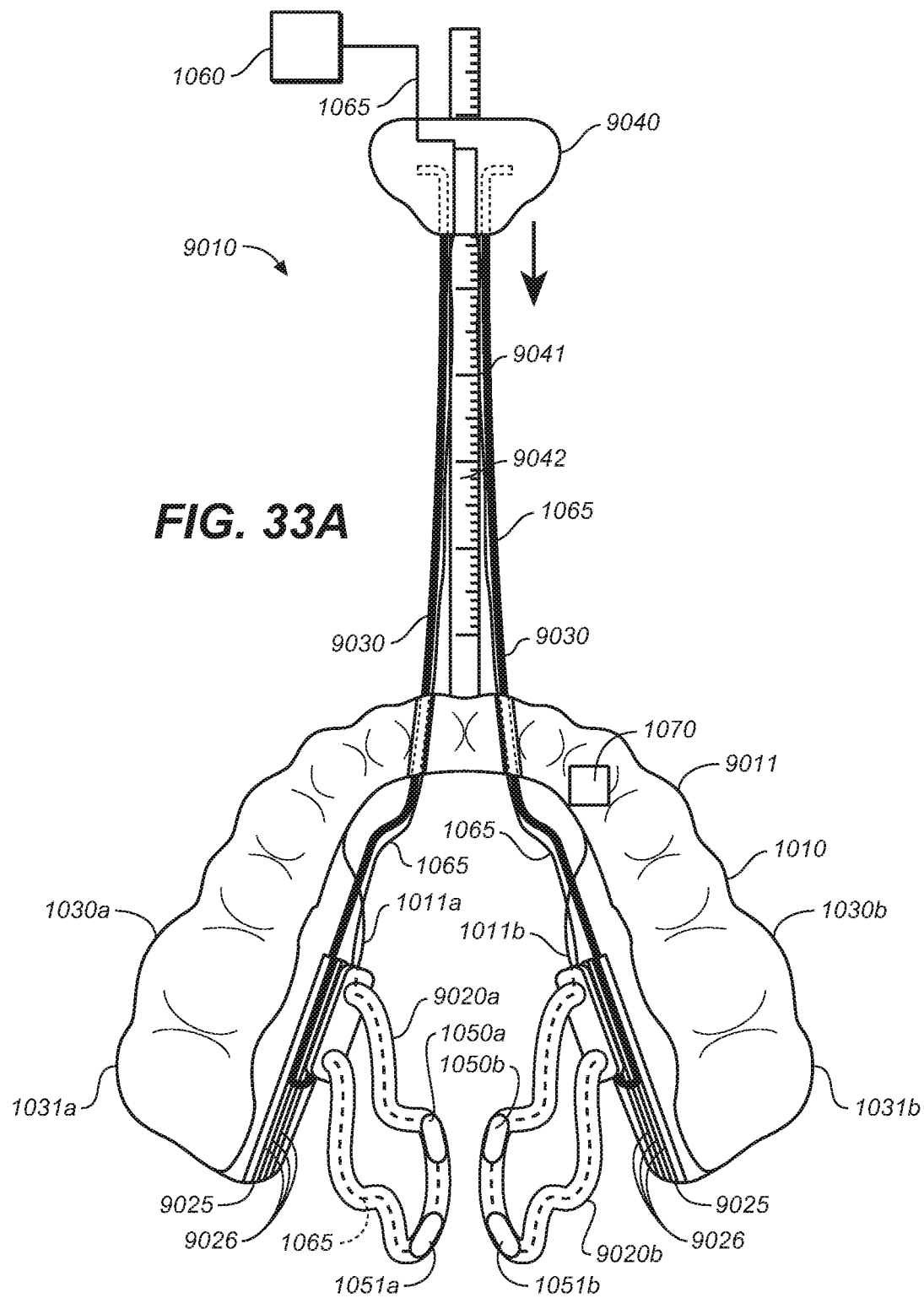
FIG. 33A is a bottom plan view of an oral appliance in a first anterior-posterior position and configured in accordance with representative embodiments of the present technology.

FIGS. 33A to 33E illustrate an intraoral stimulation response test device 9010 configured in accordance with representative embodiments of the present technology. Referring first to FIG. 33A, the test device 9010 includes multiple electrodes (e.g., four) 1050a, 1051a, 1050b, 1051b that can be moved to a plurality of positions. Electrical stimulation can be applied to the patient via electrodes in different electrode positions to create a variety of detectable responses. Accordingly, the test device 9010 can allow the practitioner and or an automated system component to identify one or more desirable electrode positions and/or locations based on the patient's response to the electrical stimulation. The intraoral stimulation device for patient use can be manufactured to have similar dimensions, electrode positions and/or orientations identified as being desirable, using the test device 9010. The information obtained via the test device 9010 can be used to manufacture an intraoral stimulation device, such as, for example, any of the devices described with respect to FIGS. 1-32 and 37A-37C herein. The test device may also be used to identify desired electrical stimulation parameters or programs, as is also described herein. The extensions can be flexible, as discussed above, or generally rigid. In either case the extensions can support one or more corresponding electrodes. The extensions can also move along one or more constrained guide paths, and, because the extensions carry one or more electrodes, can position the electrodes at one or more selected locations. In such instances, the a particular position of an electrode has a corresponding position of the extension. In other embodiments, the test device can include other arrangements for moving the electrodes in a constrained manner, for example, without an extension.

The test device 9010 can include a removeable intraoral appliance 9011 having an attachment body 1010 to engage, secure and/or anchor the test device 9010 within the oral cavity. Examples of representative embodiments of an attachment body that can be used with a test device are described, for example, with reference to FIGS. 1-32 herein. In accordance with some representative embodiments of the present technology, the body 1010 can include one or more lateral portions or lateral segments 1030a, 1030b having posterior, inferior molar portions 1031a, 1031b with or without posterior rigid flaps 1011a, 1011b. A first extension 9020a and a second extension 9020b can be coupled on laterally opposing sides of the body 9010, e.g., to the flaps 1011a, 1011b. The moveable extensions 9020a, 9020b include distally located electrodes 1050a, 1051a, 1050b, 1051b that move with the extensions 9020a, 9020b.

In some embodiments, the attachment body 9010, flaps 1011a, 1011b and/or extensions 9020a, 9020b can have a similar construction (including but not limited to similar flexible and resilient properties) as the appliance that the patient will ultimately use. With similar properties, the test device 9010 can generally simulate the placement and movement of the final device in use. The moveable extensions 9020a, 9020b as shown, are configured similar to the extensions 6040a, 6040b described with reference to FIGS. 16-23B herein. However, in representative embodiments, other extension configurations can be used, including, but not limited to those described with respect to any of the representative embodiments shown in FIGS. 1-37C herein.

The extensions 9020a, 9020b are attached to positioning elements 9030 that are manipulable with a handle 9040. In other embodiments, the positioning member can be controlled by an actuator, e.g., a motor, solenoid, and/or other device, rather than by hand, for example, as described further below with reference to FIGS. 38A-38D. In a particular embodiment, the positioning members 9030 move the extensions 9020a, 9020b relative to guide elements 9025 carried by the flaps 1011a, 1011b. The guide elements 9025 can be configured to permit the extensions to move in a controlled manner in one or more directions. In accordance with some embodiments of the present technology, the guide elements 9025 can each include one or more grooves 9026 that slidably receive a corresponding positioning member 9030. The one or more grooves 9026 allow the positioning member 9030 to move in posterior and anterior directions to correspondingly move the electrodes 1050a, 1051a, or 1050b, 1051b in posterior and anterior directions. According to some embodiments of the technology, the positioning members 9030 are (or include) wire or rod-like elements. The positioning members 9030 can be configured to exit the oral cavity and be coupled to the handle 9040. The handle 9040 can be actuated to advance or retract the positioning members 9030, and thus the attached extensions 9020a, 9020b and associated electrodes, in a posterior direction and anterior direction. Accordingly, the extensions 9020a, 9020b can move the electrodes 1050a, 1051a, 1050b, 1051b to a plurality of posterior-anterior positions within the patient's oral cavity. The handle 9040 can be coupled to a position indicator 9041 that includes indicia 9042 identifying the anterior-posterior position of the extensions 9020a, 9020b and electrodes 1050a, 1051a, 1050b, 1051b.

Figure 33B:
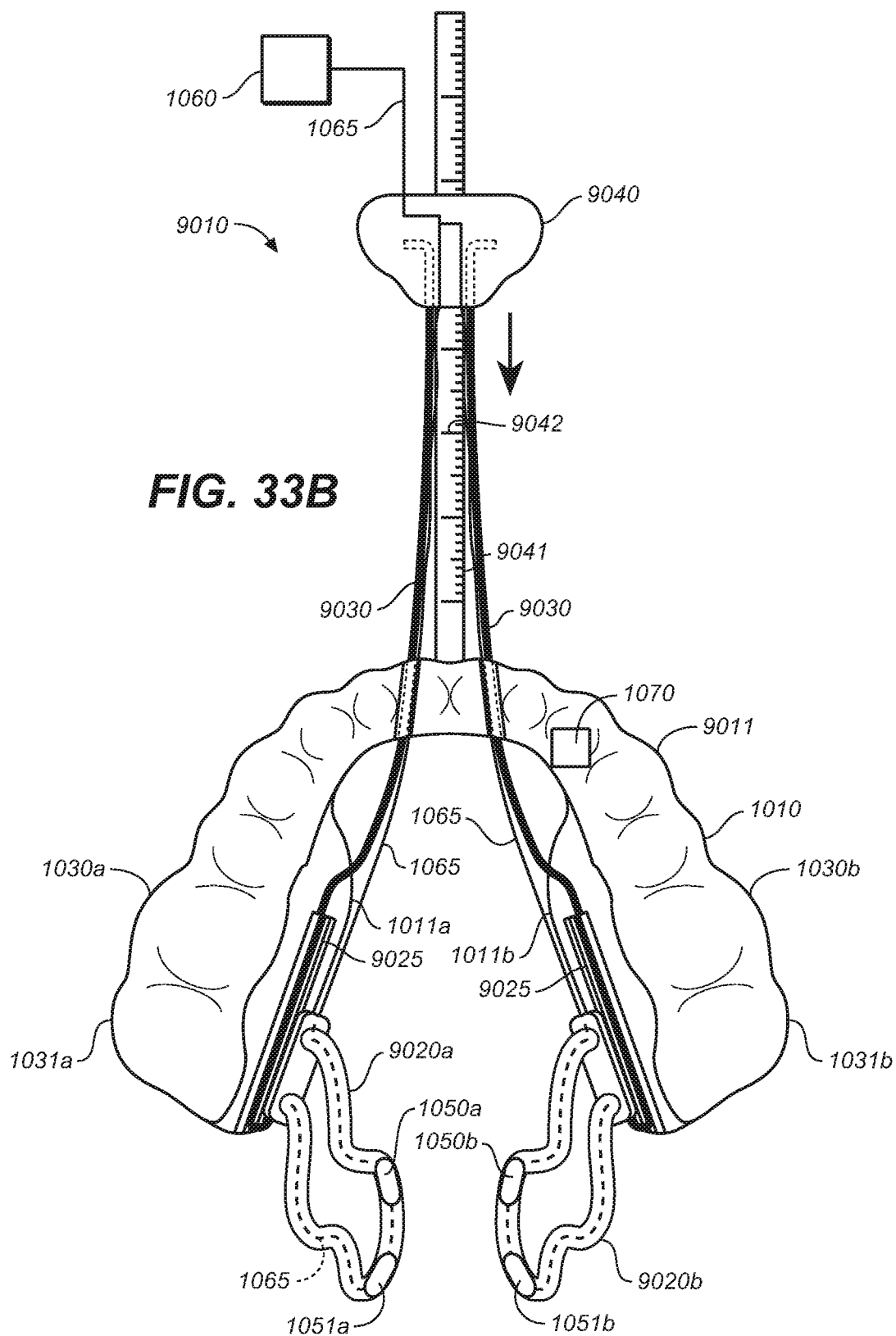
FIG. 33B is a bottom plan view of the oral appliance of FIG. 33A in a second anterior-posterior position.
Figure 33C:
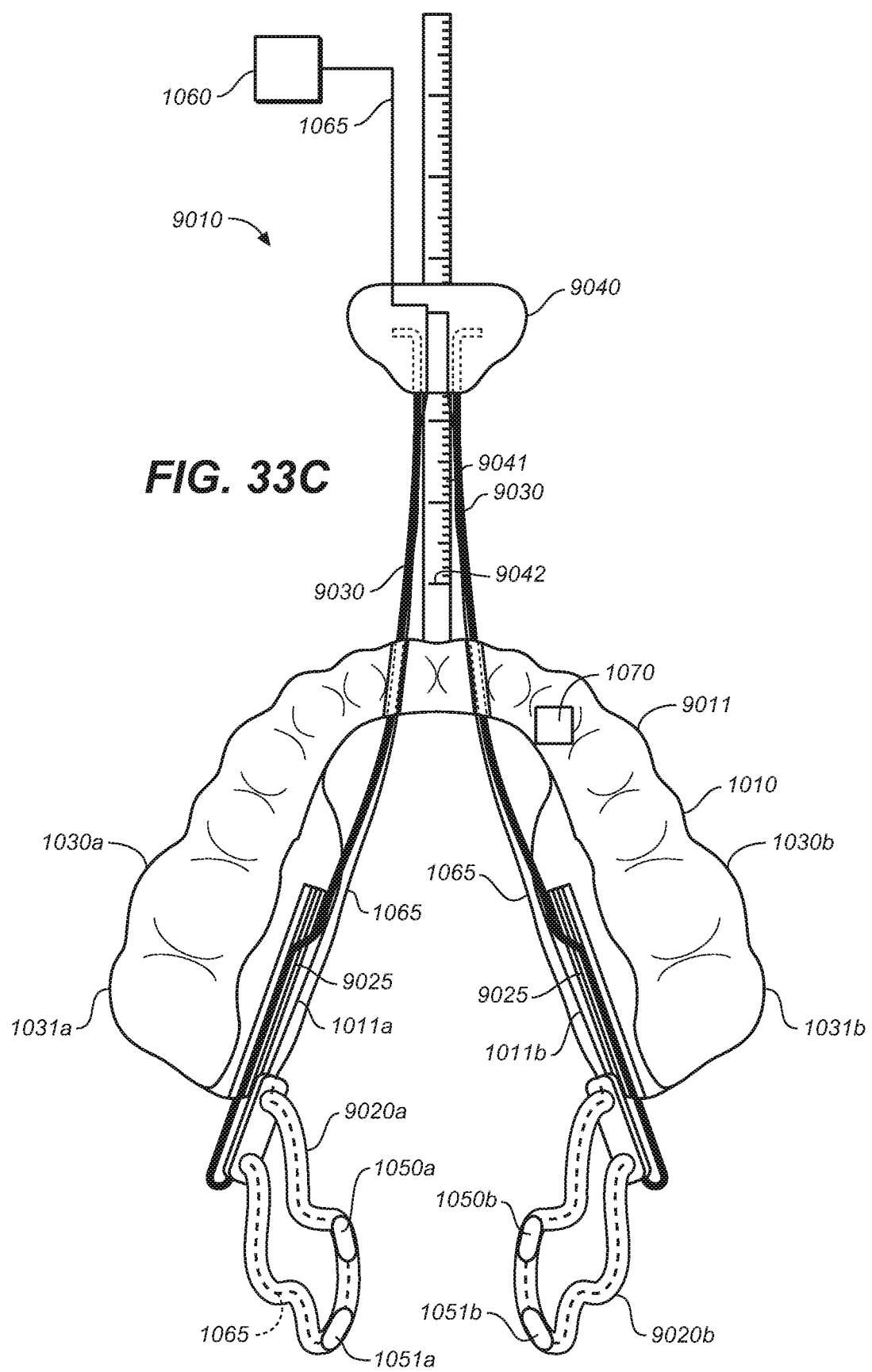
FIG. 33C is a bottom plan view of the oral appliance of FIG. 33A in a third anterior-posterior position.

FIG. 33A shows the positioning members 9030 in a first position with the extension members 9020a, 9020b and associated electrodes in a generally anterior position. FIG. 33B shows the positioning members 9030 (along with the extension members and 9020a, 9020b and electrodes)

advanced to a more posterior position. FIG. 33C shows the positioning members 9030 advanced to yet a more posterior position.

Figure 33D:
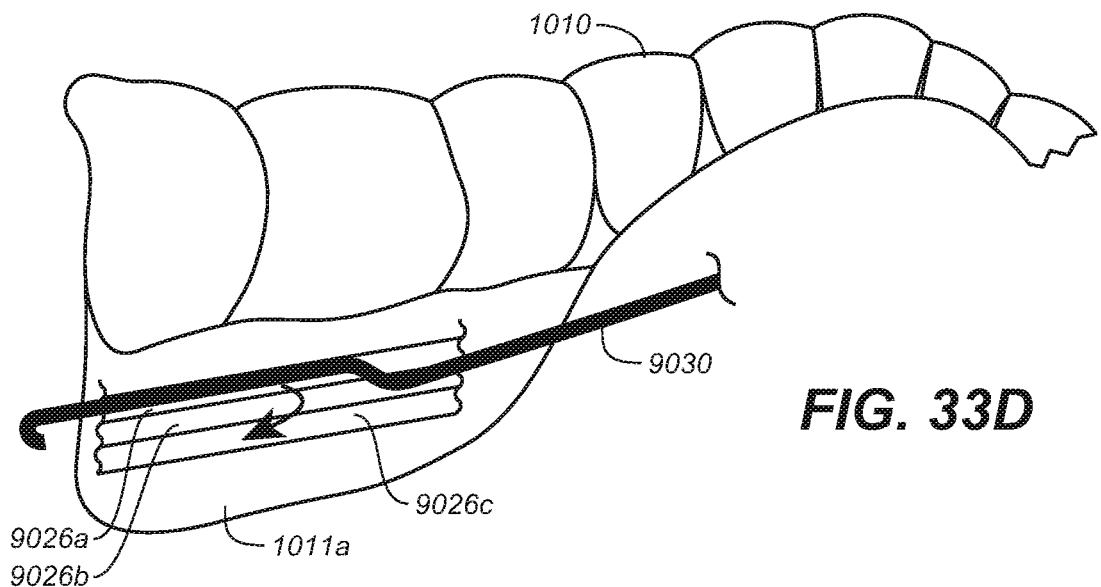
FIG. 33D is an elevated perspective view of a portion of the oral appliance of FIG. 33A in a first superior-inferior position.
Figure 33E:
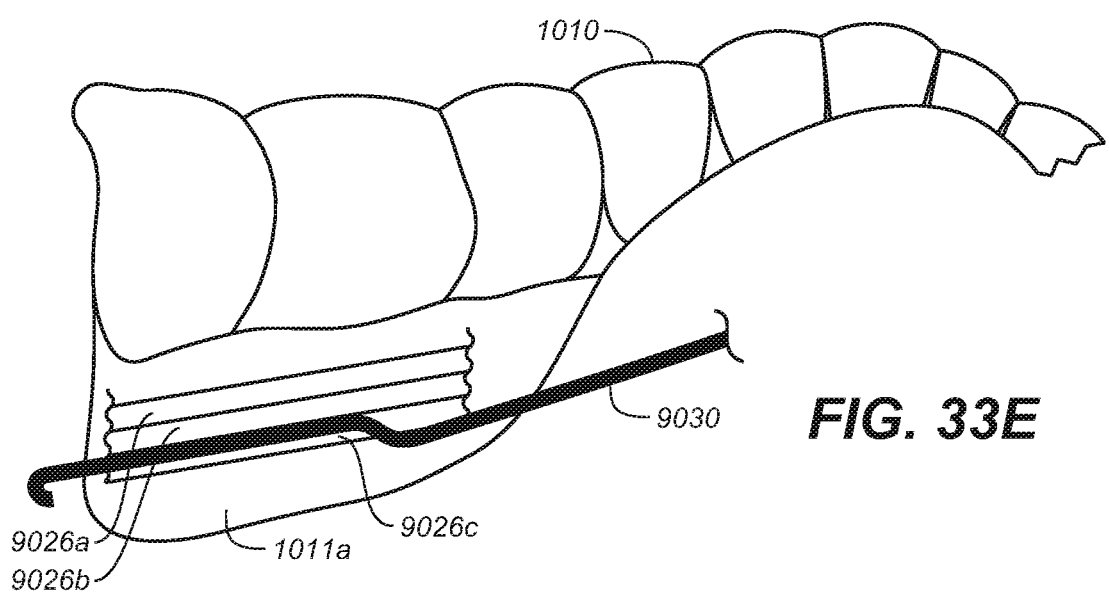
FIG. 33E is an elevated perspective view of a portion of the oral appliance of FIG. 33A in a second superior-inferior position.

According to some representative embodiments of the present technology, the electrodes can also be moveable to different inferior-superior positions. The grooves 9026 shown in more detail in FIGS. 33D and 33E as first, second and third grooves 9026a, 9026b, 9026c, are spaced in superior-inferior directions (e.g., along a generally superior-inferior axis) with respect to each other. The positioning elements 9030 can be placed in a predetermined one of the plurality of grooves 9026 to select a superior-inferior position of the corresponding electrodes 1050a, 1051a, 1050b, 1051b (FIG. 33C). FIG. 33D illustrates a positioning element 9030 in the more superior first groove 9026a. FIG. 33E illustrates the positioning element 9030 in the more inferior third groove 9026c. In some representative embodiments, the medial-lateral position of the electrodes can also be varied with the test device. For example, the grooves 9026 can also place the positioning elements 9030 in different medial-lateral positions with respect to each other. In other embodiments the media-lateral position can be adjusted independently of the superior-interior position.

Referring back to any of FIGS. 33A-33C, the test device 9010 also comprises electrical connections 1065 that couple the electrodes 1050a, 1051a, 1050b, 1051b to the electronics circuit 1060. The electrical connections 1065 can be in the form of wires that extend along or within the positioning members 9030, and exit the oral passageway where they can be connected to the electronics circuit 1060. The electronics circuit 1060 provides electrical stimulation to the oral cavity by way of the electrodes. The electrical stimulation provided by the electronics circuit of the test device 9010 can model the stimulation to be provided by a longer-term intraoral stimulation device, as described in FIGS. 1 to 32 herein.

In use, the test device 9010 is positioned in the oral cavity and the practitioner, other user, and/or a program selects an initial electrode position. The indicia 9042 can be used to identify the posterior-anterior electrode position. The electrode position may additionally be identified by the particular groove 9026 in which the positioning member 9030 is placed. The practitioner, other user, and/or program applies electrical stimulation and detects the patient's response. The response can be detected, for example, by visualizing the oral cavity, tongue movement, and/or patency of the upper airway, for example, using a nasal endoscope. An instrument can be used to monitor pressure and/or flow resistance. The test device itself or another instrument can include sensors 1070 to determine the patient's stimulation response in a manner similar that described with respect to FIGS. 1-32. Other indicators of efficacy can also be used, for example, by determining the apnea-hypopnea index (AHI). Electrical stimulation parameters can also be varied and the response observed.

The test devices described herein, or elements thereof can be incorporated into the final end user intraoral stimulation device. The intraoral stimulation devices described herein can also be interchangeably used as test devices. In addition, different features of the intraoral stimulation devices described herein can also be used in test devices, as described further below.

Figure 34A:
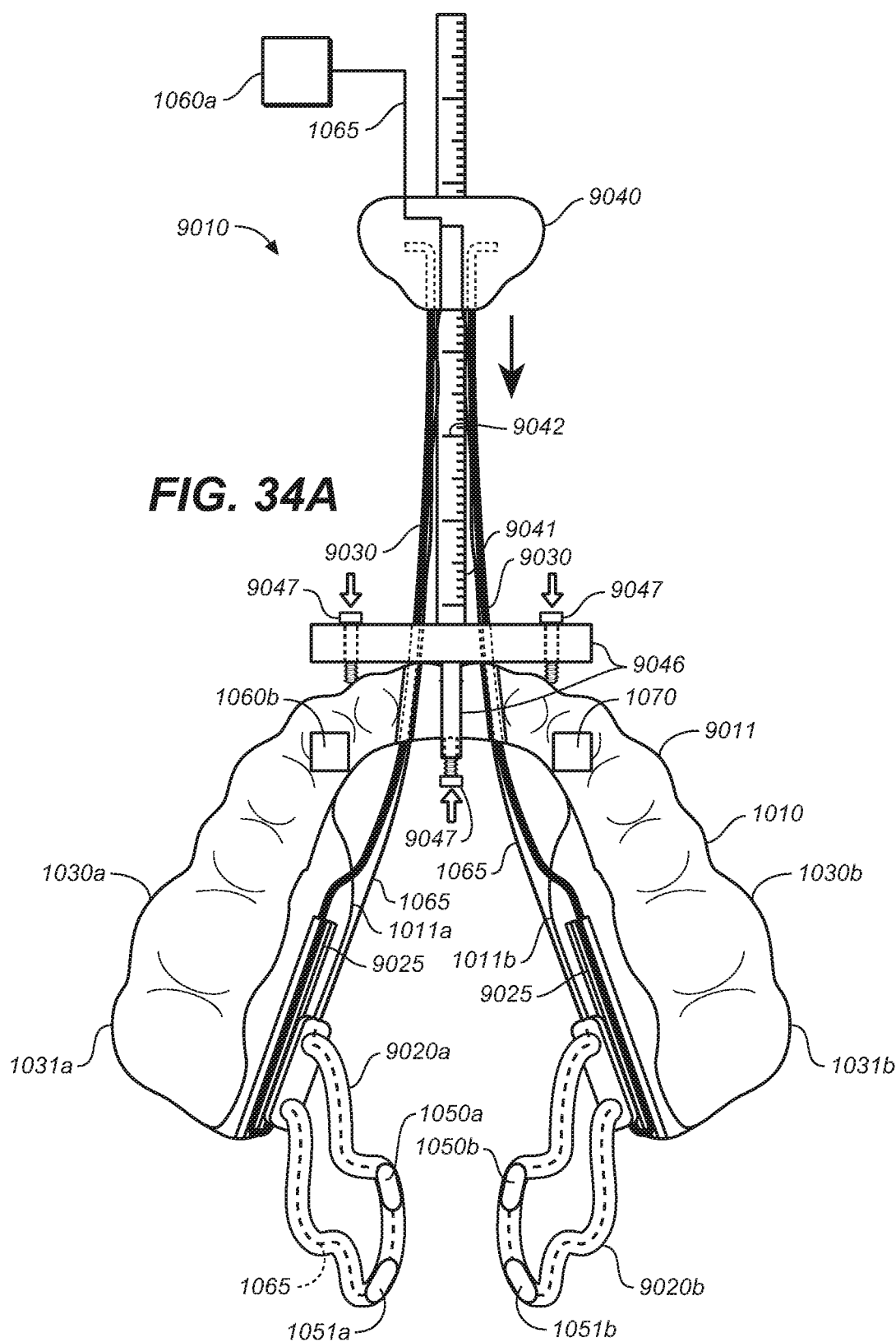
FIG. 34A is a bottom plan view of an oral appliance with a removeable handle configured in accordance with representative embodiments of the present technology.
Figure 34B:
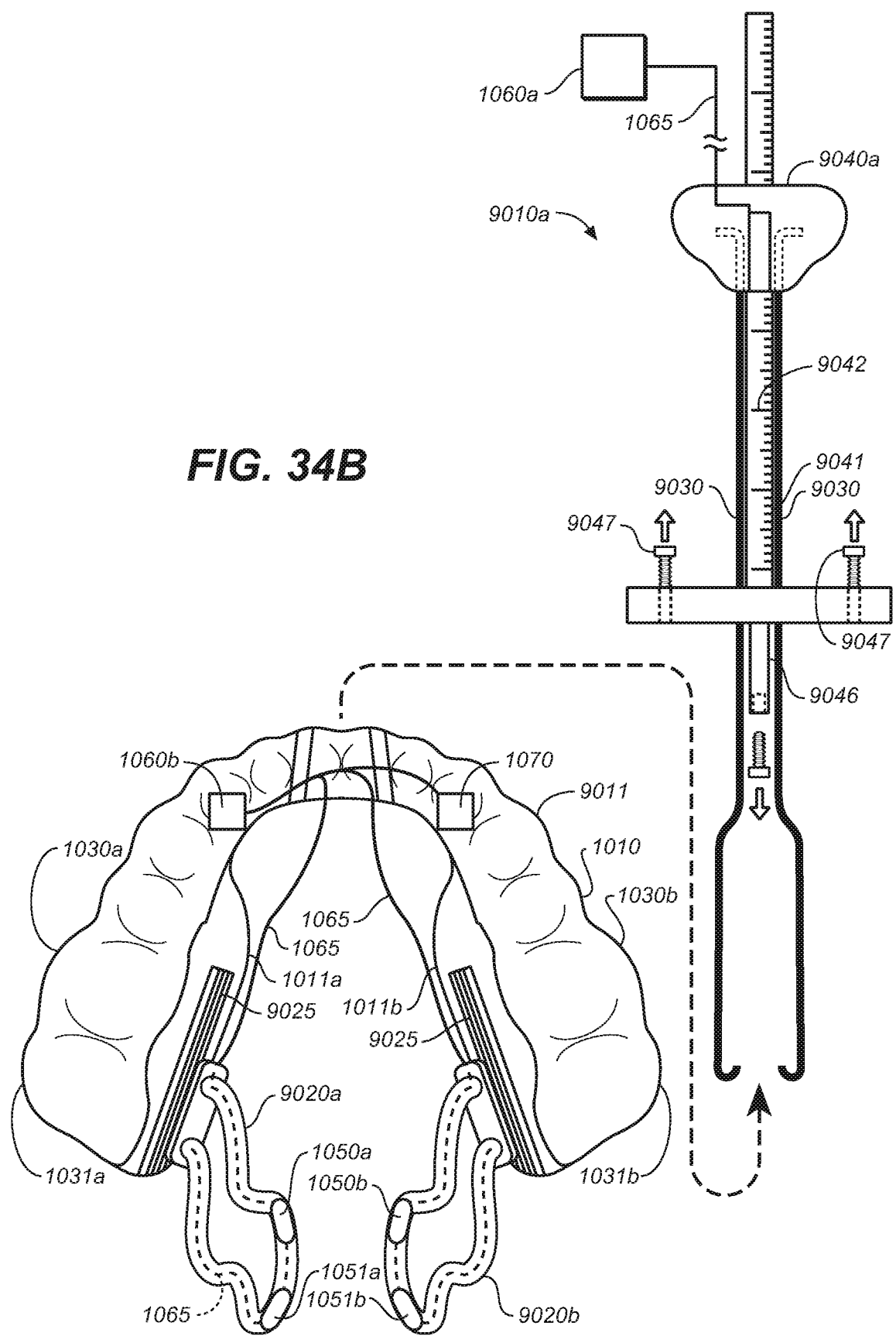
FIG. 34B is a bottom plan view of the oral appliance of FIG. 34A with the removeable handle disconnected from the appliance

FIGS. 34A and 34B illustrate an intraoral stimulation device with a detachable handle 9040a that can allow the device 9010a to be converted from a test device to a stand-alone intraoral stimulation device. Accordingly, the same device, or elements of the same device, can be used in both a first (e.g., test) phase, and a second (e.g., long term or chronic) phase. Such a device can, in the second phase, provide therapy to the patient for an extended period of time (e.g., weeks, months or years).

For example, in a representative embodiment, the device 9010a can include a detachable handle 9040a connected to the body 1010 of the device, and can include positioning elements 9030. Extensions 9020a 9020b are removably secured to the positioning elements 9030. The handle 9040a is removably attached to the body 1010, for example with attachment elements 9046, 9047. Attachment elements 9047 are illustrated as set screws. However, other suitable attachment elements (e.g., including adhesives) can be used. A first (e.g., extraoral) electronics circuit 1060a external to the patient's intraoral cavity can be connected by way of connectors 1065 to the electrodes 1050a, 1051a, 1050b, 1051b. According to some representative embodiments, alternatively or additionally, a second electronics circuit 1060b may be provided on the body 1010 of the device as described with respect to FIGS. 1-32. After testing and determining the desired electrode positions as described with respect to FIGS. 33A-33E, the handle 9040a and positioning elements 9030 can be detached from the body (FIG. 34B), e.g., as a unit. If an electronics unit 1060b is located on the body 1010, when the handle 9040a is detached (FIG. 34B), the connectors 1065 coupled to the electronics elements contained in the first electronics circuit 1060a can be disconnected. The extensions 9020a, 9020b can then be secured to body 1010 in the desired locations, for example using attachment mechanisms such as adhesives and/or mechanical attachment elements. The electrodes 1050a, 1051a, 1050b, 1051b if not yet connected, can then be electrically connected to the second electronics circuit 1060b on the body 1010. The device can then be used as an intraoral appliance as described in FIGS. 1-30 and 37A-37C.

Figure 35A:
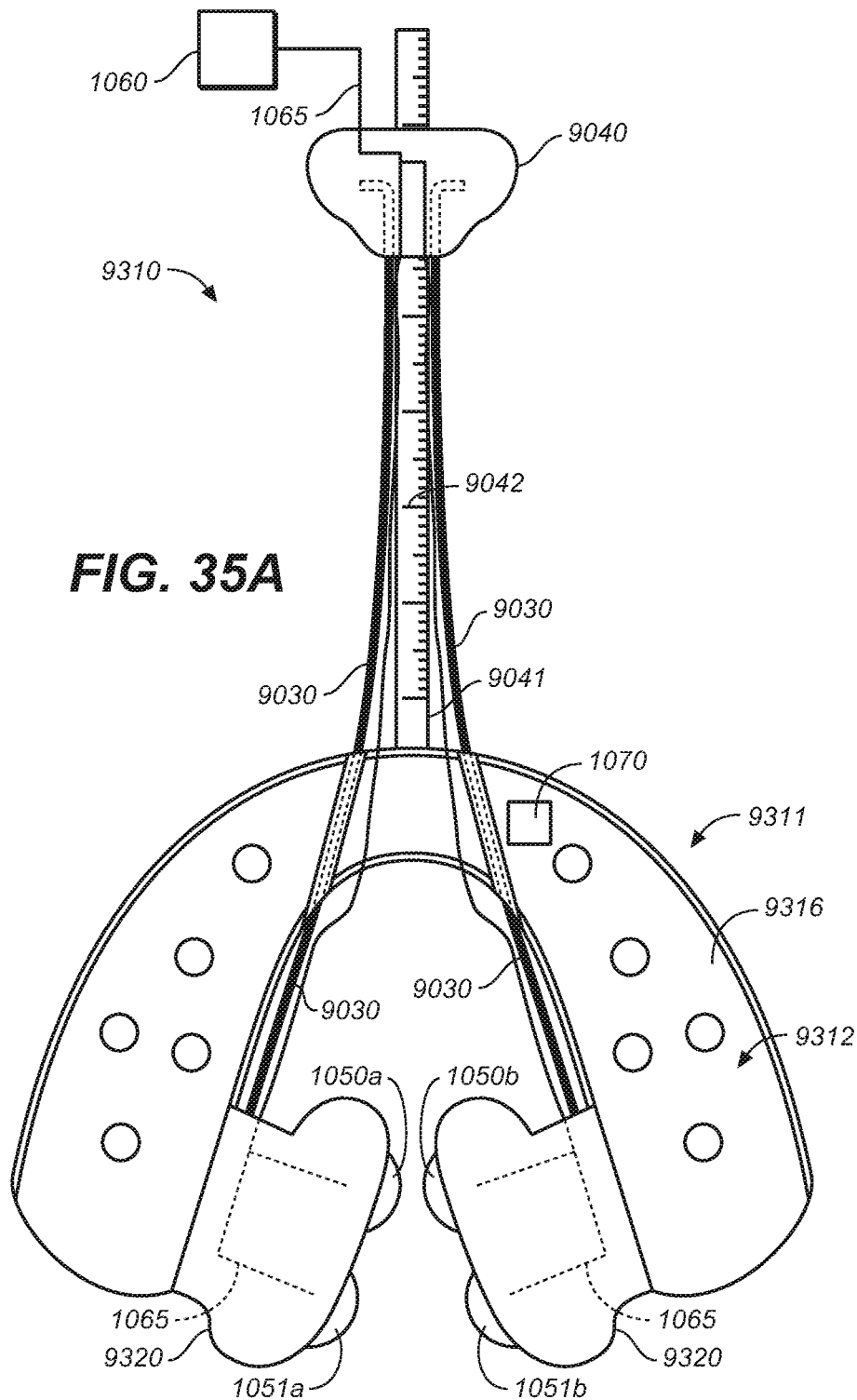
FIG. 35A is a bottom plan view of an oral appliance in a first anterior-posterior position in accordance with representative embodiments of the present technology.
Figure 35B:
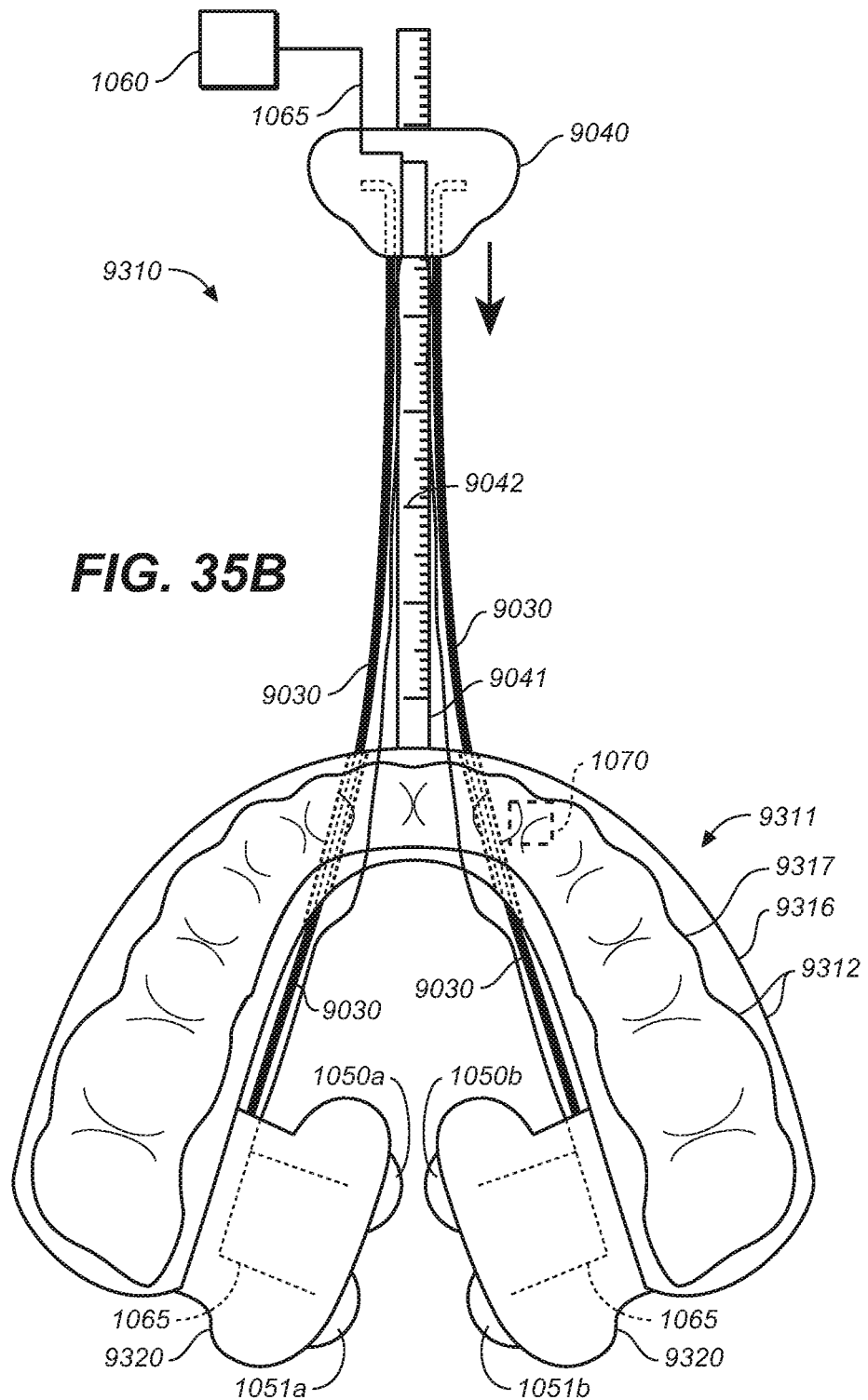
FIG. 35B is a bottom plan view of the oral appliance of FIG. 35A in the first anterior-posterior position and with a teeth-securing insert.
Figure 35C:
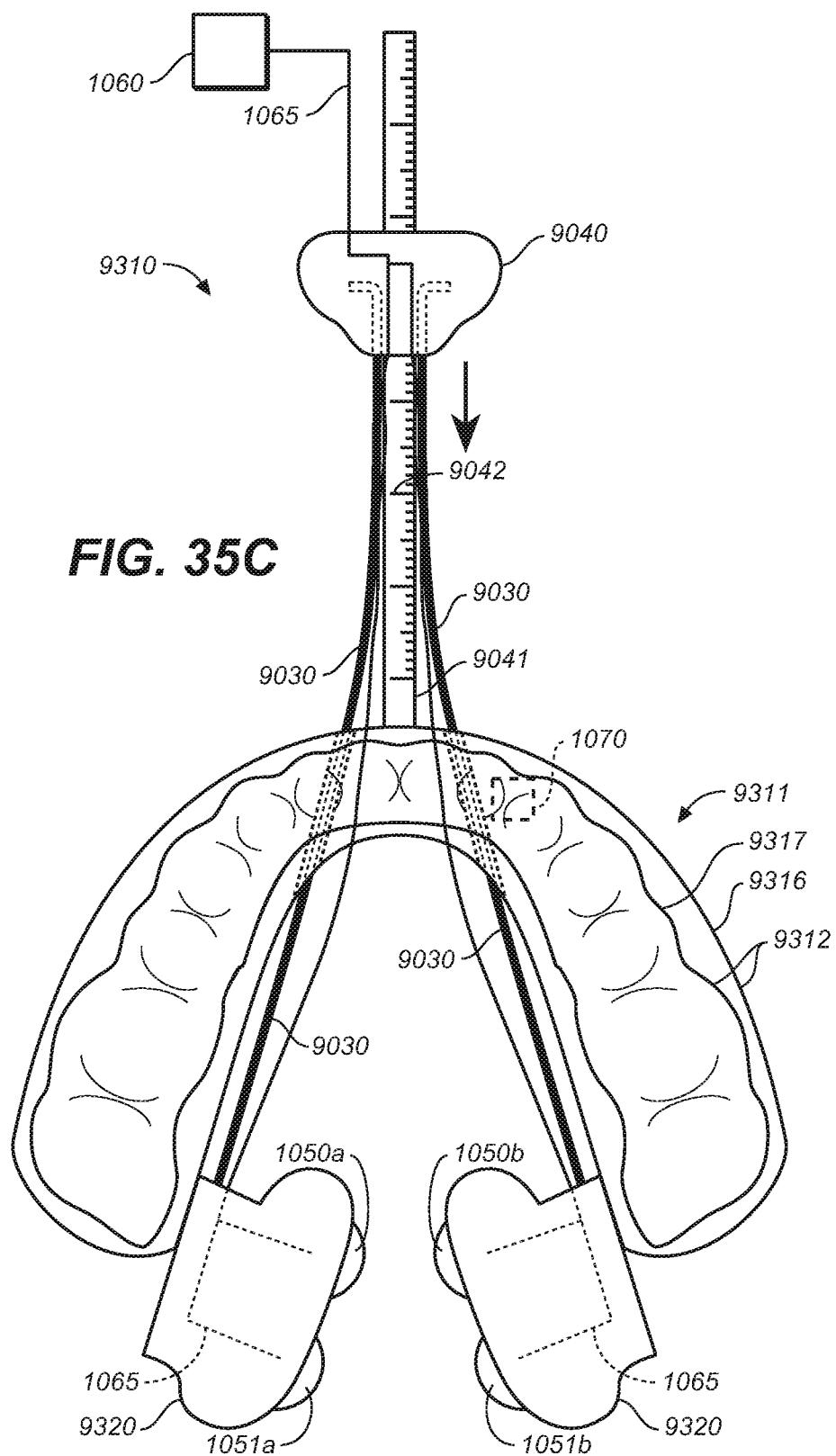
FIG. 35C is a bottom plan view of the oral appliance of FIG. 35B in a second anterior-posterior position.
Figure 35D:
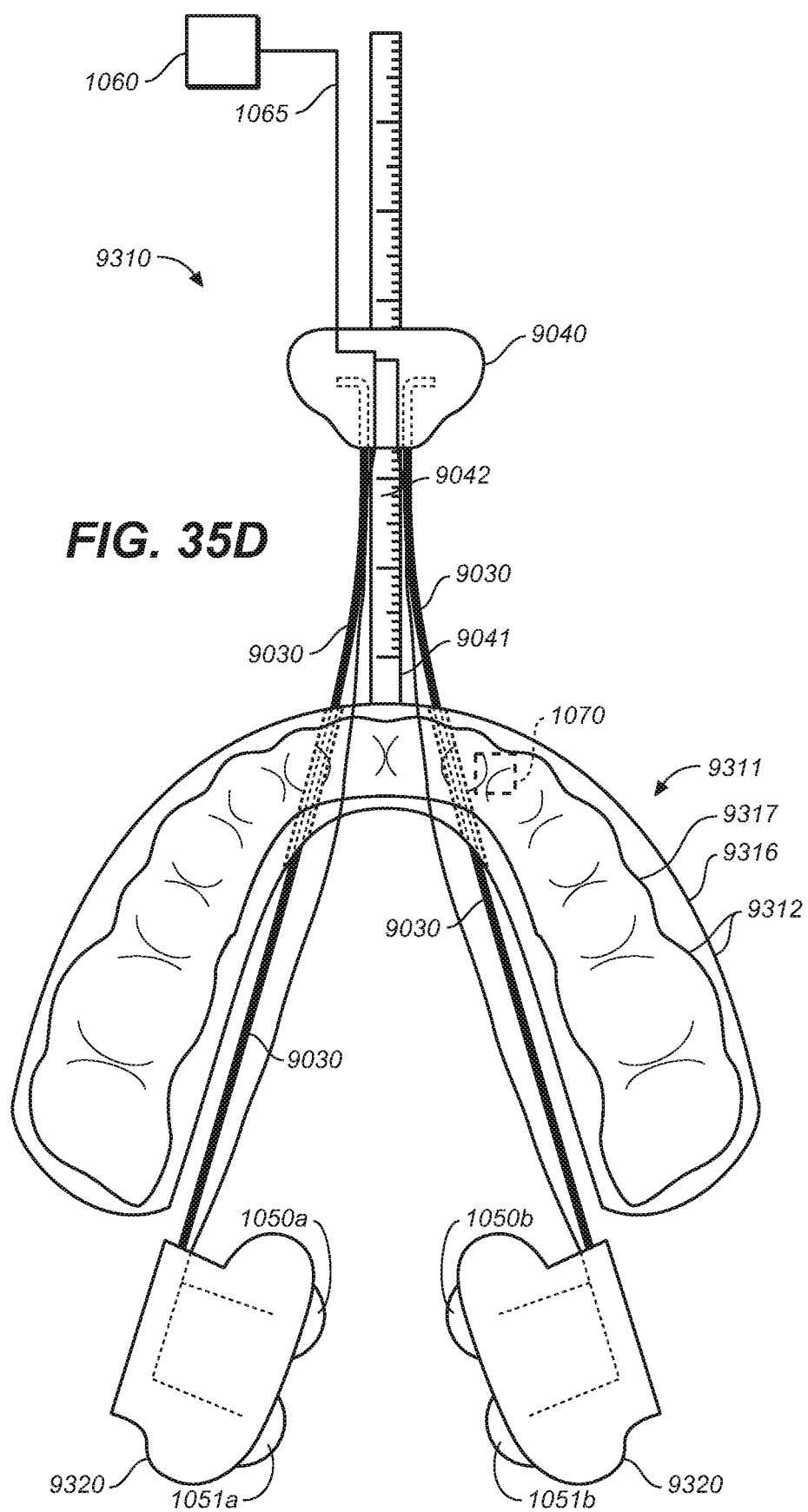
FIG. 35D is a bottom plan view of the oral appliance of FIG. 35B in a third anterior-posterior position.

FIGS. 35A-35D illustrate an intraoral stimulation response test device 9310 according to representative embodiments of the present technology. The test device 9310 comprises positioning elements 9030 that can be attached to moveable extensions 9320. The extensions 9320 each have one or more electrodes 1050a, 1051a, 1050b, 1051b to electrically stimulate tissue within the patient's oral cavity. The positioning elements 9030 can also be attached to a handle 9040, and can have indicia 9042 showing the anterior-posterior position of the electrodes 1050a, 1051a, 1050b, 1051b. The test device 9310 comprises an intraoral appliance 9311 having an attachment body 9312 (FIGS. 35B-35D) configured to engage, secure and/or anchor the appliance 9311 to teeth of the lower arch within the oral cavity. The attachment body 9312 can comprise a base 9316 (FIGS. 35A-35D) and a customized insert 9317 (FIGS. 35B-35D). The base 9316 can be of a generic size that fits the oral cavities of number of patients. The base may be manufactured in multiple generic sizes to fit multiple groups of patients. As shown in FIGS. 35B-35D, the customized insert 9317 can be attached to the base 9316 with the customized insert 9317 comprising an individualized mouthpiece that fits a particular individual patient's teeth.

The positioning elements 9030 can be actuated by the handle (or other manipulation device) 9040 to advance or retract the positioning elements 9030 and attached extensions 9320 in posterior-anterior directions, with the indicia indicating the posterior-anterior position or location of the electrodes. Similar to the device shown in FIGS. 33A to 33E, in use, the electrodes 1050a, 1051a, 1050b, 1051b can be positioned in a variety of locations to obtain feedback that can be used to manufacture an intraoral stimulation device with desired dimensions and electrode positions.

FIG. 35A illustrates a test device 9310 without an insert 9317. FIGS. 35B-35D illustrate the test device with the insert 9317. As shown in FIG. 35B, the positioning member 9030 is in a first position with the extension members 9320 and electrodes 1050*a*, 1051*a*, 1050*b*, 1051*b* in a more anterior position. FIG. 35C shows the positioning member 9030, extension members 9320 and electrodes 1050*a*, 1051*a*, 1050*b*, 1051*b* advanced to more posterior positions. FIG. 35D shows the positioning member 9030 advanced along with the extension members 9320 and electrodes 1050*a*, 1051*a*, 1050*b*, 1051*b* to a yet more posterior position.

The customized insert 9317 can be conveniently molded when the patient is present for testing. Creating a molded insert at the time the patient is present for testing may reduce the number of patient visits and associated professional time. However, a generic base may not match the dental arch of a patient as precisely as a custom appliance body. Thus, the specific location of the electrodes and extensions might not correspond as accurately to the patient as a custom appliance body. More rigid extensions, for example, as shown in FIGS. 35A-35D, may more readily identify specific locations for electrode placement as they do not flex, move or displace as much with the mouth and tongue movement of a patient in response to electrical stimulation. However, the extensions of the test device may not match the flexibility of the final oral appliance. According to embodiments of the present technology, alternatively configured extensions may be used, including but not limited to those described with reference to FIGS. 1-34B and 36A to 37C herein.

Figure 36A:
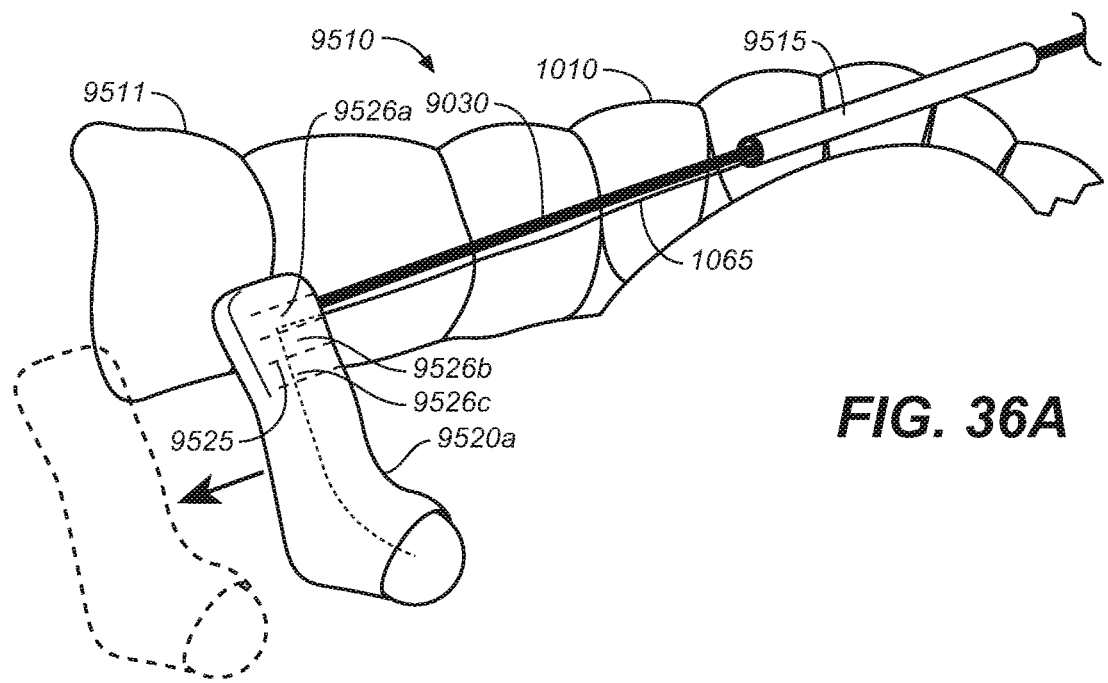
FIG. 36A is an elevated perspective view of a portion of an oral appliance having a removeable extension member and electrode configured in accordance with representative embodiments of the present technology.
Figure 36B:
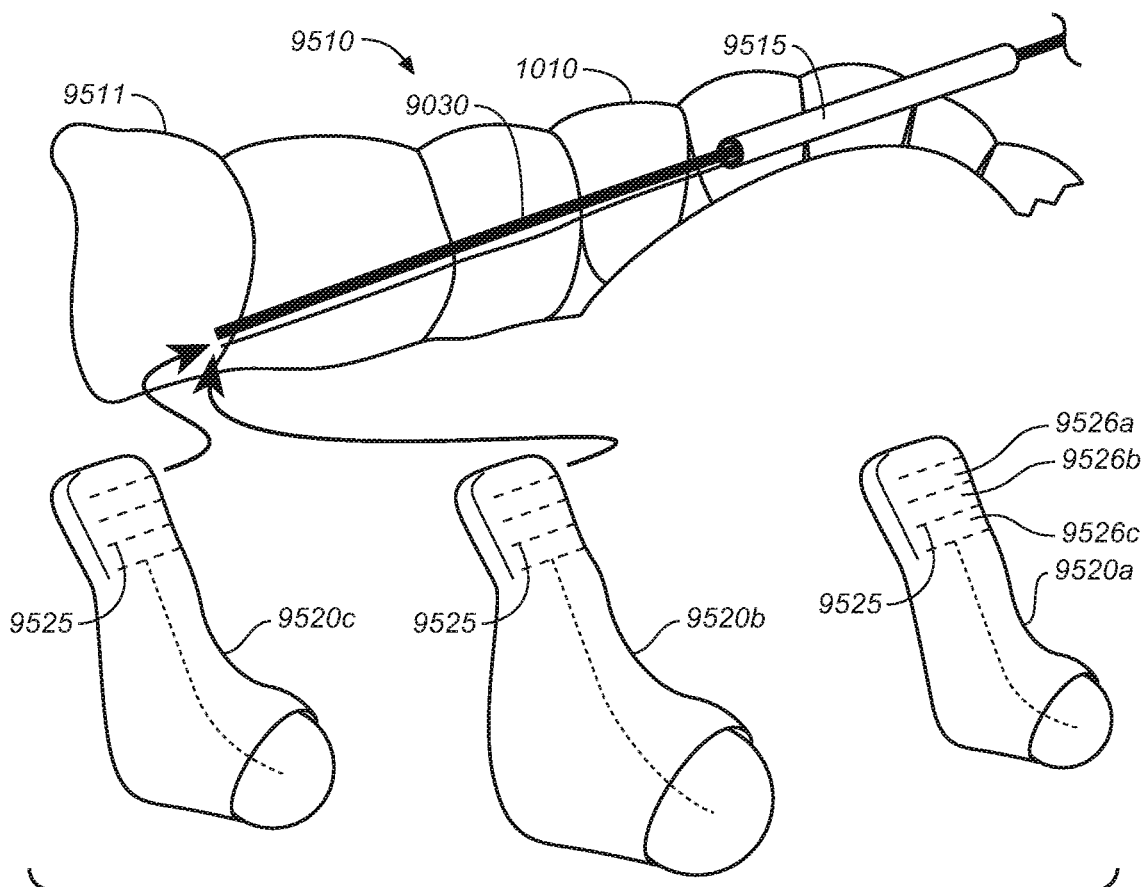
FIG. 36B is an elevated perspective view of a portion of the oral appliance of FIG. 36A with a plurality of removeable extension members and electrodes configured in accordance with representative embodiments of the present technology.

FIGS. 36A and 36B illustrate an intraoral stimulation response test device 9510 according to some embodiments of the present technology. The test device 9510 comprises a removeable intraoral appliance 9511 including an attachment body 1010 to engage, secure or anchor the test device within a patient's oral cavity. The test device 9510 comprises a positioning element 9030 that extends from a handle 9040 (FIGS. 35A-35D) outside the oral cavity, posteriorly into the oral cavity, and through a guide 9515 attached to the body 1010. The guide 9515 can include a tube that permits and guides movement of the positioning element 9030 in generally posterior-anterior directions. The test device 9510 includes a plurality of selectable removeable and moveable electrode supports that can act as extensions 9520*a*, 9520*b*, 9520*c*, referred to collectively by reference number 9520. Each extension 9520 comprises at least one distally located electrode 1050*a* that moves with the extension. The extensions 9520 have proximally located attachment structures 9525 that can removably attach the extension 9520 to the positioning element 9030. The positioning element 9030 can position the extensions 9520 in different posterior-anterior locations. The attachment structures 9525 can also be configured to position the extensions 9520 in different locations within the oral cavity. For example, the attachment structures 9525 can comprise a plurality of grooves or throughholes 9526 (three are shown as grooves 9526*a*-9526*c*) that allow different superior-inferior positions for attaching the positioning member 9030. The grooves 9526 can optionally have different medial-lateral spacing to allow for different medial-lateral electrode positions. Each extension 9520 can also have a different angular orientation, and/or medial-lateral electrode positions independent of the attachment structures. The extensions 9520 can also have a variety of shapes. Thus, the extensions 9520 and electrode 1050*a* can be positioned in different posterior-anterior, superior-inferior and/or medial-lateral positions, in addition to having different configurations, angular orientations and/or shapes. Different extensions can also have different flexing characteristics and directions of flex. Thus, the selectable extensions can also have different positions, shapes and/or flex characteristics, including but not limited to those described in FIGS. 1-35D and 37A-37C herein, thus providing more position and extension configuration parameters for evaluation.

In use, an extension can be selected from a plurality of extensions with known dimensions and material properties and can be attached to one of the grooves of the attachment structure. The posterior-anterior location or position can be selected and identified with positioning elements 9030 and handle 9040 (FIGS. 35A-35D) to test the patient's response to electrodes at different locations and/or with different extension configurations. After identifying a desired electrode position and extension configuration, the patient can receive a custom-manufactured intraoral stimulation device.

Figure 37A:
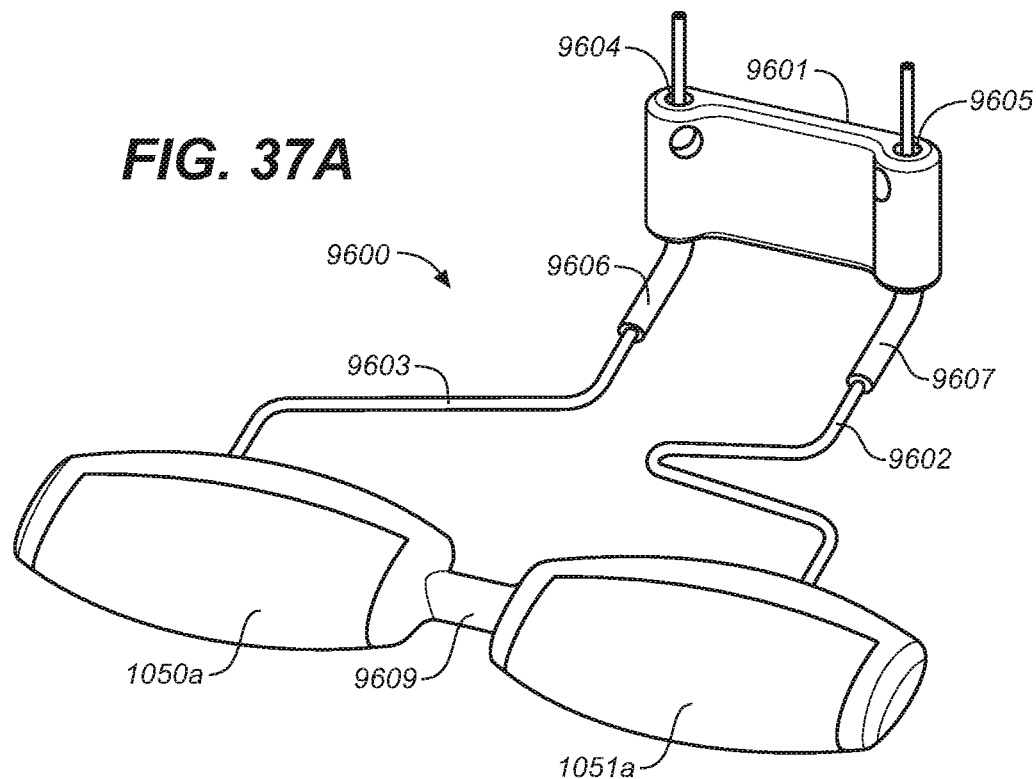
FIG. 37A is an elevated perspective view of an extension member configured in accordance with representative embodiments of the present technology.
Figure 37B:
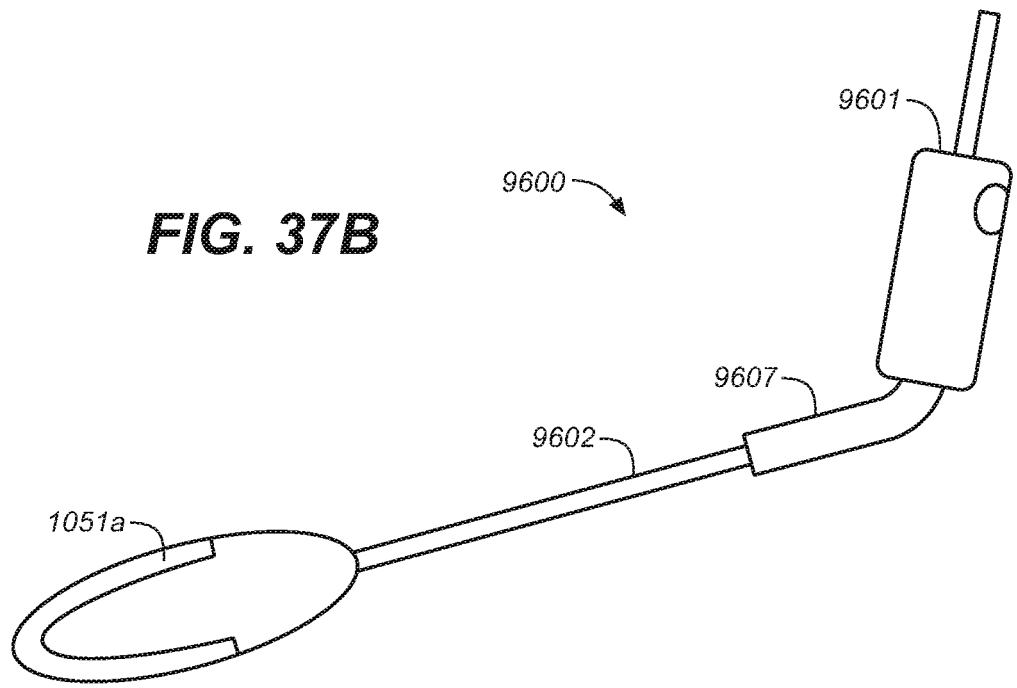
FIG. 37B is a side view of the extension member of FIG. 37A.
Figure 37C:
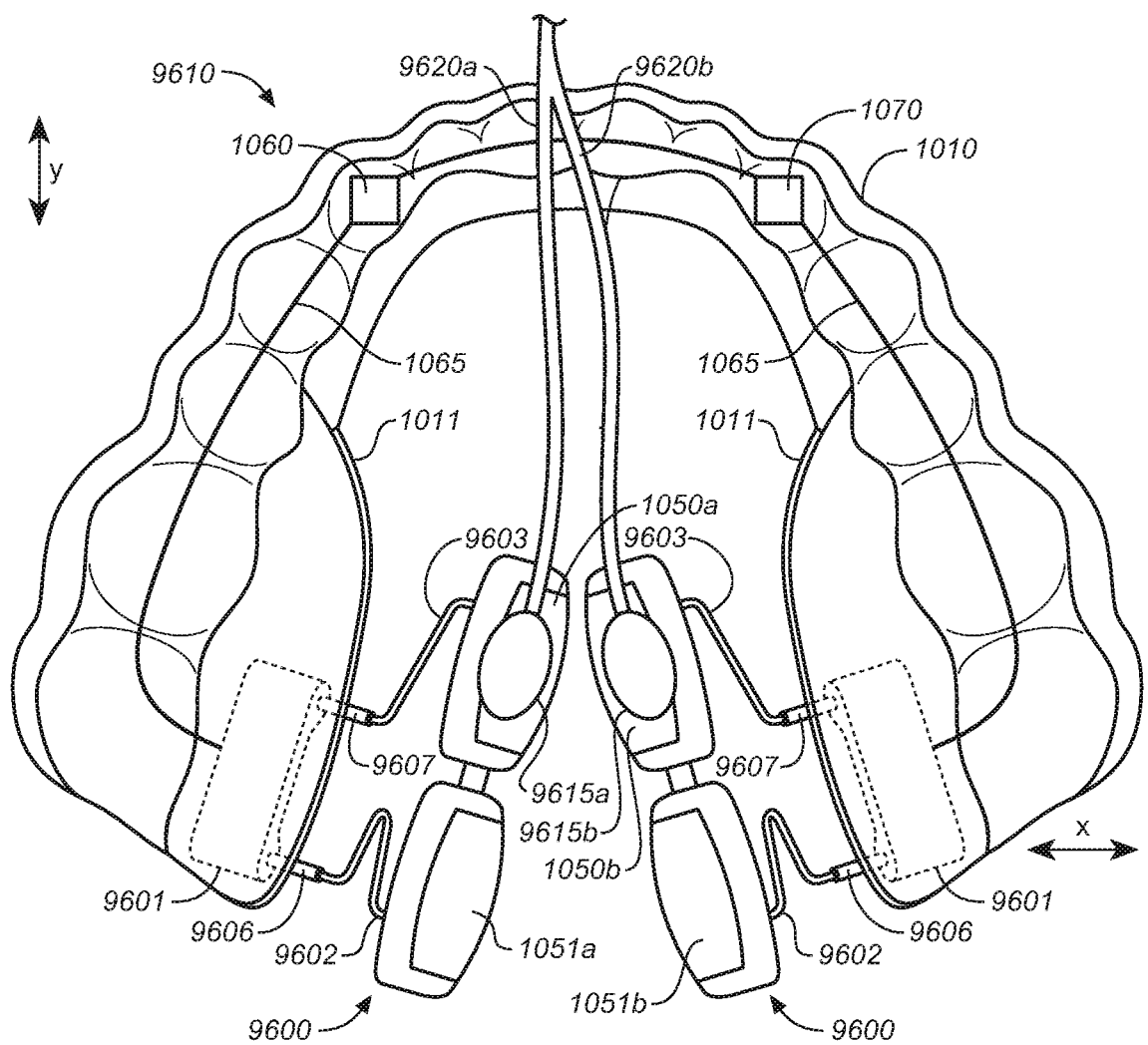
FIG. 37C is a bottom plan view of an oral appliance with the extension members of FIGS. 37A and 37B.

FIGS. 37A and 37B illustrate an adjustable extension 9600 that can be adjusted or customized for a particular patient. FIG. 37A is an isometric illustration of the extension 3600 and FIG. 37B illustrates a side view of the anterior portion of the extension. FIG. 37C illustrates an intraoral appliance with extensions 9600 installed. The extension 9600 can be used in an intraoral stimulation device and/or a test device. The extension 9600 can be coupled to a mouthpiece or attachment body 1010 (FIG. 37C) and positioned on a lateral side of the patient's oral cavity. An opposing extension 9600 can be positioned on an opposite lateral side of a patient's oral cavity and attached to the attachment body 1010. Each extension 9600 can be separately adjusted and customized for a particular patient. The laterally opposing extensions can be symmetric or different from each other, depending for example, on patient physiology.

Referring now to FIG. 37A, the extension 9600 comprises a mounting base 9601 that is coupleable to an attachment body. A posterior flexible resilient wire 9602 extends through a posterior opening 9604 in the mounting base 9601 and then through an angled tube 9606. A first electrode segment 1050*a* is attached at the distal end of the wire 9602. An anterior flexible resilient wire 9603 extends through an anterior opening 9605 in the mounting base 9601 and then through an angled tube 9607. A second electrode segment 1051*a* is attached at the distal end of the wire 9603. The electrode segments 1050*a*, 1051*a* can be generally flat, or can have other suitable shapes. The electrode segments 1050*a*, 1051*a* can extend in generally posterior to anterior directions. The electrode segments 1050*a*, 1051*a* are partially encased in a flexible material and linked by a flexible link 9609. The wires 9602, 9603 moveably extend or retract through the angled tubes 9606, 9607 to direct the wires 9602, 9603 in superior-inferior and medial-lateral directions to position the electrodes 1050*a*, 1051*a* different locations. Each wire 9602, 9603 can also be separately extended or retracted to vary the electrode locations. Accordingly, the wires 9602, 9603 can operate as positioning members, discussed above with reference to FIGS. 33A-36B. The angled tubes 9606 can be made of a deformable material, such as stainless steel. Accordingly, the extent to and/or the direction in which the tubes bend can be independently adjusted to adjust the angles of the wires and attached electrodes. The electrodes 1050*a*, 1051*a* are electrically connected to electronic circuitry 1060 (not shown in FIG. 37A). The patient's response to electrical stimulation can be observed with the electrodes at or in any of a variety of locations and positions to identify desired electrode positions. Once a desired position is identified, the wires can be fixed, for example using set screws, an adhesive, wire crimping and/or other suitable devices. The identified desired extension and electrode positions can also be used to manufacture a customized device for the patient.

In some representative embodiments, the electrodes can be generally flat to provide a greater surface area for tissue contact. While the electrodes are shown as being flat in this particular embodiment, in representative embodiments, other electrode shapes or configurations may be used, including for multiple electrode configurations. The flexible link 9609 between the electrodes can allow the flexibly linked electrodes 1050a, 1051a to conform to adjacent tissue and can permit some independent adjustment of the wires. The connecting elements 9025 shown in FIGS. 33A-34C and positioning elements 9030 shown in FIGS. 33A-35D can be used in a similar manner, and thus can allow posterior to anterior adjustments when testing desired extension and electrode positioning. The electrode placement may also be readjusted after use in the event the desired stimulation location shifts or if other changes are desired to improve comfort and/or performance.

In FIG. 37C, two extensions 9600 are illustrated attached to corresponding wings 1011 on the body 1010 of a representative appliance 9610. Two electrodes 1050a, 1051a are positioned on one extension 9600 so as to laterally oppose two corresponding electrodes 1050b, 1051b on the other extension 9600. In addition, inflatable bladders 9615a, 9615b are shown located at lateral locations on the extensions 9600. The inflatable bladders 9615a, 9615b can be used to position the electrodes medially, to provide greater electrode contact with the adjacent tissue, to create comfort, and/or to be used as pressure sensors. The inflatable bladders 9615a, 9615b are connected to inflation lines 9020a, 9020b which connect to a source for an inflation medium (not shown). If used as a pressure sensor, the sensors are coupled to the electronics 1060 by way of connectors 1065. The pressure sensors can also sense patient tongue movement which may be indicative of the effectiveness of the electrical stimulation. The inflation lines 9020a, 9020b may or may not be connected or linked. For example, if the lines 9020a, 9020b are independent, they can independently position the electrodes on each side and they can independently sense pressure. If the lines are connected, they can shift inflation medium from one side to the other, for example, when a patient shifts position, thus improving electrode contact on the side where the patient position where needed. If the lines are connected, a differential pressure between the bladders can indicate patient position. Inflatable bladders can be added to any of the extensions described in representative embodiments herein. Inflatable bladders may be added to any location on the intraoral stimulation device to improve electrode, appliance body positioning and or patient comfort.

The extensions and electrodes described in any of the Figures herein can also, in representative embodiments, be part of a test device in a manner as described with respect to FIGS. 33A-37C, in which electrode positions, stimulation parameters, and/or stimulation programs and/or algorithms can be tested prior to implementation.

According to some representative embodiments, the extensions of the test device can comprise a plurality of selectable electrodes, for example as shown and described with respect to FIGS. 7-12, 16-21B, 25, 33A-35D, and 37A-37C. According to some representative embodiments the test device can automatically select different electrode pairs and stimulation parameters to further identify desired electrode locations Many operations, including testing and use of the intraoral stimulation devices disclosed herein, can be performed by practitioner, patient, and/or may be automated or semi-automated, e.g. using software and/or computer logic to guide or control mechanical actuators and/or signal delivery. Representative embodiments of automated or semi-automated systems for moving electrodes during testing, screening, and/or therapy processes, are described below with reference to FIGS. 38A-38D.

FIG. 38A is a partially schematic illustration of an appliance or device 9700 having multiple electrodes 9750, two of which are visible, that are moved in an automated manner via one or more actuators 9731 (shown as a first actuator 9731a and a second actuator 9731b). The actuators 9731 themselves can be activated manually (e.g., via a simple switch), or automatically, for example, via a controller 9790 programmed with instructions for directing the actions of the actuators 9731. The instructions can be contained on computer-readable media, and can be executed via a wired or wireless transmission link between the controller 9790 and the actuators 9731.

In a particular embodiment, the actuators 9731 include servo or stepper motors, and the corresponding positioning T members 9730 (shown as a first positioning member 9730a and a second positioning member 9730b) can include cables. The actuators 9731 can move the positioning members 9730 axially, as indicated by arrows A. Accordingly, the first actuator 9731a can move the electrodes 9750 in an anterior-posterior direction, as indicated by arrow B. The second actuator 9731b can move the electrodes 9750 in a lateral or medial direction, as indicated by arrow C. The electrodes 9750 can be moved directly, and/or by moving an extension 9720 that carries the electrodes 9750. In any of these embodiments, the electrodes 9750 move relative to a corresponding attachment body 9710. For purposes of illustration, the actuator arrangements are shown in FIGS. 38A-38D are shown for only one side (the left side) of the device 9700. It will be understood that similar arrangements are suitable for both sides of the device.

Figure 38D:
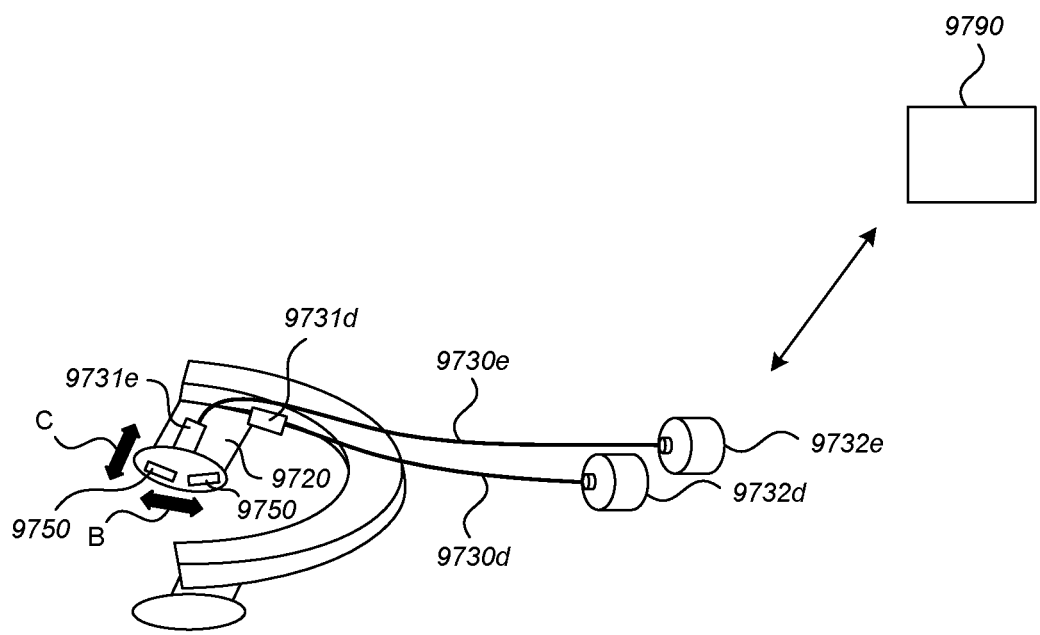
FIG. 38D is a schematic illustration of a device having electrodes that are moved via pneumatic or hydraulic actuators, in accordance with embodiments of the present technology.

FIGS. 38B and 38C illustrate another arrangement for moving the electrodes 9750 in a lateral or medial direction, indicated by arrow C. In this embodiment, the corresponding positioning member 9730c includes a bend 9732, and/or is otherwise rotatably coupled to the corresponding extension 9720, or directly to the electrodes 9750. In either case, when the positioning member 9730c is rotated or twisted about its longitudinal axis, as indicated by arrow D, the electrodes 9750 move laterally, as indicated by arrow C, to the position shown in FIG. 38C. In other embodiments, other techniques can be used to move the electrodes 9750 in an automated or semi-automated manner. For example, referring now to FIG. 38D, the device 9700 can include pneumatic or hydraulic actuators 9731d, 9731e that also move the electrodes 9750 in a posterior-anterior direction, as indicated by arrow B, and a lateral or medial direction as indicated by arrow C. In this embodiment, the positioning members 9730 (shown as first and second positioning members 9730d, 9730e, respectively) can include pressure-transmitting tubing or conduits that deliver a pressurized fluid (e.g., a liquid or gas) to drive the actuators 9731d, 9731e. The actuators 9731c, 9731d can include linear motion cylinders (e.g., piston/cylinder combinations), bladders, balloons, and/or other suitable devices. The fluid can be provided/withdrawn by one or more corresponding pressure and/or vacuum sources 9732d, 9732e, which can either be controlled directly by an operator, or can be controlled via the controller 9790. In either case, the electrodes 9750 can be moved together or independently to any of a variety of suitable positions, for screening, testing, and/or long term or chronic therapy.

The foregoing techniques can be used to move the electrodes of any of the embodiments disclosed herein, individually or together, during a first (e.g. test phase) and/or a second (e.g. long-term phase), in response to operator inputs and/or automatically detected inputs. For example, the positions of the electrodes can be synchronized with the patient's physiologic characteristics, e.g., the patient's sleep state (awake, asleep or sleep stage), breathing effort, incidence of apnea/hypopnea, body position, blood oxygen level, response to prior stimulation, and/or other suitable physiologic parameters. In addition to moving the electrodes, the signal(s) applied to the electrode(s) can be changed to account for physiologic changes, e.g., by changing the amplitude, frequency, pulse width, duty cycle, and/or other signal delivery parameters.

In the foregoing description, numerous specific details are set forth to provide a thorough understanding of the present technology. In the foregoing description and for purposes of explanation, specific nomenclature is set forth to provide a thorough understanding of the present technology. However, it will be apparent to one skilled in the art that these specific details may not be required to practice the present technology. In other instances, well-known circuits and devices are shown in block diagram form to avoid obscuring aspects of the present disclosure. The term "coupled" as used herein means connected directly to or connected through one or more intervening components, circuits, or physiological matter. Any of the signals provided over various buses described herein may be time-multiplexed with other signals and provided over one or more common buses. Additionally, the interconnection between circuit elements or software blocks may be shown as buses or as single signal lines. Each of the buses may alternatively be a single signal line, and each of the single signal lines may alternatively be a bus, and a single line or bus might represent any one or more of a myriad of suitable physical or logical mechanisms for communication between components. Further, the logic levels and timing assigned to various signals in the description below are arbitrary and/or approximate, and therefore may be modified (e.g., polarity reversed, timing modified, etc.) as desired.

Elements from embodiments disclosed herein may be included in or substituted into other representative embodiments and/or may be combined with different illustrated representative embodiments in any suitable manner. For example, the feature of representative extensions attached to the lateral segments of the appliance by way of rigid flaps as shown in FIGS. 7-12, 16-21B, and 33A-35D may be used in combination with elements of other extension members and oral appliances. FIGS. 1-6, 22-24, 36A and 36B illustrate single electrodes on each lateral side of the oral appliance while FIGS. 7-12, 16-21B, 25, 33A-35D, and 37A-338D show multiple electrodes. Single electrodes on lateral sides or multiple electrodes on lateral sides may be used in various representative embodiments including those illustrated herein. While FIGS. 7-9 and 19-23B illustrate extensions with single extension attachment points to the appliance, in representative embodiments, either single or multiple attachment points may be used to attach an extension to the body of the oral appliance. Rigid elements may or may not be incorporated into extensions or extension arms of representative embodiments. Springs or resilient members may or may not be used in representative embodiments. Undulating or sinusoidal features may or may not be used in representative embodiments. Thicker inferior ends of extensions may or may not be included in representative embodiments. In representative embodiments, arms of extensions may or may not cross over each other. In representative embodiments, an oral appliance may have a stimulating electrode(s) positioned on single lateral side of the mouth such as shown in FIGS. 22-23B or on both lateral sides of the mouth. The various extensions described herein with respect to an interoral appliance or a test device can be interchangeable and can be different on each lateral side.

As used herein, the term "about" refers to values within 10% of the stated value. As used herein, the term "and/or," as in "A and/or B," refers to A alone, B alone and both A and B. To the extent any materials incorporated by reference conflict with the present disclosure, the present disclosure controls.

The following examples provide further representative devices and techniques in accordance with the present technology.

EXAMPLES

1. An intraoral electrical stimulation device, comprising:
an intraoral attachment body;
a guide element carried by the attachment body and having a constrained guide path;
an electrode movably supported relative to the guide element and movable along the constrained guide path to a plurality of positions;
a positioning member coupleable to the electrode to move the electrode along the constrained guide path; and
a signal generator coupleable to the electrode to direct a stimulation signal to the electrode.

2. The device of example 1, further comprising a flexible extension carrying the electrode, and wherein the flexible extension is moveable along the constrained guide path.

3. The device of any of examples 1-2, further comprising an extension carrying the electrode, and wherein the extension is one of multiple extensions, each having a different configuration, and each engageable with the positioning member.

4. The device of any of examples 1-3 wherein the guide element includes a tube positioned to slideably receive the positioning member.

5. The device of any of examples 1-4 wherein the guide element includes at least one groove forming the constrained guide path.

6. The device of example 5 wherein the at least one groove is oriented along a generally anterior-posterior axis.

7. The device of example 5 wherein the guide element incudes a plurality of grooves, each having a different location along a generally inferior-superior axis.

8. The device of any of examples 1-7 wherein the positioning member incudes a wire.

9. The device of any of examples 1-8, further comprising a handle coupled to the positioning member.

10. The device of any of examples 1-9, further comprising a position indicator carried by the attachment body and having indicia corresponding to a position of the electrode along the guide path.

11. The device of any of examples 1-10 wherein the signal generator includes a first, extraoral signal generator removably coupleable to the electrode and spaced apart from the attachment body, and wherein the device further comprises a second, intraoral signal generator carried by the attachment body.

12. The device of any of examples 1-11 wherein the positioning member is removable, and wherein the electrode is configured to be fixed relative to the guide path after being moved to a target position.

13. The system of example 1, further comprising:
a handle coupled to the positioning member;
a position indicator carried by the attachment body and having indicia corresponding to a position of the electrode along the guide path; and wherein:
the signal generator includes an extraoral signal generator removably coupled to the electrode and spaced apart from the attachment body; and
the handle, the positioning member, the position indicator, and the signal generator are removably coupled to the attachment member and removable from the attachment member when the electrode is fixed relative to the guide path.

14. The system of any of examples 1-13, further comprising an insert removably attachable to the attachment member, and wherein the insert includes molded surfaces positioned to fit over a patient's teeth.

15. The system of any of examples 1-14 wherein the positioning member is coupled to actuator to move the electrode relative to the guide element.

16. The system of example 15 wherein the actuator includes a mechanical actuator.

17. The system of example 15 wherein the actuator includes a fluid-driven actuator.

18. The system of example 15, further comprising:
a sensor;
a controller operatively coupled to the sensor and to the actuator, and programmed with instructions that, when executed, direct the actuator in response to a signal received from the sensor.

19. The system of example 18 wherein the sensor is configured to detect at least one of a patient's breathing, tongue motion, or EMG response.

20. An intraoral electrical stimulation device, comprising:
an intraoral attachment body;
a guide element carried by the attachment body and having at least one constrained guide path;
an electrode movably supported relative to the guide element and movable along the at least one constrained guide path to a plurality of positions;
a positioning member coupleable to the electrode to move the electrode along the at least one constrained guide path; and
an extraoral signal generator coupleable to the electrode to direct a stimulation signal to the electrode.

21. The device of example 20, further comprising a flexible extension carrying the electrode, and wherein the flexible extension is moveable along the constrained guide path.

22. The device of any of examples 20-21, further comprising an extension carrying the electrode, and wherein the extension includes multiple grooves engageable with the positioning member.

23. The device of any of examples 20-22 wherein the guide element includes a tube positioned to slideably receive the positioning member.

24. The system of any of examples 20-23 wherein the attachment body includes a base and an insert removably attachable to the base, and wherein the insert includes molded surfaces positioned to fit over a patient's teeth.

25. A method for fitting a patient with an intraoral electrical stimulation device, comprising:
placing an intraoral attachment body in the patient's oral cavity;
moving an electrode along at least one constrained guide path of the attachment body to a plurality of positions;
delivering an electrical signal to the patient via the electrode while the electrode is located at multiple individual positions constrained by the guide path;
receiving feedback corresponding to a patient response to the electrical signal delivered to the patient via the electrode while the electrode is located at the individual positions; and
based at least in part in the feedback, identifying a single one of the positions for subsequent delivery of electrical current to the patient.

26. The method of example 25 wherein the feedback corresponds to a characteristic of the patient's breathing.

27. The method of any of examples 25-26 wherein the electrode is carried by a flexible extension, and wherein the individual positions of the electrode have corresponding individual positions of the flexible extension relative to the attachment body.

28. The method of any of examples 25-27 wherein the at least one constrained guide path is a groove.

29. The method of any of examples 25-28 wherein the at least one constrained guide path extends in a generally anterior-posterior direction.

30. The method of any of examples 25-28 wherein the at least one constrained guide path extends in a generally superior-inferior direction.

31. The method any of examples 25-28 wherein the at least one constrained guide path is one of multiple guide paths extending in generally anterior-posterior directions, and wherein individual guide paths are offset from each other in a generally superior-inferior direction.

32. The method of any of examples 25-31 wherein moving the electrode includes moving the electrode with a wire-shaped positioning member.

33. The method of any of examples 25-32 wherein the intraoral electrical stimulation device includes:
a positioning member operably coupled to the electrode to move the electrode along the at least one constrained guide path;
a handle coupled to the positioning member;
a position indicator carried by the attachment body and having indicia corresponding to a position of the electrode along the guide path; and
an extraoral signal generator removably coupled to the electrode and spaced apart from the attachment body; and
wherein the method further comprises:
removing the handle, the positioning member, the position indicator, and the extraoral signal generator after receiving feedback corresponding to the patient response to the electrical signal delivered to the patient via the electrode while the electrode is located at the plurality of positions.

34. The method of example 33, further comprising installing an intraoral signal generator on the attachment member.

35. The method of any of examples 25-34 wherein the attachment body includes a base and an insert having a molded surface positioned to fit over the patient's teeth, and wherein the method includes removably connecting the insert to the base before placing the attachment body in the patient's oral cavity.

36. A method for fitting a patient with an intraoral electrical stimulation device, comprising:
during a first phase:
temporarily placing an intraoral attachment body in the patient's oral cavity;
moving an electrode along a first constrained guide path in a generally anterior-posterior direction;
moving the electrode along a second constrained guide path in a generally inferior-superior direction;
at each of multiple positions along the first and second guide paths, delivering at least one electrical signal to the patient via the electrode;
receiving feedback from the patient corresponding to a patient response to the at least one electrical signal delivered via the electrode at the multiple positions; and
based at least in part in the feedback, identifying an electrode position for subsequent delivery of an electrical signal to the patient; and
during a second phase, longer than the first phase:
delivering at least one subsequent electrical signal to the patient from an electrode at the electrode position.

37. The method of example 36 wherein delivering the at least one subsequent electrical signal to the patient during the second phase includes delivering at least one subsequent electrical signal over a period of weeks or months.

38. The method of any of examples 36-37 wherein the electrode used during the second phase is the same electrode as is used during the first phase.

39. The method of any of examples 36-38 wherein, during the second phase, the electrode is fixed at the electrode position.

40. The method of any of examples 36-38 wherein, during the second phase, the electrode is movable from the electrode position.

41. The method of example 40, further comprising:
receiving an input corresponding to a characteristic of the patient, from a sensor; and
in response to the input, automatically moving the electrode along at least one of the first and second constrained guide paths.

We claim:

1. An intraoral electrical stimulation device, comprising:
   an intraoral attachment body;
   a guide element carried by the attachment body and having a constrained guide path;
   an electrode movably supported relative to the guide element and movable along the constrained guide path to a plurality of positions;
   a positioning member coupleable to the electrode to move the electrode along the constrained guide path; and
   a signal generator coupleable to the electrode to direct a stimulation signal to the electrode.

2. The device of claim 1, further comprising a flexible extension carrying the electrode, and wherein the flexible extension is moveable along the constrained guide path.

3. The device of claim 1, further comprising an extension carrying the electrode, and wherein the extension is one of multiple extensions, each having a different configuration, and each engageable with the positioning member.

4. The device of claim 1 wherein the guide element includes a tube positioned to slideably receive the positioning member.

5. The device of claim 1 wherein the guide element includes at least one groove forming the constrained guide path.

6. The device of claim 5 wherein the at least one groove is oriented along a generally anterior-posterior axis.

7. The device of claim 5 wherein the guide element incudes a plurality of grooves, each having a different location along a generally inferior-superior axis.

8. The device of claim 1 wherein the positioning member includes a wire.

9. The device of claim 1, further comprising a handle coupled to the positioning member.

10. The device of claim 1, further comprising a position indicator carried by the attachment body and having indicia corresponding to a position of the electrode along the guide path.

11. The device of claim 1 wherein the signal generator includes a first, extraoral signal generator removably coupleable to the electrode and spaced apart from the attachment body, and wherein the device further comprises a second, intraoral signal generator carried by the attachment body.

12. The device of claim 1 wherein the positioning member is removable, and wherein the electrode is configured to be fixed relative to the guide path after being moved to a target position.

13. The device of claim 1, further comprising:
   a handle coupled to the positioning member;
   a position indicator carried by the attachment body and having indicia corresponding to a position of the electrode along the guide path; and wherein:
   the signal generator includes an extraoral signal generator removably coupled to the electrode and spaced apart from the attachment body; and
   the handle, the positioning member, the position indicator, and the signal generator are removably coupled to the attachment member and removable from the attachment member when the electrode is fixed relative to the guide path.

14. The device of claim 1, further comprising an insert removably attachable to the attachment member, and wherein the insert includes molded surfaces positioned to fit over a patient's teeth.

15. The device of claim 1 wherein the positioning member is coupled to actuator to move the electrode relative to the guide element.

16. The device of claim 15 wherein the actuator includes a mechanical actuator.

17. The device of claim 15 wherein the actuator includes a fluid-driven actuator.

18. The device of claim 15, further comprising:
   a sensor;
   a controller operatively coupled to the sensor and to the actuator, and programmed with instructions that, when executed, direct the actuator in response to a signal received from the sensor.

19. The device of claim 18 wherein the sensor is configured to detect at least one of a patient's breathing, tongue motion, or EMG response.

20. An intraoral electrical stimulation device, comprising:
   an intraoral attachment body;
   a guide element carried by the attachment body and having at least one constrained guide path;
   an electrode movably supported relative to the guide element and movable along the at least one constrained guide path to a plurality of positions;
   a positioning member coupleable to the electrode to move the electrode along the at least one constrained guide path; and
   an extraoral signal generator coupleable to the electrode to direct a stimulation signal to the electrode.

21. The device of claim 20, further comprising a flexible extension carrying the electrode, and wherein the flexible extension is moveable along the constrained guide path.

22. The device of claim 20, further comprising an extension carrying the electrode, and wherein the extension includes multiple grooves engageable with the positioning member.

23. The device of claim 20 wherein the guide element includes a tube positioned to slideably receive the positioning member.

24. The device of claim 20 wherein the attachment body includes a base and an insert removably attachable to the base, and wherein the insert includes molded surfaces positioned to fit over a patient's teeth.

\* \* \* \* \*